(12) United States Patent
Brooks et al.

(10) Patent No.: US 10,207,030 B2
(45) Date of Patent: *Feb. 19, 2019

(54) IMPLANTABLE DEVICES FOR BONE OR JOINT DEFECTS

(71) Applicant: University of Utah Research Foundation, Salt Lake City, UT (US)

(72) Inventors: Amanda Elaine Brooks, South Jordan, UT (US); David W. Grainger, Salt Lake City, UT (US); Kristofer D. Sinclair, Salt Lake City, UT (US); Benjamin Delbert Brooks, South Jordan, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/868,625

(22) Filed: Jan. 11, 2018

(65) Prior Publication Data

US 2018/0133374 A1    May 17, 2018

Related U.S. Application Data

(63) Continuation of application No. 14/765,662, filed as application No. PCT/US2014/014832 on Feb. 5, 2014, now Pat. No. 9,889,235.

(60) Provisional application No. 61/761,086, filed on Feb. 5, 2013.

(51) Int. Cl.
| | |
|---|---|
| *A61K 35/32* | (2015.01) |
| *A61K 9/52* | (2006.01) |
| *A61L 27/54* | (2006.01) |
| *A61L 27/56* | (2006.01) |
| *A61L 27/58* | (2006.01) |
| *A61L 27/30* | (2006.01) |
| *A61L 27/36* | (2006.01) |
| *A61K 31/7036* | (2006.01) |
| *A61L 27/26* | (2006.01) |
| *B05D 3/00* | (2006.01) |
| *B29C 67/24* | (2006.01) |
| *B29K 1/00* | (2006.01) |
| *B29L 31/00* | (2006.01) |

(52) U.S. Cl.
CPC .......... *A61L 27/58* (2013.01); *A61K 31/7036* (2013.01); *A61L 27/26* (2013.01); *A61L 27/306* (2013.01); *A61L 27/3608* (2013.01); *A61L 27/54* (2013.01); *B05D 3/002* (2013.01); *B29C 67/24* (2013.01); *A61L 2300/406* (2013.01); *A61L 2300/412* (2013.01); *A61L 2300/62* (2013.01); *A61L 2430/02* (2013.01); *A61L 2430/24* (2013.01); *B05D 2203/00* (2013.01); *B29K 2001/08* (2013.01); *B29L 2031/7532* (2013.01)

(58) Field of Classification Search
CPC .. A61L 27/56; A61L 2400/08; A61L 2430/02; A61L 31/146; A61L 27/3608; A61L 27/54; A61L 27/58; A61K 35/32
See application file for complete search history.

(56) References Cited

U.S. PATENT DOCUMENTS

| | | |
|---|---|---|
| 4,239,113 A | 12/1980 | Gross et al. |
| 5,164,187 A | 11/1992 | Constantz et al. |
| 5,475,063 A | 12/1995 | Kaplan et al. |
| 5,522,895 A | 6/1996 | Mikos |
| 5,679,723 A | 10/1997 | Cooper et al. |
| 5,766,618 A | 6/1998 | Laurencin et al. |
| 6,165,486 A | 12/2000 | Marra et al. |
| 6,224,794 B1 | 5/2001 | Amsden et al. |
| 6,284,758 B1 | 9/2001 | Egi et al. |
| 6,368,346 B1 | 4/2002 | Jadhav |
| 6,586,246 B1 | 7/2003 | Yoon et al. |
| 6,716,450 B1 | 4/2004 | Yin et al. |
| 6,846,853 B2 | 1/2005 | Shimp |
| 6,869,445 B1 | 3/2005 | Johnson |
| 6,893,465 B2 | 5/2005 | Huang |
| 6,949,251 B2 | 9/2005 | Dalal et al. |
| 6,991,647 B2 | 1/2006 | Jadhav |

(Continued)

FOREIGN PATENT DOCUMENTS

| | | |
|---|---|---|
| EP | 0243178 A2 | 10/1987 |
| EP | 1390086 B1 | 12/2004 |

(Continued)

OTHER PUBLICATIONS

Ahola et al., "An in vitro study of composites of poly(L-lactide-co-ε-caprolactone), β-tricalcium phosphate and ciprofloxacin intended for local treatment of osteomyelitis," Biomatter, vol. 3, Issue 2, e23162-1-e23162-13; 14 pages (2013).

(Continued)

*Primary Examiner* — Tracy Liu
(74) *Attorney, Agent, or Firm* — Sunstein Kann Murphy & Timbers LLP

(57) ABSTRACT

In one aspect, the invention provides an implantable device comprising a uniform mixture of components including degradable polymer, inorganic bone particulate either natural or synthetic, a drug, and a soluble microporagen. In some embodiments, the uniform mixture further includes a soluble polymer macroporagen. In some embodiments, the uniform mixture is coated with an immobilized outer porous layer comprising or consisting of synthetic or natural inorganic bone granules. In further aspects, the invention provides an implantable device comprising a composite core of degradable polymer, bone, and a drug, and a coating comprising or consisting of microporous bone overlayer covering the degradable composite core.

14 Claims, 30 Drawing Sheets

(56) References Cited

U.S. PATENT DOCUMENTS

| | | |
|---|---|---|
| 7,012,106 B2 | 3/2006 | Yuan et al. |
| 7,022,522 B2 | 4/2006 | Guan et al. |
| 7,041,641 B2 | 5/2006 | Rueger et al. |
| 7,122,057 B2 | 10/2006 | Beam et al. |
| 7,230,039 B2 | 6/2007 | Trieu et al. |
| 7,270,813 B2 | 9/2007 | Shimp et al. |
| 7,291,345 B2 | 11/2007 | Winterbottom et al. |
| 7,357,941 B2 | 4/2008 | Dalal et al. |
| 7,371,400 B2 | 5/2008 | Borenstein et al. |
| 7,390,498 B2 | 6/2008 | Dalal et al. |
| 7,572,298 B2 | 8/2009 | Roller et al. |
| 7,759,113 B2 | 7/2010 | Vacanti et al. |
| 7,776,021 B2 | 8/2010 | Borenstein et al. |
| 7,815,826 B2 | 10/2010 | Serdy et al. |
| 7,815,926 B2 | 10/2010 | Syring et al. |
| 7,837,740 B2 | 11/2010 | Semler et al. |
| 7,842,737 B2 | 11/2010 | Wang et al. |
| RE42,208 E | 3/2011 | Truncale et al. |
| 7,901,457 B2 | 3/2011 | Truncale et al. |
| 7,959,940 B2 | 6/2011 | Gale et al. |
| 7,989,532 B2 | 8/2011 | Li et al. |
| 8,012,210 B2 | 9/2011 | Lin et al. |
| 8,016,865 B2 | 9/2011 | Donnelly et al. |
| RE43,116 E | 1/2012 | Johnson |
| 8,119,705 B2 | 2/2012 | Wang et al. |
| RE43,258 E | 3/2012 | Truncale et al. |
| 8,167,787 B2 | 5/2012 | Gillis |
| 8,167,955 B2 | 5/2012 | Marrs et al. |
| 8,173,149 B2 | 5/2012 | Dalal et al. |
| 8,173,361 B2 | 5/2012 | Vacanti et al. |
| 8,178,013 B2 | 5/2012 | Kim |
| 8,192,665 B2 | 6/2012 | Huang et al. |
| 8,221,500 B2 | 7/2012 | Truncale et al. |
| 8,282,912 B2 | 10/2012 | Molenberg et al. |
| 8,292,968 B2 | 10/2012 | Truncale et al. |
| 8,293,530 B2 | 10/2012 | Burgess et al. |
| 8,309,114 B2 | 11/2012 | Gale et al. |
| 8,327,854 B2 | 12/2012 | Gillis et al. |
| 8,357,528 B2 | 1/2013 | Vacanti et al. |
| 8,377,356 B2 | 2/2013 | Huang et al. |
| 8,685,432 B2 | 4/2014 | Evans et al. |
| 9,889,235 B2 | 2/2018 | Brooks et al. |
| 2002/0049405 A1 | 4/2002 | Deslauriers et al. |
| 2002/0193883 A1 | 12/2002 | Wironen |
| 2004/0064193 A1 | 4/2004 | Evans et al. |
| 2005/0249697 A1 | 11/2005 | Uhrich et al. |
| 2005/0251266 A1 | 11/2005 | Maspero et al. |
| 2007/0178159 A1 | 8/2007 | Chen et al. |
| 2007/0191963 A1 | 8/2007 | Winterbottom et al. |
| 2007/0240725 A1 | 10/2007 | McKay |
| 2007/0299520 A1 | 12/2007 | Trieu et al. |
| 2008/0124400 A1 | 5/2008 | Liggins et al. |
| 2008/0139987 A1 | 6/2008 | Ambrosio et al. |
| 2009/0024174 A1 | 1/2009 | Stark |
| 2009/0048358 A1 | 2/2009 | Kim |
| 2009/0074871 A1 | 3/2009 | Sunwoo et al. |
| 2009/0130173 A1 | 5/2009 | Behnam et al. |
| 2009/0248172 A1 | 10/2009 | Neuenschwander |
| 2009/0287300 A1 | 11/2009 | Dave et al. |
| 2009/0324683 A1 | 12/2009 | Evans et al. |
| 2010/0021545 A1 | 1/2010 | Chaput et al. |
| 2010/0112032 A1 | 5/2010 | Guelcher et al. |
| 2011/0305741 A1 | 12/2011 | Zamora et al. |
| 2012/0029653 A1 | 2/2012 | Evans et al. |
| 2012/0053692 A1 | 3/2012 | Voor et al. |
| 2012/0213837 A1 | 8/2012 | Botchwey, III |

FOREIGN PATENT DOCUMENTS

| | | |
|---|---|---|
| WO | WO 02/087649 A1 | 11/2002 |
| WO | WO 2008/149096 A2 | 12/2008 |
| WO | WO 2011/127149 A1 | 10/2011 |
| WO | WO 2011/137231 A1 | 11/2011 |
| WO | WO 2012/059724 | 5/2012 |

OTHER PUBLICATIONS

Boyce et al., "The Influence of Processing on Safety and Performance," *Orthop. Clin. North Am.*, vol. 30, No. 4, pp. 571-581 (Oct. 1999).

Chen et al., "Results of vancomycin-impregnated cancellous bone grating for infected tibial nonunion," *Arch. Orthop. Trauma Surg.*, vol. 125, pp. 369-375 (Jun. 2005).

Davidoff et al., "A Robust Method to Coat Allograft Bone With a Drug-Releasing Polymer Shell," *BioMed. Sci. Instrum.*, vol. 46, pp. 184-189 (2010).

Fonge et al., "Bioanalysis of tobramycin for therapeutic drug monitoring by solid-phase extraction and capillary zone electrophoresis," *J. Chromatogr. B*, vol. 810, pp. 313-318 (Oct. 2004).

Frommelt, "Principles of systemic antimicrobial therapy in foreign material associated infection in bone tissue, with special focus on periprosthetic infection," *Injury, Int. J. Care Injured*, Supp. 2, pp. S87-S94 (May 2006).

Gubernator et al., "A simply and sensitive fluorometric method for determination of gentamicin in liposomal suspensions," *Int. J. Pharm.*, vol. 327, Nos. 1-2, pp. 104-109 (Dec. 2006).

Kokubo et al., "Solutions able to reproduce in vivo surface-structure changes in bioactive glass-ceramic A-W$^{3}$", *J. Biomed. Mater. Res.*, vol. 24, No. 6, pp. 721-734 (Sep. 2004).

Lochmann et al., "New protamine quantification method in microtiter plates using o-phthaldialdehyde/N-acetyl-L-cysteine reagent," *Int. J. Pharm.*, vol. 283, Nos. 1-2, pp. 11-17 (Sep. 2004).

Mashat et al., "Development and validation of HPLC method for the determination of tobramycin in urine samples post-inhalation using pre-column derivatisation with fluorescein isothiocyanate," *J. Chromatogr. B*, vol. 869, Nos. 1-2, pp. 59-66 (Jun. 2008).

Pedersen et al., "Plasma Amino Acids in Greenlanders and Danes. Influence of Seasons, Residence, Ethnicity, and Diet," *Am. J. Hum. Biol.*, vol. 18, No. 1, pp. 99-111 (Jan. 2006).

Rhyu et al., "In vitro release of vancomycin from vancomycin-loaded blood coated demineralised bone," *Int. Orthop.*, vol. 27, No. 1, pp. 53-55 (2003).

Sandell et al., "Release of Gentamicin from a ceramic bone substitute," GRIBOI Uppsala Sweden, May 10-12, 2012, 1 page.

Sayin et al., "Implantation of vancomycin microspheres in blend with human/rabbit bone grafts to infected bone defects," *J. Microencapsul.*, vol. 23, No. 5, pp. 553-566 (Aug. 2006).

Sevy et al., "Assay Method for Polymer-Controlled Antibiotic Release from Allograft Bone to Target Orthopaedic Infections," *Biomed. Sci. Instrum.*, vol. 46, pp. 136-141 (2010) [Abstract].

Stadelman et al., "Implants Delivering Bisphosphonate Locally Increase Periprosthetic Bone Density in an Osteoporotic Sheep Model. A Pilot Study," *Eur. Cell Mater.*, vol. 16, pp. 10-16 (Jul. 2008).

Trampuz et al., "Diagnosis and treatment of infections associated with fracture-fixation devices," *Injury, Int. J. Care Injured*, vol. 37, Suppl. 2, pp. S59-S66 (May 2006).

Walenkamp et al., "Gentamicin-PMMA Beads. Pharmacokinetic and Nephrotoxicological Study," *Clin. Orthop. Relat. Res.*, vol. 205, pp. 171-183 (Apr. 1986).

Winkler et al., "In vitro release of vancomycin and tobramycin from impregnated human and bovine bone grafts," *J. Antimicrob. Chemother.*, vol. 46, No. 3, pp. 423-428, (Sep. 2000).

Witsø et al., "Adsorption and release of antibiotics from morselized cancellous bone. In vitro studies of 8 antibiotics," *Acta Orthop. Scand.*, vol. 70, No. 3, pp. 298-304 (Jun. 1999).

Witsø et al., "Cancellous bone as an antibiotic carrier," *Acta Orthop. Scand.*, vol. 71, No. 1, pp. 80-84, (Feb. 2000).

Witsø et al., "Release of netilmicin and vancomycin from cancellous bone," *Acta Orthop. Scand.*, vol. 73, No. 2, pp. 199-205 (2002).

Witsoø et al., "Cortical allograft as a vehicle for antibiotic delivery," *Acta Orthop.*, vol. 76, No. 4, pp. 481-486 (Aug. 2005).

Wu et al., "Drug/device combinations for local drug therapies and infection prophylaxis," *Biomaterials*, vol. 27, No. 11, pp. 2450-2467 (Apr. 2006).

(56) References Cited

OTHER PUBLICATIONS

International Searching Authority U.S. International Search Report and Written Opinion of the International Searching Authority, International Application No. PCT/US2011/031394, dated May 23, 2011, 8 pages.
International Searching Authority U.S. International Search Report and Written Opinion of the International Searching Authority, International Application No. PCT/US2013/024792, dated Apr. 16, 2013, 8 pages.
European Patent Office, Extended European Search Report, Application No. 13746501.9-1455/2811940, dated Sep. 4, 2015, 6 pages.
European Patent Office, Communication pursuant to Rule 161(2) and 162 EPC, Application No. 14749065.0-1659, dated Sep. 30, 2015, 2 pages.
European Patent Office, Communication of European publication number and information on the application of Article 67(3) EPC, Application No. 14749065.0-1659, dated Nov. 18, 2015, 1 page.
Korean Intellectual Property Office, International Search Report and Written Opinion of the International Searching Authority, International Application No. PCT/US2014/014832, dated Aug. 7, 2014, 17 pages.

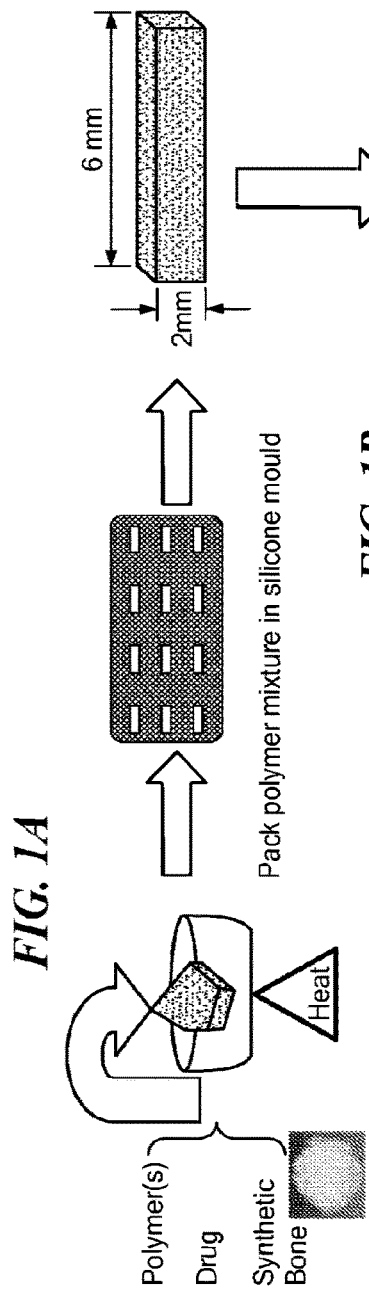
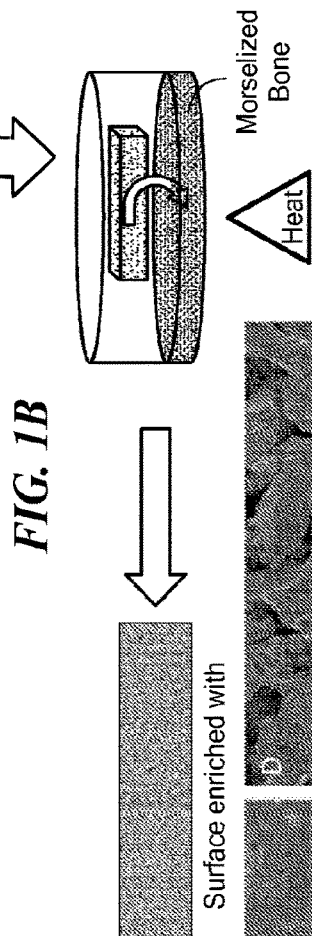
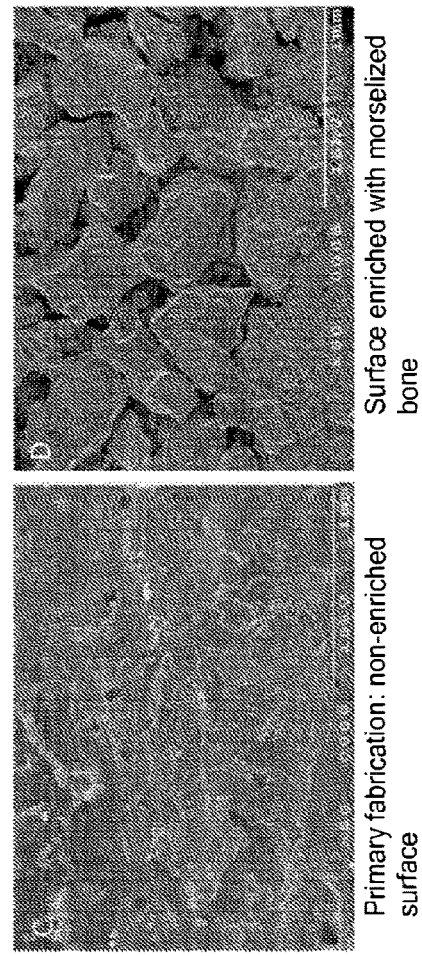
FIG. 1A
FIG. 1B
FIG. 2A Primary fabrication: non-enriched surface
FIG. 2B Surface enriched with morselized bone Slide Mold Silicone Isolator

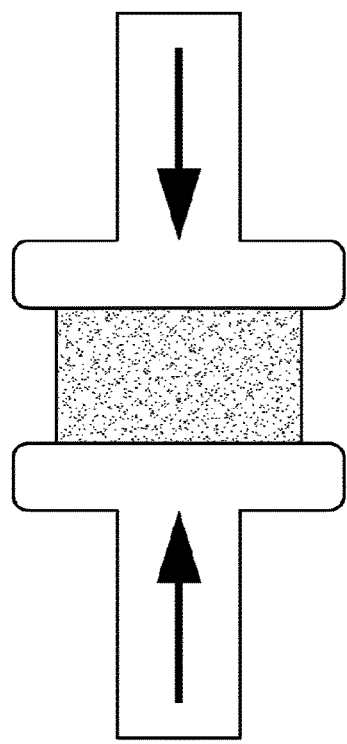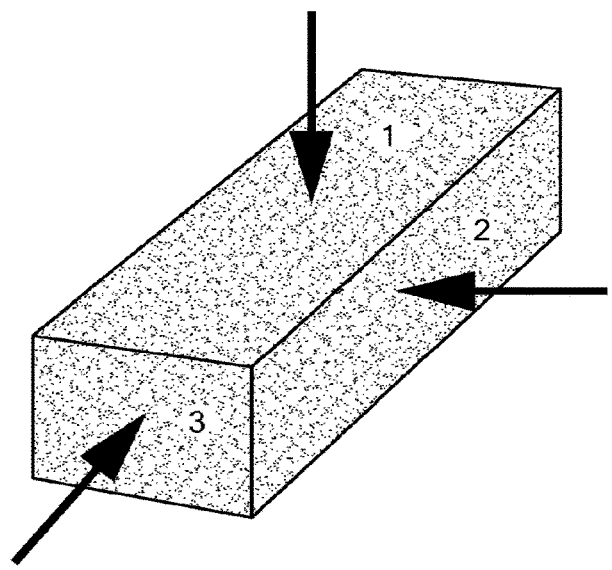
*FIG. 3A*
*FIG. 3B*

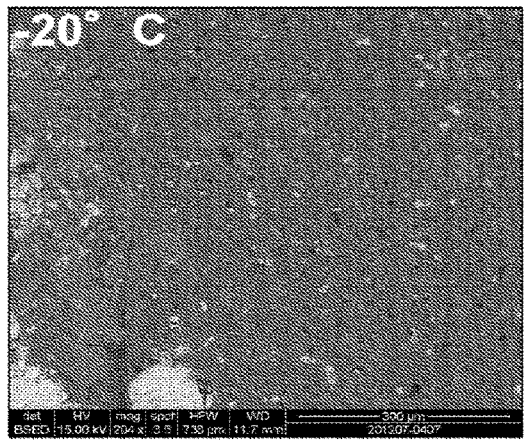 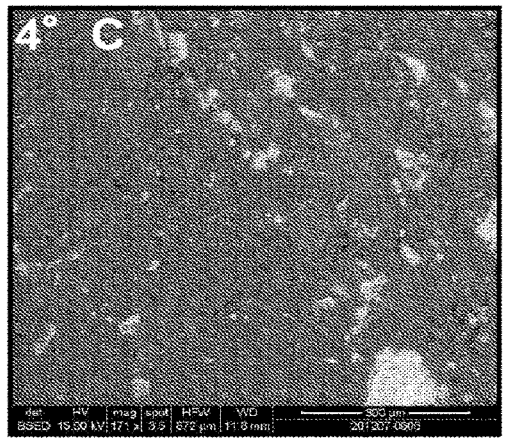
FIG. 7A          FIG. 7B
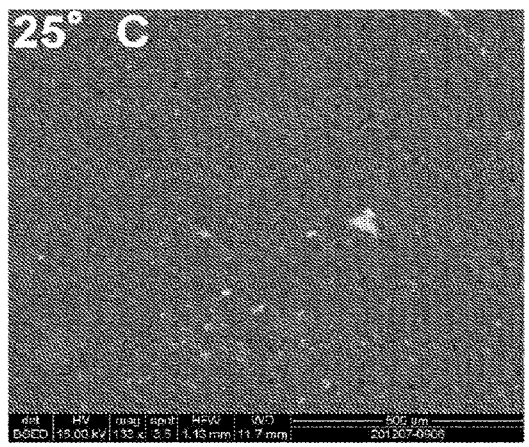 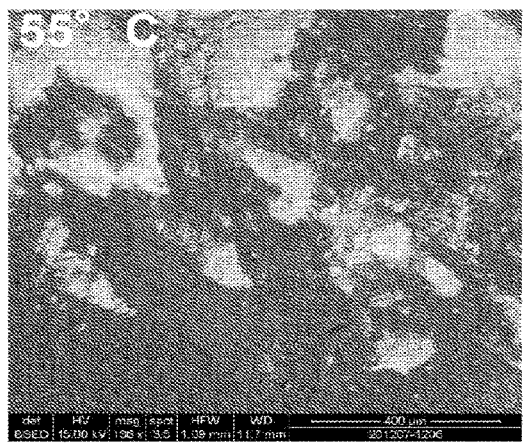
FIG. 7C          FIG. 7D

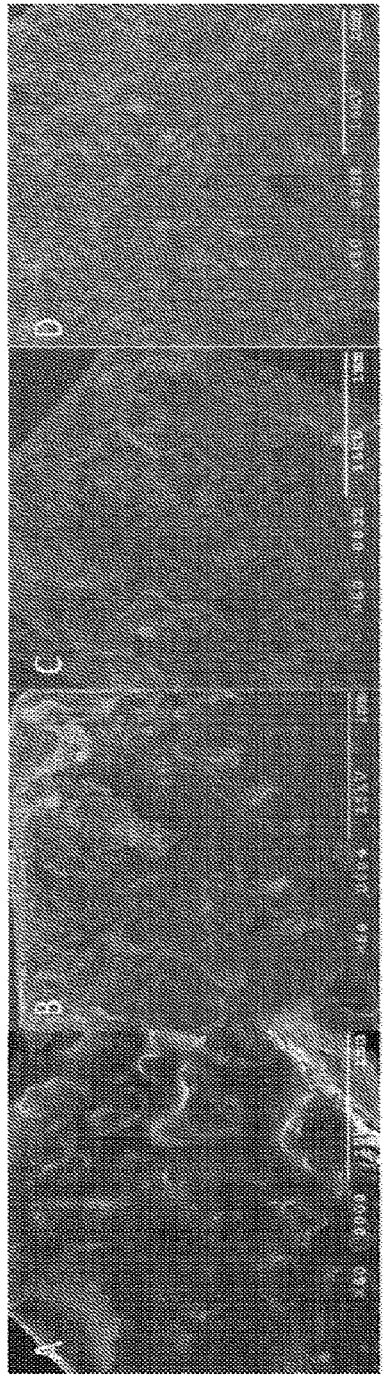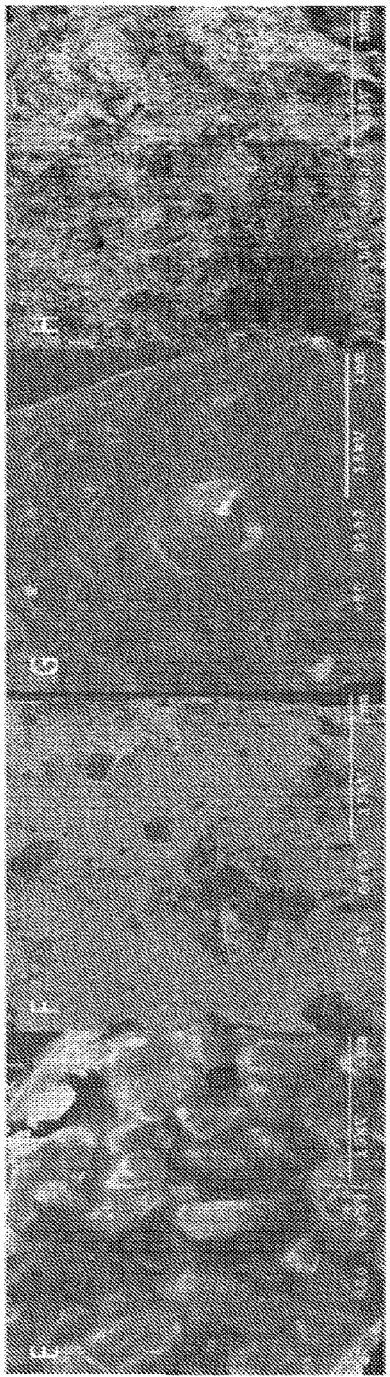

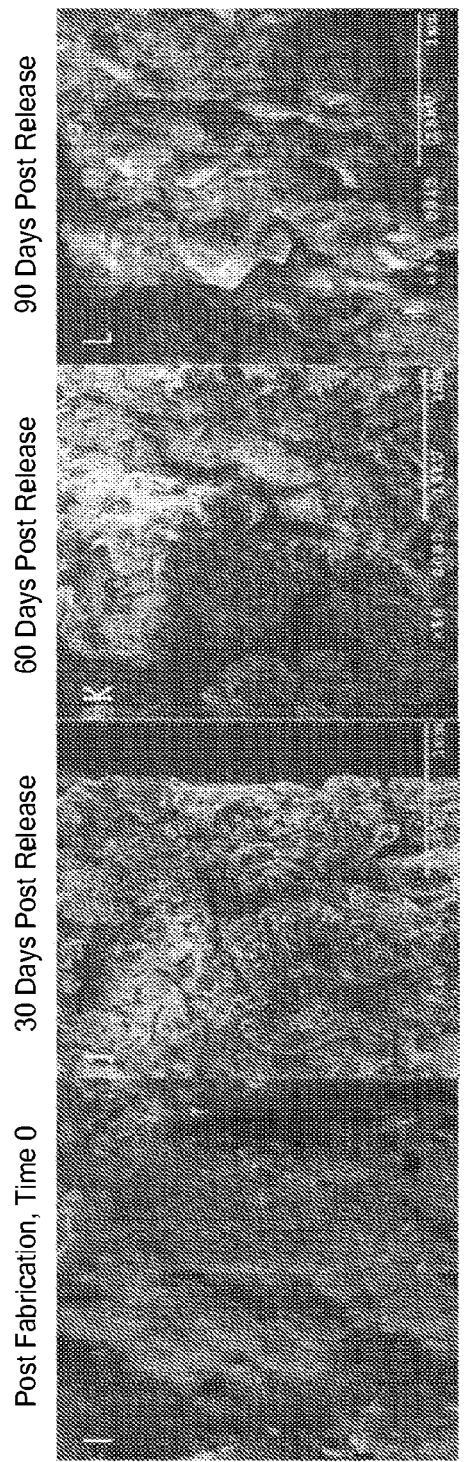

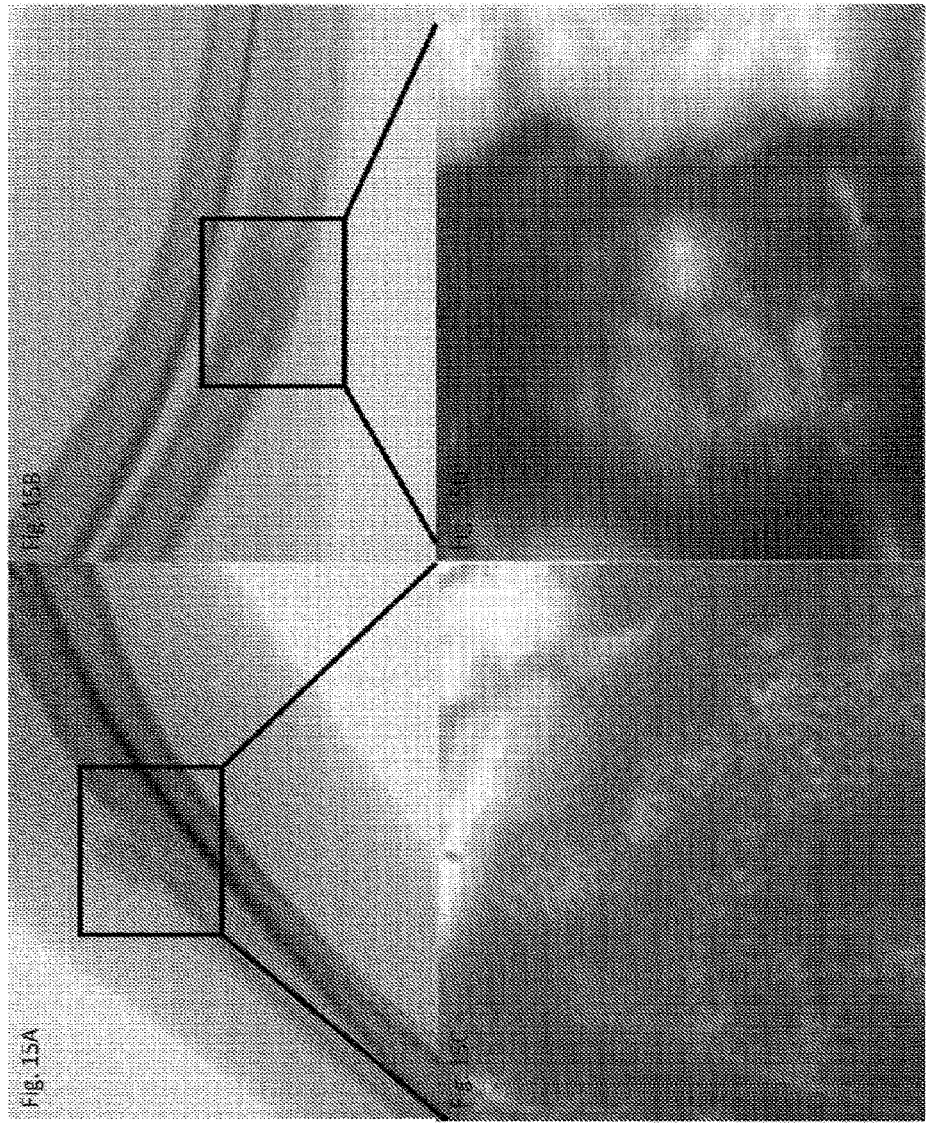

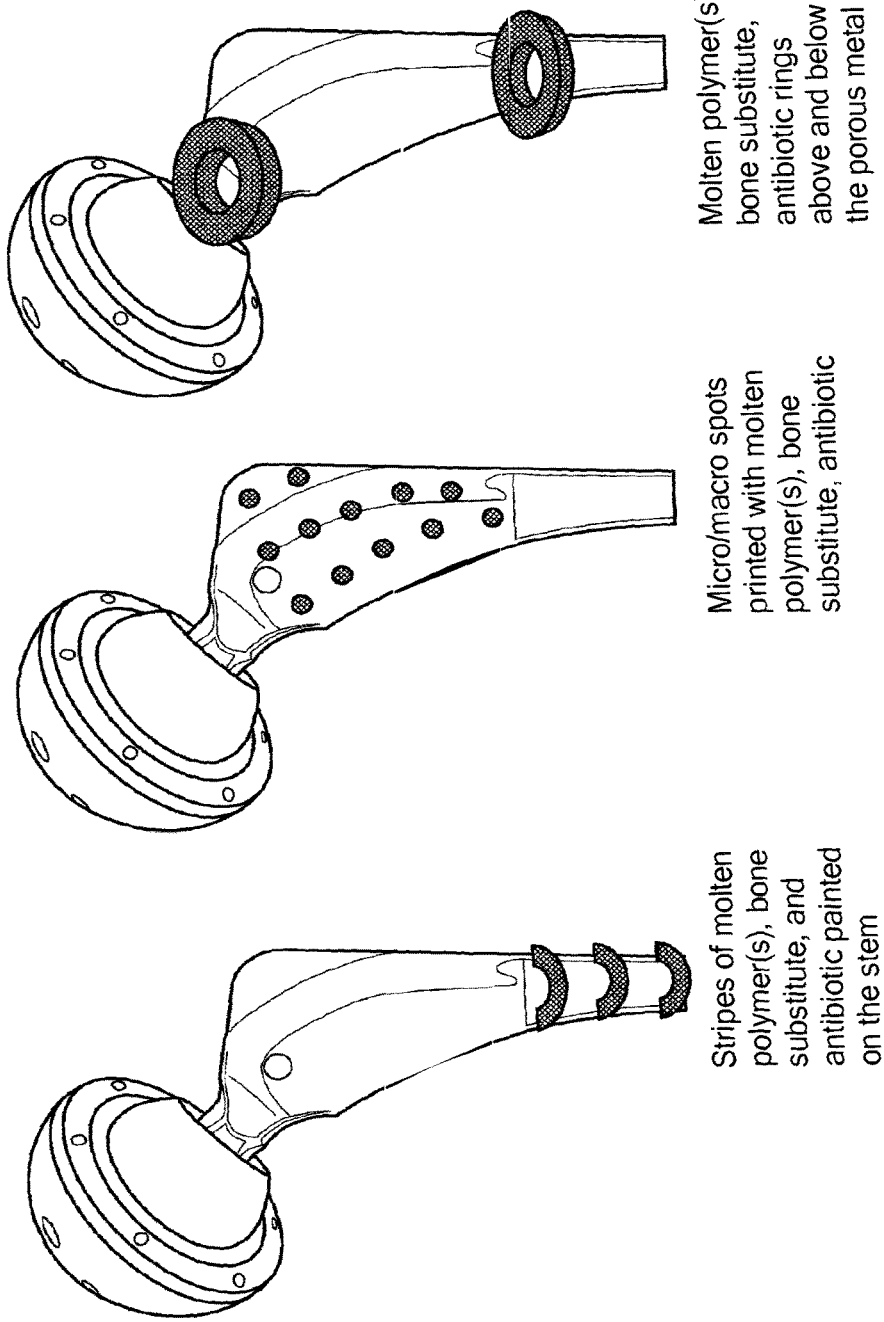

IMPLANTABLE DEVICES FOR BONE OR JOINT DEFECTS

CROSS-REFERENCE TO RELATED APPLICATION

This Application is a Continuation Application of U.S. patent application Ser. No. 14/765,662, filed Aug. 4, 2015, which is a § 371 application of International Patent Application No. PCT/US2014/014832, filed Feb. 5, 2014, which claims benefit from U.S. Provisional Application Ser. No. 61/761,086, filed Feb. 5, 2013, the entire contents of all of which are hereby incorporated by reference.

TECHNICAL FIELD

The present invention relates to implantable devices for the treatment of bone or joint defects.

BACKGROUND

Periprosthetic infection (PI) remains a challenging complication associated with total joint replacement (TJR, arthroplasty) surgeries—particularly for revision procedures with infection rates ranging from 8-15% and recurrent infection rates up to 30% [S. Kurtz, F. Mowat, K. Ong, N. Chan, E. Lau, and M. Halpern, "Prevalence of primary and revision total hip and knee arthroplasty in the United States from 1990 through 2002," *J Bone Joint Surg Am*, vol. 87, pp. 1487-97, 2005]. Traditional systemic antibiotics provide insufficient antibiotic delivery to infection sites to eliminate these implant-centered infections and strictly biomaterial device-based approaches are currently inadequate [M. P. Bostrom and D. A. Seigerman, "The clinical use of allografts, demineralized bone matrices, synthetic bone graft substitutes and osteoinductive growth factors: a survey study," *Hss J*, vol. 1, pp. 9-18, 2005; K. Vasilev, J. Cook, and H. J. Griesser, "Antibacterial surfaces for biomedical devices," *Expert Rev Med Devices*, vol. 6, pp. 553-67, 2009; H. Winkler, O. Janata, C. Berger, W. Wein, and A. Georgopoulos, "In vitro release of vancomycin and tobramycin from impregnated human and bovine bone grafts," *J Antimicrob Chemother*, vol. 46, pp. 423-8, 2000; E. Witso, L. Persen, K. Loseth, P. Benum, and K. Bergh, "Cancellous bone as an antibiotic carrier," *Acta Orthop Scand*, vol. 71, pp. 80-4, 2000; E. Witso, L. Persen, K. Loseth, and K. Bergh, "Adsorption and release of antibiotics from morselized cancellous bone. In vitro studies of 8 antibiotics," *Acta Orthop Scand*, vol. 70, pp. 298-304, 1999; P. Wu and D. W. Grainger, "Drug/device combinations for local drug therapies and infection prophylaxis," *Biomaterials*, vol. 27, pp. 2450-67, 2006]. Thus, treatment of PI may best be achieved through the use of a local antibiotic delivery system with effective, bone-implant integration. Local antibiotic delivery to bone often lacks control over drug release kinetics, resulting in an early burst release of drug, with subsequent sustained drug release at sub-therapeutic levels and for insufficient extended time periods. This unintentionally promotes local antibiotic resistance [M. P. Bostrom and D. A. Seigerman, "The clinical use of allografts, demineralized bone matrices, synthetic bone graft substitutes and osteoinductive growth factors: a survey study," *Hss J*, vol. 1, pp. 9-18, 2005]. Improved treatment of PI must not only incorporate local, controlled release mechanisms to deliver sufficient amounts of antibiotic to mitigate bacterial infection for extended durations, but also provide a void-filling scaffold to promote rapid osseointegration and restoration of bone typically lost during TJR surgery, particularly revision procedures. Combination implanted medical devices coupling an osteoconductive synthetic and biodegradable bone void filler (BVF) to promote active host bone growth and remodeling with extended antimicrobial release in situ to reduce implant reinfection rates and improve revision TJR procedure outcomes address these unmet clinical needs.

Clinical treatment of PI is complicated by bone's limited vascular supply [see Ketonis, C., et al., Clin Orthop Relat Res. 468(8): p. 2113-21, 2010; Landersdorfer, C. B., et al., Clin Pharmacokinet, 48(2): p. 89-12, 2009 and sequestra. Sequestra present a favorable, inert environment for harboring bacteria and allowing their unmitigated persistence in the protected avascular wound space Jones, S. A., et al., Wound Repair Regen, 2004. 12(3): p. 288-94, 2004; O'May, G. A., et al., "Osteomyelitis, in Biofilm Infections", T. Bjarnsholt (ed.), Springer Science+Business Media. p. 111-137, 2011]. In addition to their persistence in biofilm and sequestra, bacteria also evade host immune and pharmacological responses by developing antibiotic resistance through metabolic senescence in biofilms or invasion into and persistence within host osteoblasts and macrophages [K. J. Bozic, S. M. Kurtz, E. Lau, K. Ong, V. Chiu, T. P. Vail, H. E. Rubash, and D. J. Berry, "The epidemiology of revision total knee arthroplasty in the United States," *Clin Orthop Relat Res*, vol. 468, pp. 45-51, 2010; Wright and Nair, J. Med. Microbiol. 300(2-3): p. 193-204, 2010]. Clinical approaches routinely use local surgical device removal, surgical debridement of the tissue bed coupled with systemic antibiotic therapies, some extending for years, to attempt to eliminate TJR infections, prior to placement of a new device. Thus, current clinical tools to address acute and chronic bone infection are invasive, costly, and frequently ineffective, further compromising the patient's overall health and recovery [A. Gaudin, G. Amador Del Valle, A. Hamel, V. Le Mabecque, A. F. Miegeville, G. Potel, J. Caillon, and C. Jacqueline, "A new experimental model of acute osteomyelitis due to methicillin-resistant *Staphylococcus aureus* in rabbit," *Lett Appl Microbiol, vol.* 52, pp. 253-7, 2011; E. Moran, I. Byren, and B. L. Atkins, "The diagnosis and management of prosthetic joint infections," *J Antimicrob Chemother*, vol. 65 Suppl 3, pp. iii45-54, 2010]. Moreover, the economic burden for surgically addressing PI with revision TJR is calculated to be 5.3-7.2 times higher than that of primary TJR operations [A. Gaudin, G. Amador Del Valle, A. Hamel, V. Le Mabecque, A. F. Miegeville, G. Potel, J. Caillon, and C. Jacqueline, "A new experimental model of acute osteomyelitis due to methicillin-resistant *Staphylococcus aureus* in rabbit," *Lett Appl Microbiol*, vol. 52, pp. 253-7, 2011]. This amounts to $750 million in insurance and patient costs to treat spine, knee and hip infections and nearly $250 million in hospital losses yearly [P. V. Giannoudis, H. Dinopoulos, and E. Tsiridis, "Bone substitutes: an update," *Injury*, vol. 36 Suppl 3, pp. S20-7, 2005]. This billion-dollar infection impact remains unaddressed with effective clinical approaches.

No clinical long-term controlled release approaches exist for locally treating bone infection. Current approaches for treatment or prevention of PI fall into two groups, often administered simultaneously. Systemic antibiotic prophylaxis is considered the current clinical standard of care; however, studies are lacking to support this approach to PI [A. Gaudin, G. Amador Del Valle, A. Hamel, V. Le Mabecque, A. F. Miegeville, G. Potel, J. Caillon, and C. Jacqueline, "A new experimental model of acute osteomyelitis due to methicillin-resistant *Staphylococcus aureus* in rabbit," *Lett Appl Microbiol*, vol. 52, pp. 253-7, 2011; A. M.

Gonzalez Della Valle, "Effective Bactericidal Activity of Tobramycin and Vancomycin Eluted from Acrylic Bone Cement," *Acta Orthop Scand*, vol. 72, pp. 237-40, 2001]. While considered generally effective, problems with systemic antibiotic delivery include systemic side effects and low antibiotic concentration at bone infection sites, potentially promoting antibiotic resistance [A. Gaudin, G. Amador Del Valle, A. Hamel, V. Le Mabecque, A. F. Miegeville, G. Potel, J. Caillon, and C. Jacqueline, "A new experimental model of acute osteomyelitis due to methicillin-resistant *Staphylococcus aureus* in rabbit," *Lett Appl Microbiol*, vol. 52, pp. 253-7, 2011; T. Miclau, L. E. Dahners, and R. W. Lindsey, "In vitro pharmacokinetics of antibiotic release from locally implantable materials," *J Orthop Res*, vol. 11, pp. 627-32, 1993]. The second treatment option involves localized delivery of antibiotics directly to the site of infection. This strategy is commonly embodied by 1) surgical debridement with an antibiotic solution [P. V. Giannoudis, H. Dinopoulos, and E. Tsiridis, "Bone substitutes: an update," *Injury*, vol. 36 Suppl 3, pp. S20-7, 2005], 2) application of antibiotic solutions to bone grafts by soaking them in high concentration antibiotic solutions, and 3) implantation of antibiotic-loaded bone cements (only available during revision TJR). Surgical debridement with antibiotic solutions may provide immediate protection at the surgical site but has no lasting efficacy. Simple drug adsorption to bone without a controlled release design defaults to rapid bolus drug release within the first few days [T. N. Peel, K. L. Buising, and P. F. Choong, "Diagnosis and management of prosthetic joint infection," *Curr Opin Infect Dis*, vol. 25, pp. 670-6, 2012], with essentially no further release above the minimum inhibitory concentration [T. Miclau, L. E. Dahners, and R. W. Lindsey, "In vitro pharmacokinetics of antibiotic release from locally implantable materials," *J Orthop Res*, vol. 11, pp. 627-32, 1993]. These off-label graft-drug preparations lack uniform fabrication, validation, and dosing, and proven efficacy and may result in the development of antibiotic resistant pathogens [T. N. Peel, K. L. Buising, and P. F. Choong, "Diagnosis and management of prosthetic joint infection," *Curr Opin Infect Dis*, vol. 25, pp. 670-6, 2012]. Directly soaking bone filler materials in antibiotics is studied extensively. However, technology that endows this matrix with a legitimate, controlled release design for extended bioactive drug release has not been translated from laboratory to clinic [M. P. Bostrom and D. A. Seigerman, "The clinical use of allografts, demineralized bone matrices, synthetic bone graft substitutes and osteoinductive growth factors: a survey study," *Hss J*, vol. 1, pp. 9-18, 2005; H. Winkler, O. Janata, C. Berger, W. Wein, and A. Georgopoulos, "In vitro release of vancomycin and tobramycin from impregnated human and bovine bone grafts," *J Antimicrob Chemother*, vol. 46, pp. 423-8, 2000; T. N. Peel, K. L. Buising, and P. F. Choong, "Diagnosis and management of prosthetic joint infection," *Curr Opin Infect Dis, vol.* 25, pp. 670-6, 2012, Y. Achermann, M. Vogt, M. Leunig, J. Wust, and A. Trampuz, "Improved diagnosis of periprosthetic joint infection by multiplex PCR of sonication fluid from removed implants," *J Clin Microbiol*, vol. 48, pp. 1208-14, 2010; A. E. Brooks, B. D. Brooks, S. N. Davidoff, P. C. Hogrebe, M. A. Fisher, and D. W. Grainger, "Polymer-controlled release of tobramycin from bone graft void filler," *Drug Deliv and Transl Res*, vol. 3, pp. 518-530, 2013; S. N. Davidoff, J. O. Sevy, B. D. Brooks, D. W. Grainger, and A. E. Brooks, "Evaluating Antibiotic Release Profiles As A Function Of Polymer Coating Formulation," *Biomed Sci Instrum, vol.* 47, pp. 46-51, 2011; D. R. Osmon, E. F. Berbari, A. R. Berendt, D. Lew, W. Zimmerli, J. M. Steckelberg, N. Rao, A. Hanssen, and W. R. Wilson, "Diagnosis and management of prosthetic joint infection: clinical practice guidelines by the Infectious Diseases Society of America," *Clin Infect Dis*, vol. 56, pp. e1-e25, 2013]. Routine use of antibiotic-loaded bone cement (ALBC) is a classic example of local antibiotic delivery controlled by a glassy, non-swelling, non-biodegradable glassy polymer foreign body, presenting its own challenges.

To address the complete spectrum of implant infection risk and virulence factors, an active antimicrobial implant should maintain antibiotic concentrations at bactericidal levels for greater than 6 weeks, eliminating latent persister (senescent, quiescent or "sleeper") bacteria that due to their inactive metabolic states are not susceptible to most antibiotic activities [B. D. Brooks, K. D. Sinclair, S. N. Davidoff, S. Lawson, A. G. Williams, B. Coats, D. W. Grainger, and A. E. Brooks, "Molded polymer-coated composite bone void filler improves tobramycin controlled release kinetics," *J Biomed Mater Res*, vol. in press, 2013; A. E. Brooks, B. D. Brooks, S. N. Davidoff, B. P. Call, P. C. Hogrebe, M. Fisher, and D. W. Grainger, "Tailored Polymer-Controlled Release of Tobramycin from Allograft Bone Void Filler," *Pharmaceutics and Pharmaceutical Chemistry, Pathology, and Bioengineering.* Salt Lake City: University of Utah, 2010; A. E. Brooks, B. D. Brooks, S. N. Davidoff, P. C. Hogrebe, M. A. Fisher, and D. W. Grainger, "Polymer-controlled release of tobramycin from bone graft void filler," *Drug Deliv and Transl Res*, vol. 3, pp. 518-530, 2013] and reducing opportunities for acquired antibiotic resistance. Current implantable clinical antimicrobial products for TJR mitigation do not use degradable polymers to control antibiotic release and therefore release antibiotic for durations of a few days to maximum 3-4 weeks. Antibiotic-loaded bone cement, a standard of care for revision TJR procedures, exhibits a high initial burst release of antibiotics (up to 80% of total drug load within a few days), is a non-degradable foreign body in bone and tissue, and continues to elute antibiotic at sub-therapeutic concentrations [M. P. Bostrom and D. A. Seigerman, "The clinical use of allografts, demineralized bone matrices, synthetic bone graft substitutes and osteoinductive growth factors: a survey study," *Hss J*, vol. 1, pp. 9-18, 2005; H. Winkler, O. Janata, C. Berger, W. Wein, and A. Georgopoulos, "In vitro release of vancomycin and tobramycin from impregnated human and bovine bone grafts," *J Antimicrob Chemother*, vol. 46, pp. 423-8, 2000; W. A. Jiranek, A. D. Hanssen, and A. S. Greenwald, "Antibiotic-loaded bone cement for infection prophylaxis in total joint replacement," *J Bone Joint Surg Am*, vol. 88, pp. 2487-500, 2006; A. C. McLaren, "Alternative materials to acrylic bone cement for delivery of depot antibiotics in orthopaedic infections," *Clin Orthop Relat Res*, pp. 101-6, 2004] for weeks to months, or even years, beyond the intended antibiotic therapeutic window. Prolonged elution of antibiotic below the therapeutic level may inadvertently promote antibiotic resistance [D. Campoccia, L. Montanaro, P. Speziale, and C. R. Arciola, "Antibiotic-loaded biomaterials and the risks for the spread of antibiotic resistance following their prophylactic and therapeutic clinical use," *Biomaterials*, vol. 31, pp. 6363-77, 2010]. Unlike ALBC, a degradable and osteoconductive implanted matrix—allowing restoration of surgical site bone volumes—that also delivers antibiotics to infection sites locally at controlled, efficacious levels and extended durations beyond 6-8 weeks is not currently practiced. Some current art describes extended antibiotic release from largely degradable polymer implant matrices to bone infections; other art describes antibiotic delivery from largely inorganic implantable matrices.

SUMMARY OF THE EMBODIMENTS

In some embodiments, the invention provides formulation of the device to comprise a major component of osteo-inductive and/or osteo-conductive inorganic bone graft particulate coated by degradable polymer minority components as a composite solid implant for bone infections, with both of these biomaterials within the composite device each capable of carrying and releasing one or more antibiotics in various forms to bone infections over extended time periods currently unprecedented in total joint infection treatments. Some non-limiting advantages of such a combination device design over traditional systemic antibiotic therapy and antibiotic-loaded bone cement are that one or more antibiotics can be delivered for extended durations (6-12 weeks) locally to the implant infection site while the implant inorganic filler matrix supports osteoconduction and active bone remodeling.

Accordingly, in one aspect, the invention provides an implantable device comprising a uniform mixture of components including degradable polymer, bone, a drug, and a microporagen. In some embodiments, the device further comprises a macroporagen in the uniform mixture.

In some embodiments, the bone is natural bone or synthetic bone, or a mixture of natural and synthetic bone. For example, the synthetic bone may be ProOsteon. In some embodiments, the synethetic bone may be coralline-derived inorganic bone void filler. In some embodiments, the microporagen is $CaCl_2$. In some embodiments, the microporagen is $CaCl_2$, $MgCl_2$, $MgCO_3$, KCl, NaCl, $CaCO_3$, and/or calcium sulfate. In some embodiments, the uniform mixture is a composite.

In some embodiments, the macroporagen is polyethylene glycol (PEG). In some embodiments, the macroporagen is PEG, alginate, polyvinylpyrrolidone, NaCMC, hydroxypropylcelluose, and/or hyaluronic acid. In some embodiments, the macroporagen and the polymer are not the same.

In some embodiments, the device further comprises a coating covering the uniform mixture. For example, the coating may comprise, consist, or consist essentially of bone. For example, the coating may comprise, consist, or consist essentially of polymer. For example, the coating may comprise, consist, or consist essentially of a mixture of bone and polymer In some embodiments, the drug is microencapsulated. In some embodiments, the device may comprise one drug. In some embodiments, the device may comprise two or more drugs. In some embodiments, the drug may be dispersed throughout the uniform mixture.

In some embodiments, the drug is an antibiotic. In some embodiments, the drug is an osteoconductive cell mediator.

In some embodiments, the bone is present in a first amount, the polymer is present in a second amount, the drug is present in a third amount, and the microporagen is present in a fourth amount, by weight, in the uniform mixture. In some embodiments, the first amount is greater than the second amount, the third amount, the fourth amount, or a combined total of the second amount, the third amount, and the fourth amount. In some embodiments, the first amount is greater than the second amount, the third amount, the fourth amount, or a combined total of the second amount, the third amount, and the fourth amount by a factor of 1.25 times, or 1.5 times, or 1.75 times, or 2 times.

In some embodiments of the device, the bone is present in a first amount, the polymer is present in a second amount, the drug is present in a third amount, the microporagen is present in a fourth amount, and the macroporagen is present in a fifth amount, by weight, in the uniform mixture, and wherein the first amount is greater than the second amount, the third amount, the fourth amount, the fifth amount, or a combined total of the second amount, the third amount, the fourth amount, and the fifth amount. In some embodiments, the first amount is greater than the second amount, the third amount, the fourth amount, the fifth amount, or a combined total of the second amount, the third amount, the fourth amount, and the fifth amount by a factor of 1.25 times, or 1.5 times, or 1.75 times, or 2 times.

In some embodiments, the polymer is polycaprolatone (PCL). In some embodiments, the polymer is poly(lactic-co-glycolic) acid (PLGA). In some embodiments, the polymer is a mixture of polycaprolactone and poly(lactic-co-glycolic) acid. In some embodiments, the polymer is polyethylene glycol (PEG). In some embodiments, the polymer is a mixture of PCL and PEG, or a mixture of PLGA and PEG, or is a mixture of PCL and PEG and PLGA.

In some embodiments, implanted into a patient, said device and/or site of implantation is infection-free for at least six weeks following implantation, or at least eight weeks following implantation, or at least twelve weeks following implantation, or at least fourteen weeks following implantation.

In some embodiments, the degradable polymer has a structure and molecular weight selected so as to degrade over a time period when implanted into a patient and thereby release the drug over the time period. The time period may be at least six weeks following implantation, or at least eight weeks following implantation, or at least ten weeks following implantation, or at least twelve weeks following implantation, or at least fourteen weeks following implantation.

In another aspect, the invention provides an implantable device comprising (a) a core comprising a uniform mixture of components including degradable polymer, bone, and a drug, and (b) a coating comprising or consisting essentially of bone, said coating covering the core. In some embodiments, the core is a composite.

In some embodiments, core further contains a microporagen in the uniform mixture. In some embodiments, the core further contains a macroporagen in the uniform mixture.

In some embodiments, the microporagen is $CaCl_2$. In some embodiments, the microporagen is $CaCl_2$, $MgCl_2$, $MgCO_3$, KCl, NaCl, $CaCO_3$, and/or calcium sulfate. In some embodiments, the macroporagen is PEG. In some embodiments, the macroporagen is PEG. In some embodiments, the macroporagen is PEG, alginate, polyvinylpyrrolidone, NaCMC, hydroxypropylcelluose, and/or hyaluronic acid. In some embodiments, the macroporagen and the polymer are not the same.

In some embodiments, the bone is natural bone or synthetic bone, or a mixture of natural and synthetic bone. For example, the synthetic bone may be ProOsteon.

In some embodiments, the drug is microencapsulated. In some embodiments, the device may comprise one drug. In some embodiments, the device may comprise two or more drugs. In some embodiments, the drug may be dispersed throughout the uniform mixture.

In some embodiments, the drug is an antibiotic. In some embodiments, the drug is an osteoconductive cell mediator.

In some embodiments, the bone is present in a first amount, the polymer is present in a second amount, and the drug is present in a third amount, by weight, in the uniform mixture in the core. In some embodiments, the first amount is greater than the second amount, the third amount, or a combined total of the second amount and the third amount. In some embodiments, the first amount is greater than the second amount, the third amount, or a combined total of the second amount and the third amount, by a factor of 1.25 times, or 1.5 times, or 1.75 times, or 2 times.

In some embodiments of the device, the bone is present in a first amount, the polymer is present in a second amount, the drug is present in a third amount, and the microporagen is present in a fourth amount, by weight, in the uniform mixture in the core, and wherein the first amount is greater than the second amount, the third amount, the fourth amount, or a combined total of the second amount, the third amount, and the fourth amount. In some embodiments, the first amount is greater than the second amount, the third amount, the fourth amount, or a combined total of the second amount, the third amount, and the fourth amount by a factor of 1.25 times, or 1.5 times, or 1.75 times, or 2 times.

In some embodiments of the device, the bone is present in a first amount, the polymer is present in a second amount, the drug is present in a third amount, the microporagen is present in a fourth amount, and the macroporagen is present in a fifth amount, by weight, in the uniform mixture in the core, and wherein the first amount is greater than the second amount, the third amount, the fourth amount, the fifth amount, or a combined total of the second amount, the third amount, the fourth amount, and the fifth amount. In some embodiments, the first amount is greater than the second amount, the third amount, the fourth amount, the fifth amount, or a combined total of the second amount, the third amount, the fourth amount, and the fifth amount by a factor of 1.25 times, or 1.5 times, or 1.75 times, or 2 times.

In some embodiments, the polymer is polycaprolatone (PCL). In some embodiments, the polymer is poly(lactic-co-glycolic) acid (PLGA). In some embodiments, the polymer is a mixture of polycaprolactone and poly(lactic-co-glycolic) acid. In some embodiments, the polymer is polyethylene glycol (PEG). In some embodiments, the polymer is a mixture of PCL and PEG, or a mixture of PLGA and PEG, or is a mixture of PCL and PEG and PLGA.

In some embodiments, implanted into a patient, said device and/or site of implantation is infection-free for at least six weeks following implantation, or at least eight weeks following implantation, or at least twelve weeks following implantation, or at least fourteen weeks following implantation.

In some embodiments, the degradable polymer has a structure and molecular weight selected so as to degrade over a time period when implanted into a patient and thereby release the drug over the time period. The time period may be at least six weeks following implantation, or at least eight weeks following implantation, or at least ten weeks following implantation, or at least twelve weeks following implantation, or at least fourteen weeks following implantation.

In additional aspects, the invention provides methods for treating and/or preventing infection at a site of implantation in a patient in need of a bone or joint replacement, comprising implanting the devices described herein into the site of implantation.

In yet another aspect, the invention provides a method for manufacturing an implantable device comprising (a) combining a degradable polymer, a drug, a bone, and a microporagen over heat to make a uniform mixture by increasing the mixture temperature; (b) dispensing the heated uniform mixture into a mold of a pre-determined shape and size according to the anatomical need; (c) cooling the uniform mixture to a temperature at which the uniform mixture will harden in the mold; and (d) releasing the hardened uniform mixture from the mold to produce the implantable device. In further embodiments, the method further comprises (e) contacting the surface of the implantable device produced by step (d) with morselized bone, and (f) allowing the morselized bone to embed into the surface of the device to form a coating of bone on the device using mechanical force, ultrasonic energy or locally applied heat.

In some embodiments, the uniform mixture is a composite. In some embodiments, the degradable polymer may be suspended in a solvent (e.g., acetone) prior to mixing with the bone, drug, and microporagen over heat in step (a). In some embodiments, the polymer is polycaprolatone. In some embodiments, the polymer is poly(lactic-co-glycolic) acid. In some embodiments, the polymer is a mixture of polycaprolactone and poly(lactic-co-glycolic) acid.

In some embodiments, the bone is present in a first amount, the polymer is present in a second amount, the drug is present in a third amount, and the microporagen is present in a fourth amount, by weight, in the uniform mixture of step (a). In some embodiments, the first amount is greater than the second amount, the third amount, the fourth amount, or a combined total of the second amount, third amount, and the fourth amount. In some embodiments, the first amount is greater than the second amount, the third amount, the fourth amount, or a combined total of the second amount, third amount, and the fourth amount, by a factor of 1.25 times, or 1.5 times, or 1.75 times, or 2 times.

In some embodiments, the uniform mixture further includes a macroporagen in step (a).

In some embodiments, the degradable polymer has a structure and molecular weight selected so as to degrade over a time period when implanted into a patient and thereby release the drug over the time period. The time period may be at least six weeks following implantation, or at least eight weeks following implantation, or at least ten weeks following implantation, or at least twelve weeks following implantation, or at least fourteen weeks following implantation.

In yet another aspect, the invention provides a method for making an implantable device comprising (a) combining a degradable polymer, a drug, and a bone over heat to make a uniform composite mixture; (b) dispensing the heated uniform mixture into a mold of a pre-determined shape and size depending on anatomical need; (c) cooling the uniform mixture to a temperature at which the uniform mixture will harden; (d) releasing the hardened uniform mixture from the mold to obtain a composite device core; and (e) contacting the surface of core with morselized bone, and (f) allowing the morselized bone to embed into the surface of the composite core to obtain a bone-coated implantable device. In some embodiments, the uniform mixture is a composite. In some embodiments, the degradable polymer may be suspended in a solvent (e.g., acetone) prior to mixing with the bone, and drug over heat in step (a). In some embodiments, the polymer is polycaprolatone. In some embodiments, the polymer is poly(lactic-co-glycolic) acid. In some embodiments, the polymer is a mixture of polycaprolactone and poly(lactic-co-glycolic) acid.

In some embodiments, the uniform mixture further includes a microporagen in step (a). In some embodiments, the uniform mixture further includes a macroporagen in step (a).

In some embodiments, the bone is present in a first amount, the polymer is present in a second amount, and the drug is present in a third amount, by weight, in the uniform mixture of step (a). In some embodiments, the first amount is greater than the second amount, the third amount, or a combined total of the second amount and the third amount. In some embodiments, the first amount is greater than the second amount, the third amount, or a combined total of the second amount and the third amount, by a factor of 1.25 times, or 1.5 times, or 1.75 times, or 2 times.

In some embodiments, the degradable polymer has a structure and molecular weight selected so as to degrade over a time period when implanted into a patient and thereby release the drug over the time period. The time period may be at least six weeks following implantation, or at least eight weeks following implantation, or at least ten weeks following implantation, or at least twelve weeks following implantation, or at least fourteen weeks following implantation.

BRIEF DESCRIPTION OF THE DRAWINGS

The foregoing features of embodiments will be more readily understood by reference to the following detailed description, taken with reference to the accompanying drawings, in which:

FIGS. 1A and 1B are schematic diagrams showing a non-limiting method for producing molded composite bone void filler devices described in Example 1. FIG. 1A shows the process by which the molded composite bone void filler devices described as Formulations 1, 2, and 3 are produced. In FIG. 1A, polymer(s) (minority mixed fraction of PCL, PEG, and PLGA), solid (powder, pure) or liquid or solid microencapsulated drug, and a majority mass fraction of synthetic bone inorganic granules, croutons or matrices based on calcium salt solids are mixed and heated into a slurry, and then loaded into a pre-fabricated mold to cool, yielding multiple 6 mm×2 mm×2 mm bone void filler composite croutons comprising mostly inorganic bone-like solids by mass, with minority mass fraction of polymer coating and active antimicrobial drug within the polymer coating and also within the bone void filler matrix. FIG. 1B also shows the process by which one of a Formulation 1, 2, or 3 implant is also coated in morselized bone or similar calcium-based granules, croutons or solids to yield in a degradable antibiotic-eluting solid bone void filler implant whose outer surface is enriched with these immobilized morselized bone solids as coating or crust.

FIGS. 1C and 1D are not intended to be limiting or designate preferred shapes or sizes: virtually any shape or size is possible to mold with this approach.

FIGS. 2A and 2B shows representations of scanning electron microscopy images of molded composite bone void filler devices produced following the method set forth in FIGS. 1A and 1B either with (FIG. 2A) or without (FIG. 2B) enrichment of the bone void filler surface with immobilized, morselized inorganic or bone graft particulate coating.

FIGS. 3A and 3B are diagrams showing the physical stresses that can be used to apply to the bone void filler devices described herein. FIG. 3A shows a compression stressor, where the implant is shown as the black rectangle being compressed. FIG. 3B shows a rectangular block implant that can be subjected to stress in three different directions.

FIG. 6 is from the Group 2 fabrication described in Example 2, Table 2. The polymer only (no-drug (blank) polymer-coated bone void filler implant; dotted line, open circles) is the Group 2 fabrication described in Example 2, Table 2 that was formulated without tobramycin.

FIGS. 7A-7D are a series of scanning electron microscope (SEM) images of molded composite bone void filler devices stored at the indicated temperatures. The image shown in FIG. 7A was taken one month after −20° C. storage began. The image shown in FIG. 7B was taken following storage at 4° C. for 1 month. The image shown in FIG. 7C was taken after storage at 25° C. for 1 month. The image shown in FIG. 7D was taken after storage at 55° C. for 1 month. The data shown in these FIGS. 7A-7D is from the Group 2 fabrication described in Example 2, Table 2.

FIGS. 8A-8L are a series of Scanning electron microscopy (SEM) images comparing the aqueous in vitro degradation of the ElutiBone™ device based on the fabrication Group and the length of incubation in aqueous milieu. The implants shown in FIG. 8A-8D were made using the Group I formulation. The implants shown in FIG. 8E-8H were made using the Group 2 formulation. The implants shown in FIG. 8I-8L were made using the Group 3 formulation. The implants shown in FIG. 8A, 8E, abd 8I) were imaged at Time 0 in the aqueous millieu, The implants shown in FIGS. 8B, 8F, and 8J were imaged 30 days after the device was place in liquid milieu (1×PBS). The implants shown in FIGS. 8C, 8F, and 8K were imaged 60 days after the device was place in liquid milieu (1×PBS). The implants shown in FIGS. 8D, 8H, and 8L were imaged 90 days after the device was place in liquid milieu (1×PBS). Group 1 implants were made with PCL, PEG, ProOsteon 500R and 10% w/w tobramycin. Group 2 implants were made with PCL, PEG, calcium chloride, ProOsteon 500R, and 10% w/w tobramycin. Group 3 implants were made with PCL, PEG, PLGA, calcium chloride, ProOsteon 500R and 10% w/w tobramycin. Note that the Group 1, 2, and 3 formulations referred to in these FIGS. 8A-8L are from Example 1, Table 1 (Groups 1, 2, and 3 referred to in Table 1 as Formulations 1, 2, and 3, respectively). Note the vastly enhanced degradation of the Group 3 formulation compared to Group 1.

(FIG. 9A), 4° C. (FIG. 9B), 22° C. (FIG. 9C), and 55° C. (FIG. 9D) for the indicated times (1 week, 1 month, 2 months) then released under ambient conditions for the times indicated. After 1 day, the release is indistinguishable from the control fragments that were not stored prior to release. The data shown in these FIGS. 9A-9D is from the Group 2 fabrication described in Example 2, Table 2.

In FIG. 10B, the Group 3 device elution kinetics are shown in the inset to FIG. 10B, highlighting the detectable tobramycin above the MIC for S. aureus out to 7 weeks. Group 1 implants were made with PCL, PEG, ProOsteon 500R and 10% w/w tobramycin. Group 2 implants were made with PCL, PEG, calcium chloride, ProOsteon 500R, and 10% w/w tobramycin. Group 3 implants were made with PCL, PEG, PLGA, calcium chloride, ProOsteon 500R and 10% w/w tobramycin. Note that the Group 1, 2, and 3 formulations referred to in this FIG. 10A are from Example 1, Table 1 (Groups 1, 2, and 3 referred to in Table 1 as Formulations 1, 2, and 3, respectively).

(FIG. 11A); 4° C. (FIG. 11B); 22° C. (FIG. 11C); and 55° C. (FIG. 11D) for the times indicated. The data shown in these FIGS. 11A-11D is from the Group 2 fabrication described in Example 2, Table 2.

FIGS. 10A-10B is from the Group 2 fabrication described in Example 2, Table 2.

FIGS. 14A-14C is from the Group 2 fabrication described in Example 2, Table 2.

FIGS. 15A-15D show radiographs (FIGS. 15A and 15B) from an in vivo rabbit radial window defect infection model. In FIGS. 15A and 15C, a clinical grade commercial coralline-derived bone graft inorganic biomaterial (ProOsteon) only was implanted as a control and $10^5$ CFU of S. aureus was inoculated into the host bone medullary space perioperatively. In FIGS. 15B and 15D, a molded antibiotic-releasing composite bone void filler device (majority mass fraction of clinical grade commercial coralline bone graft inorganic biomaterial molded with PCL and PEG as the minority mass fraction polymer matrix) was implanted into bone and then $10^7$ CFU of S. aureus was inoculated into the host bone medullary space in the animal perioperatively. After euthanasia, the bone defect was dissected and processed for undecalcified plastic-embedded histology. A gram stain protocol for undecalcified bone was used to identify gram-positive bacteria in the animals of FIGS. 15A and 15B, and the results are shown in FIGS. 15C and 15D, respectively. As shown in the control in FIG. 15C (i.e., the animal from FIG. 15A), an abundance of Gram-positive stained bacteria is present in the bone. As shown in the test animal in FIG. 15D (i.e., the animal from FIG. 15B), the animal implanted with the antibiotic-containing molded composite bone void filler device showed a lack of Gram-positive bacteria. The data shown in the FIGS. 15B and 15D is an animal implanted with the Group 2 fabrication described in Example 2, Table 2.

*aureus* was given. In cohort 7, a Group 2 crouton from Example 2, Table 2 (PCL, PEG, ProOsteon granules, tobramycin) was implanted and $10^7$ CFU of *S. aureus* was applied. Note that there was no infection found in the blood of animals in any of the tested cohorts. Thus, the infection was localized and was not systemic. Moreover, this indicated that the infection was due to the perioperative inoculation of *S. aureus* at the site of implantation, and not from an unintended exogenous or alternative source.

Figure 17:
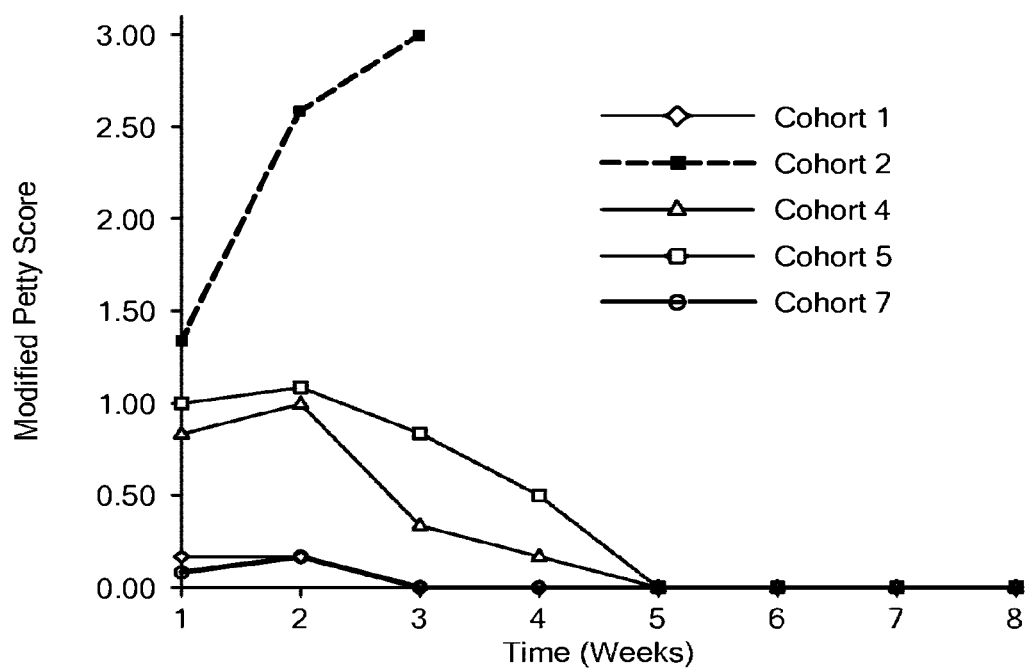

FIG. 17 is a line graph representing the morbidity (i.e., how sick the animals got) and health post-operatively of the animals from Cohort 1 (gray diamond on light gray line), Cohort 2 (black square on black dotted line), Cohort 4 (gray triangle on gray line), Cohort 5 (black square on light gray line) and Cohort 7 (gray circle on black line). In cohort 1 an unaltered clinical grade coralline-derived inorganic bone void filler crouton was implanted and no infectious inoculum was given. In Cohort 2 an unaltered clinical grade coralline-derived inorganic bone void filler crouton was implanted and $10^5$ CFU of *S. aureus* was applied. In cohort 4, a group 2 (example 2, table 2) crouton without antibiotic (PCL, PEG, clinical grade coralline-derived inorganic bone void filler) was implanted and $10^5$ CFU of *S. aureus* was applied. In cohort 5, a clinical grade coralline-derived inorganic bone void filler crouton was soaked in a 10% w/v tobramycin solution for 10 minutes prior to implantation and $10^5$ CFU of *S. aureus* was applied. In cohort 7, a Group 2 crouton from Example 2, Table 2 (PCL, PEG, clinical grade coralline-derived inorganic bone void filler granules, tobramycin) was implanted and $10^7$ CFU of *S. aureus* was applied.

Figure 18:
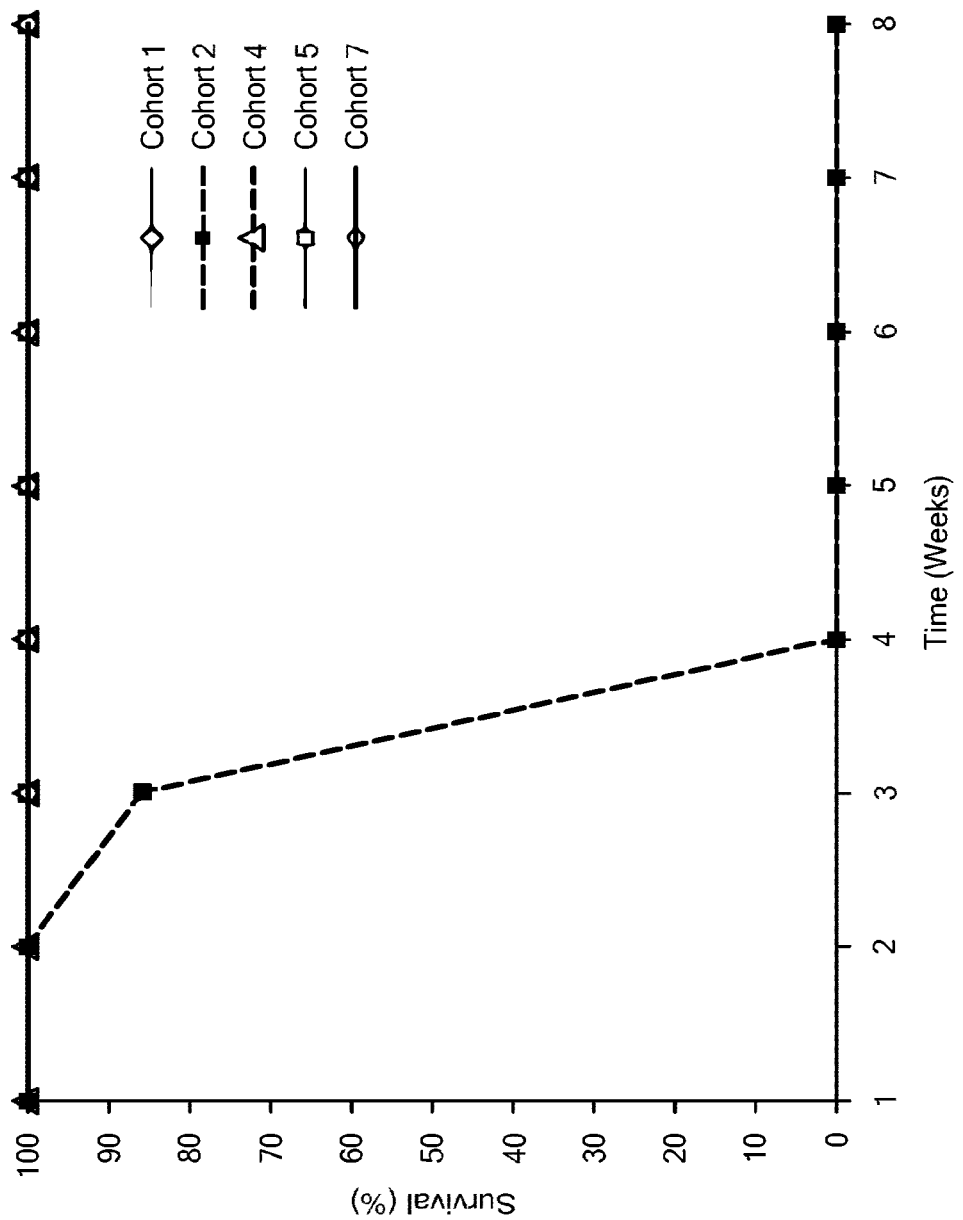

FIG. 18 is a line graph showing the survivability percentage of animals implanted with: clinical grade coralline-derived inorganic bone void filler without bacterial inoculum (Cohort 1-grey diamonds), a clinical grade coralline-derived inorganic bone void filler implant inoculated with $10^5$ CFU *S. aureus* (Cohort 2-black squares and dotted black line), and an implant device fabricated according to the methods described in Example 2 (tobramycin-containing—Group 1 formulation) and then dipped in a PCL acetone solution (60 mg/ml) with no drug, to create a PCL coating, with infection of $10^7$ CFU *S. aureus* bacteria (Cohort 7—grey circles with a black line). As shown in this FIG. 18, the PCL-coated implantable ElutiBone™ device with a high dosage of bacterial inoculum (Cohort 7; grey circles with a black line) showed as much survivability (100%) as the bone void filler with no bacterial inoculum (Cohort 1, grey diamonds). Additional control cohorts shown are Cohort 4 animals implanted molded composite bone void filler devices containing clinical grade coralline-derived inorganic bone void filler granules lacking any loaded antibiotic, and inoculated with $10^5$ CFU of *S. aureus* (gray triangle with gray line) and Cohort 5 animals implanted with clinical grade coralline-derived inorganic bone void filler soaked in 10% antibiotic solution (gray square with light gray line).

Figure 19A:
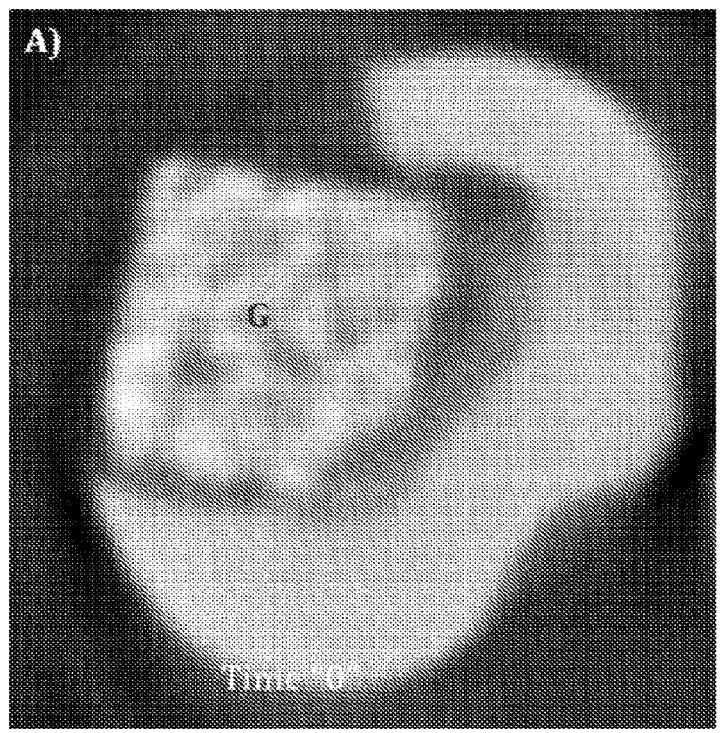
Figure 19B:
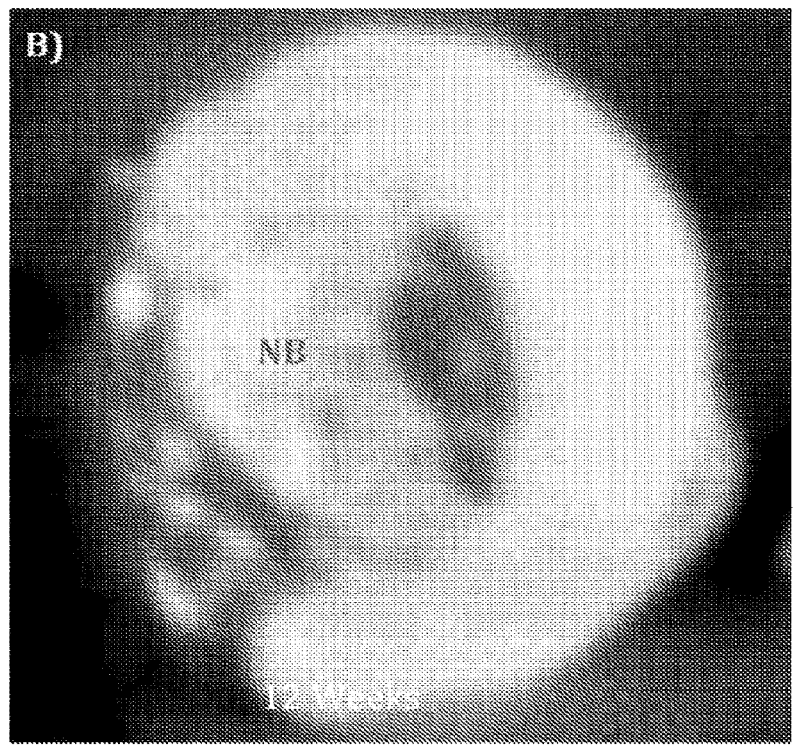

FIGS. 19A and 19B are micro-CT images of implanted devices made according to Formulation 4 of Table 1 in Example 1 taken after twelve weeks of bone implantation in vivo. Shown in a comparison of the device immediately after implantation (Time 0; FIG. 19A) and after 12 weeks implantation (FIG. 19B). The area labeled "G" is the implant and the area labeled "NB" is new bone.

Figure 20A:
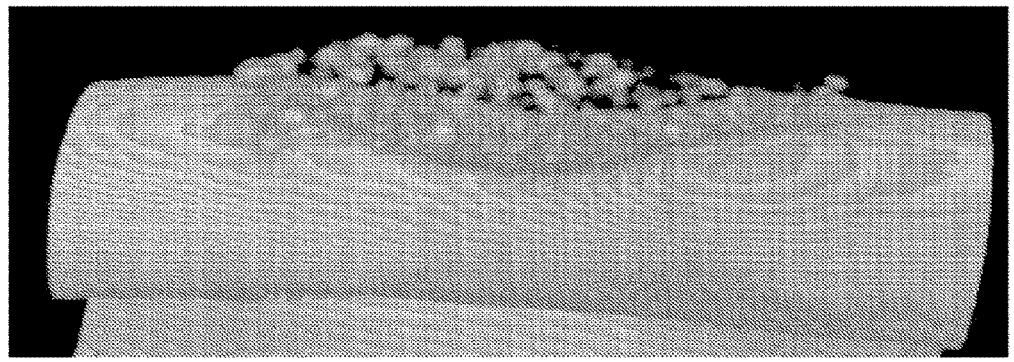
Figure 20B:
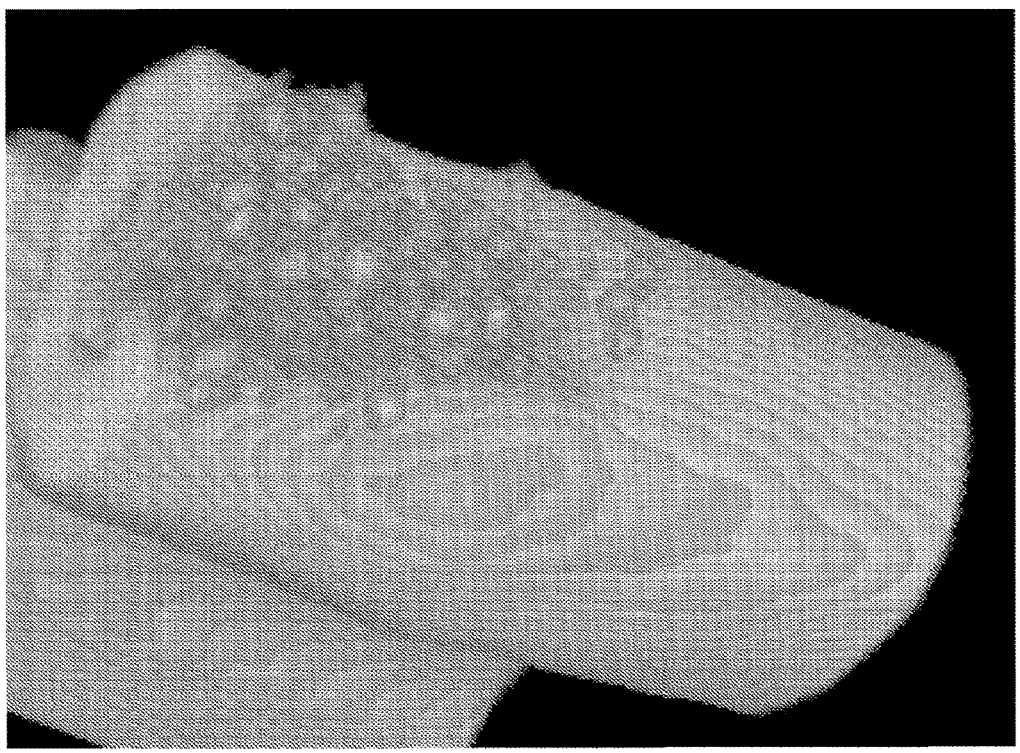
Figure 20C:
Figure 20D:
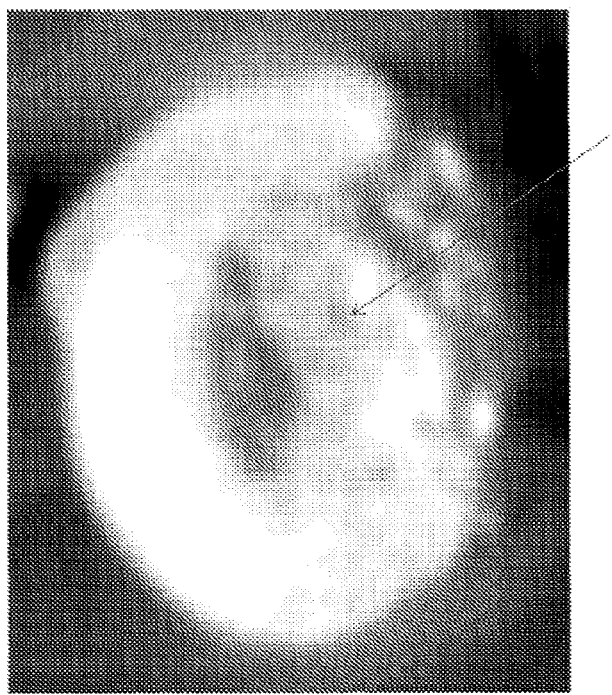

FIG. 20A-20D are micro-CT images of implanted devices made according to Formulation 4 of Table 1 in Example 1 taken twelve weeks after implantation in vivo. FIG. 20A shows a shallow groove with sparse mineralization representing the fragments of the implanted device. FIGS. 20B-20D are images showing the re-established intermedullary bone space. The red arrow in FIG. 120D shows mineralization representing newly deposited woven bone at the implant site.

Figure 21A:
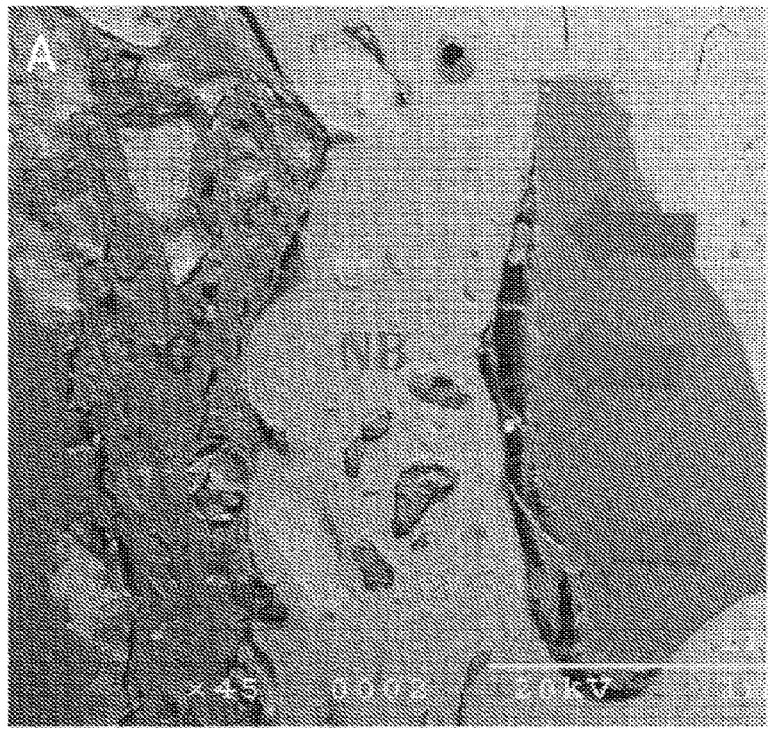
Figure 21B:
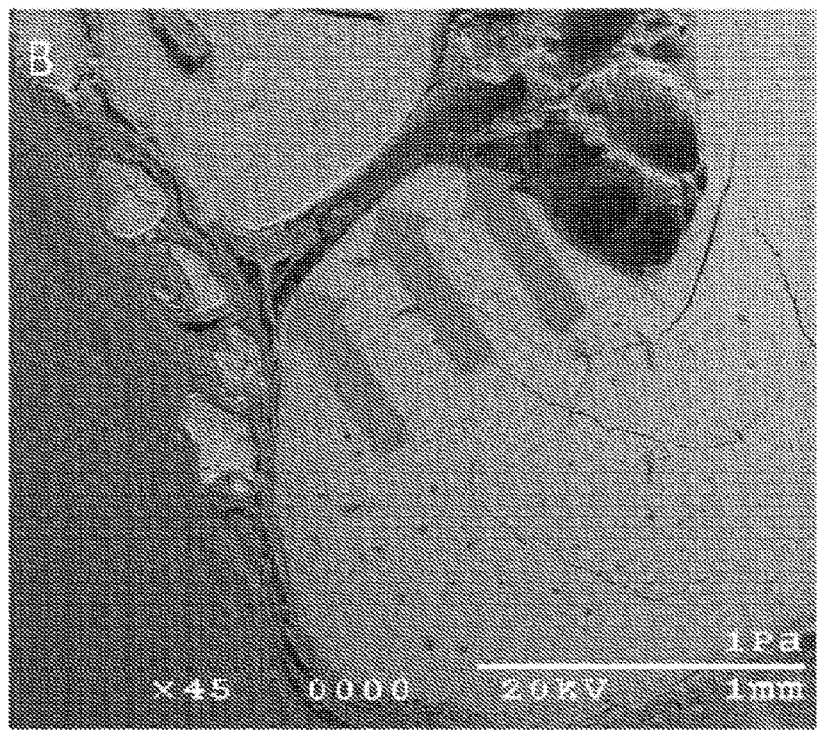

FIGS. 21A and 21B are backscatter Electron (BSE) image analysis at 12 weeks post-implantation: In FIG. 21A, the area labeled G indicates the implanted material (i.e., the bone filler) which was the Formulation 4 from Table 1 of Example 1 (PCL, PEG, PLGA polymer blend, solid particulate dispersed calcium chloride microporagen, solid particulate dispersed tobramycin, clinical grade coralline inorganic bone void filler granules with immobilized microporous outer synthetic bone granule coating). In FIG. 21A, the area labeled NB indicates new bone. Arrows in FIG. 21A point to newly formed bone bridge. Inorganic bone void granules from the implant can be seen scattered throughout the newly formed bone (see FIG. 21A. Thickness of "G" is significantly reduced from original 2 mm implant in FIG. 21A. In FIG. 21B, the) backscatter electron microscopy image of the one section taken from rabbit specimen that does not show complete bone bridging is shown. Arrows in FIG. 21B point to the tubular structure, likely a blood vessel, running from the endosteal space to the periosteal surface.

Figure 22:
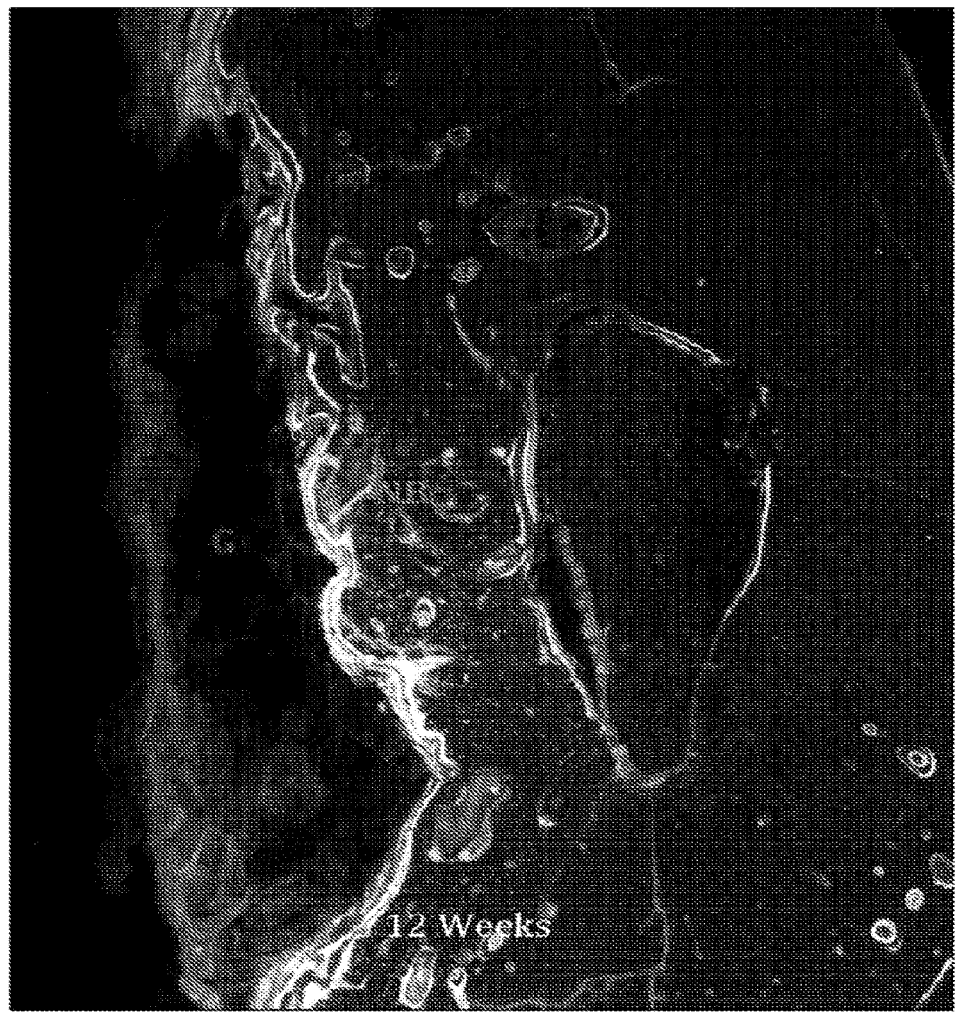

FIG. 22 is a fluorescent microscopy image of an animal implanted with a device made from the Formulation 4 formulation from Table 1 of Example 1. The figure shows the actively mineralizing bone surfaces indicated by incorporation of fluorescent calcein green. The area labeled "G" is the implanted device and the area labeled "NB" is new bone.

Figure 23:
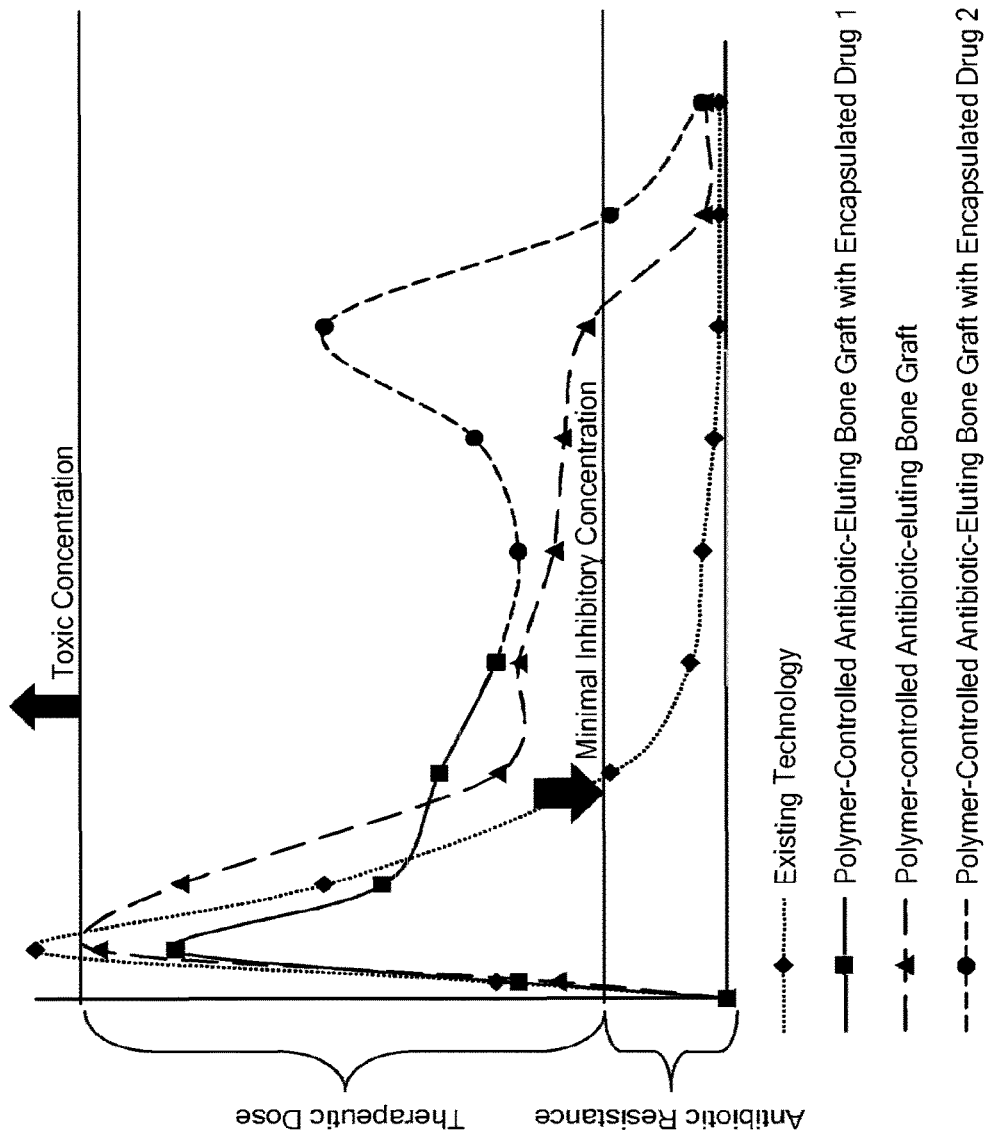

FIG. 23 is a line graph comparing the controlled drug release profile of a prior art implant such as antibiotic loaded bone cement (diamond, dotted line) with the release of drug from a polymer-controlled antibiotic-eluting bone void filler device (e.g., Formulation 1, 2, or 3 of Table 1 in Example 1) (triangle, dashed line), and the anticipated release of drugs from a contemplated dual drug releasing bone void filler; wherein the release of drug 1 follows the anticipated profile indicated by squares with a solid line and the release of drug 2 follows the anticipated profile indicated by circles with a solid line. Drug 1 and drug 2 may be encapsulated in a polymer shell where the polymer shell of drug one may be the same or different than the polymer shell of drug 2. The minimal inhibitory concentration (MIC) is the antibiotic efficacious threshold in a given volume (e.g., tissue space): when antibiotic release is below this concentration, pathogen killing is incomplete, and the infecting pathogen may also acquire drug resistance. Thus, the therapeutic antibiotic dose sought for an in vivo release antibiotic application is to remain above the minimal inhibitory concentration threshold for as long as possible.

FIGS. 24A-24D are images of PCL particles (FIGS. 24A and 24B) and PLGA microparticles (FIGS. 24C and 24D) either containing (FIGS. 24B and 24D) or not containing (FIGS. 24A and 24C) the indicated antibiotic drug. Images were captured at 40× on a Nikon microscope. These particles could be incorporated into the Group 3 or Group 4 composite formulation (polymer blends of PCL, PEG, PLGA together as a minority component, dispersed particles of calcium chloride microporagen, dispersed particles of tobramycin, and clinical grade coralline-derived bone void filler granules as the majority mass component).

FIGS. 25A-25C are diagrams showing three non-limiting different applications for the implantable devices described herein, where the device is used in combination with a prosthetic as an applied void filler adjunct to implant placement or as an on-board pre-applied degradable drug-releasing device on the prosthesis. Other antimicrobial applications for this implantable device as a temporary or permanent antibiotic-eluting void-filling spacer can also be contemplated.

DETAILED DESCRIPTION OF SPECIFIC EMBODIMENTS

In various aspects and embodiments, the invention provides bone void filler implants, devices, and methods and kits for making and using such implants and devices.

The further aspects, advantages, and embodiments of the invention are described in more detail below. The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Terms defined or used in the description and the claims shall have the meanings indicated, unless context otherwise requires. Technical and scientific terms used herein have the meaning commonly understood by one of skill in the art to which the present invention pertains, unless otherwise defined. Any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

To treat or prevent bone infection in surgery or during arthroplasties, often multiple clinical interventional approaches are taken, often simultaneously. Systemic antibiotic prophylaxis, where the antibiotic chosen is based on either culture results or reports of the most prevalent pathogens in the region, is considered the current clinical standard of care; however studies are lacking to prove its efficacy (Peel et al., Curr Opin Infect Dis. 25(6): p. 670-6, 2012; Bratzler, D. W. et al., Clin Infect Dis. 38(12): p. 1706-15 2004). While considered generally effective, problems with systemic antibiotic delivery include systemic side effects and low antibiotic concentration at bone infection sites—which can potentially promote bacterial colonization, mutation and acquired antibiotic resistance.

In another type of approach, surgeons absorb and apply antibiotic solutions to bone grafts by soaking them in high concentration antibiotic solutions (Landersdorfer, C. B., et al., Clin Pharmacokinet. 48(2): p. 89-124, 2009). Unfortunately, simple drug absorption to bone without a controlled release design defaults to rapid bolus drug release within the first few days (Bostrom and Seigerma, The Clinical Use of Allografts, Demineralized Bone Matrices, Synthetic Bone Graft Substitutes and Osteoinductive Growth Factors: A Survey Study. Hospital for Special Surgery 1: p. 9-18, 2005), with essentially no further release above the MIC to address remaining microbial threats out to the targeted 6 to 8-week time point considered by the orthopedic community as important for infection prevention (Moran, E et al., J Antimicrob Chemother. 65 Suppl 3: p. iii45-54, 2010). Furthermore, antibiotics and other drugs adhere too weakly to devices and are rapidly displaced from bone graft by serum proteins and other molecules in the biological milieu (O'May, G. A., et al., Osteomyelitis, in Biofilm Infections, T. Bjarnsholt (Ed.), Springer Science+Business Media. p. 111-137, 2011). These off-label graft-drug preparations lack uniform fabrication, validation, and standardized dosing that produce several consequences in vivo including both bacterial survival and possible development of antibiotic-resistant pathogens. While directly soaking bone filler materials (e.g., implantable devices) in antibiotic has been studied extensively, the idea of endowing this matrix with a legitimate, controlled release strategy designed for extended bioactive drug release has not been translated from the laboratory to the clinic.

Antibiotic-loaded bone cement (ALBC), or poly(methyl methacrylate) (PMMA) implants that elute drugs are examples of local antibiotic delivery controlled by a glassy, non-swelling, non-biodegradable polymer. These devices have been used in revision surgeries for arthroplasties to supplement systemic antibiotic efficacy. Unfortunately, ALBC suffers from multiple deficiencies. ALBC and PMMA devices (i.e., antibiotic-loaded bone cement) are not biodegradable and thus are recommended for removal or remain as a permanent implanted foreign body. ALBC and PMMA devices provoke the patient's innate tissue response to a foreign object, do not elute drug for more than six weeks, cannot deliver multiple drugs, and cannot uniformly and accurately release the drug load.

Biodegradable or resorbable drug carriers (e.g., collagen sponges, calcium salts and hydroxyapatite (HAP) blocks, fibrin glues, biomedical polyesters and other polymers, bioactive glass or glass ionomers) are deemed compatible with the body in certain clinical applications. However, without a controlled delivery strategy on-board, these materials, if endowed with antibiotics, release antibiotic payloads too quickly (i.e., often 1-4 days, frequently to one week, and infrequently to several weeks). Biodegradable drug carriers also resorb slowly as bulk biomaterials and generally offer very little or no programmed or controlled osteoconduction, osteoinduction or osteogenesis in bulk form (Giannoudis et al., Injury 3 Suppl. 3: S20-7, 2005). These biodegradable drug carriers also lack physiologically appropriate rigidity and malleability, are often biologically inconsistent and many cannot be sterilized. Therefore, while they can be tailored for effective drug release, they often do not represent biomaterials appropriate for device application for orthopedic implants in bone.

In some embodiments, the invention provides an implantable device that takes advantage of properties of both bone (e.g., high fractions of synthetic or natural inorganic particulate components) and biodegradable polymers. The implant devices described herein are designed to be biologically consistent, have physiologically appropriate rigidity and malleability, are endowed with diverse, tailored antimicrobial properties and can be sterilized. In contrast to ALBC and PMMA devices (i.e., antibiotic-loaded bone cement), the devices described herein are resorbable and degradable, can elute antibiotic drug for more than six weeks, can be loaded with an accurate amount of drug, and can be loaded with/elute multiple drugs if desired. Additionally, in contrast to ALBC and PMMA devices, the devices described herein are degradable, do not need to be removed, are resorbable by the patient's body, and do not provoke a chronic foreign body response within the patient upon resorption. The devices described herein support osteoconduction by the host's body.

The teachings of the following US patent publications are hereby incorporated by reference in their entireties: US20130273135, U20130209522, and US20090324683.

Accordingly, in a first aspect, the invention provides implantable device comprising a uniform mixture of dispersed components including degradable blended polymer (s), bone particulates, a dispersed drug, and a microporogen.

In another aspect, the invention provides an implantable device comprising (a) degradable, resorbable core consisting of a uniform mixture of components including degradable polymer (s), bone particulates, and a dispersed drug, and (b) an outer coating comprising or consisting essentially of particulate microporous bone, said coating covering the drug-releasing core.

The term "device" as used herein, refers to the fabricated device described herein that is meant to be implanted into a patient to either cure a bone or joint defect (e.g., a fractured bone or joint replacement), or to replace a previously inserted implant that has failed due to infection, surgical failure, and/or failure of the previously inserted implant. For example, the previous implant may not have structurally supported the defect, or may have initially supported the defect but, due to infection at the surgical site (i.e., the implantation site), becomes structurally compromised. The device may also be referred to as an implant or a bone void filler. In some embodiments, the device is substantially free of collagen.

A patient, of course, can be a human patient. A patient may also be a domesticated animal (e.g., snake, chicken, horse, dog, cat, cow, goat, etc.) or an exotic animal (e.g., elephant, lion, ostrich, Gila monster). In some embodiments, a patient is a vertebrate animal.

As the term is used herein, a "uniform mixture" is a mixture comprising two or more components, where the components are in approximately the same ratio to one another throughout the mixture, when considered at a macro level, even if at a molecular level the distribution of components is not even. For example, if the mixture is a solid block, a full thickness chip taken out of the solid will have approximately the same ratio of components as the larger block. In another example, a millimeter-sized chip removed from the bulk solid will have approximately the same ratio of components as the bulk solid. Likewise, if the mixture is in a liquid state, an aliquot of the mixture will have approximately the same ratio of components as the larger volume from which the aliquot was taken. In some embodiments, where the mixture is in a liquid state, the uniform mixture does not have to be stirred or agitated to maintain the uniformity of its components in the aliquot. In some embodiments, where the mixture is in a liquid state, the uniform mixture must be stirred or agitated for at least one minute prior to taking an aliquot to maintain the uniformity of its components in the aliquot. In some embodiments, the uniform mixture comprises a drug, where the drug is dispersed throughout the mixture. In the case of a solid implant or device, some components are uniformly distributed as solid particulates (e.g., bone or drug) throughout the mixture. For example, the solid particulate (e.g., bone) may be the majority (by mass) mixed with a minority molten or liquid matrix in the uniform mixture. In some embodiments, the uniform mixture is a composite.

The term "bone", as used herein, can mean either synthetic bone (e.g., inorganic calcium bone fillers known to the clinical specialties in bone substitution/replacement), or natural bone (e.g., natural bone collected and processed from living vertebrate animals or from human cadavers). In some embodiments, no living MHC-expressing cells are included in bone. In some embodiments, no MHC antigen is included in bone. In some embodiments, the bone is substantially free of any protein. One non-limiting protein that the bone is substantially free of is collagen.

In some embodiments, the bone is synthetic bone-like solid inorganic material. Synthetic bone is, of course, free of protein. Synthetic bone may be fabricated or synthesized by man, or may be obtained commercially. Synthetic bone can be readily directly and routinely synthesized from calcium or strontium-based salt or oxide precursors in large batches in commercial ovens, and pulverized (i.e., ground) into pieces and granules, sterilized and certified to be clinical grade filler biomaterial. In some embodiments, the bone is a synthetic calcium-based inorganic particulate construct comprising calcium-based minerals found in or derived from natural bone. In some embodiments, the synthetic bone may be coralline-derived inorganic bone void filler granules. Synthetic bone is also commercially available and/or clinical grade. One non-limiting commercially available synthetic bone is the ProOsteon bone commercially available from Biomet, Warsaw, Ind., comprising a natural coral extracted solid that is then processed synthetically with hydroxyapatite for bone void filling or as bone graft.

Natural bone may be collected or harvested from living vertebrate animals, or collected or harvested from the recipient of the implant (autograft bone) or cadavers (e.g. cadaver-derived bone, which is allogeneic to the recipient of the implant). Autograft bone, or patient-harvested bone, is the gold standard for bone grafting, providing a highly compatible, bioactive, structural matrix as the basis for wound healing. However, cellular death during transplantation, inadequate sourcing due to other pathologies, harvest site morbidity, pain, and cosmetic disfigurement, culminate in a substantial 8.5-20% complication risk, including acute and chronic or recurring infection (Nandi et al., *Indian J Med Res*, vol. 132, pp. 15-30, 2010; Kundu et al., *J Mater Sci Mater Med*, vol. 21, pp. 2955-69, 2010; Aronin et al., *Biomaterials*, vol. 31, pp. 6417-24). Thus, allograft or cadaveric-sourced bone tissue has become an increasingly popular defect and wound packing material, increasing 15-fold over the past decade to now account for almost a third of the over 500,000 orthopedic graft procedures performed annually in the United States to treat traumatic or other boney defects (Aronin et al., supra; Kanellakopoulou and E. J. Giamarellos-Bourboulis, *Drugs*, vol. 59, pp. 1223-32, 2000). Importantly, allograft bone is processed to remove all cellular and proteinaceous components (e.g., collagen is removed), leaving only the osteoconductive, and to a more limited extent, osteoinductive mineral (inorganic) component of the bone to provide a structural template for orthopedic repair, and promote integration and turnover by the patient's natural osteoclast and osteoblast populations.

In some embodiments, the bone is morselized (e.g., pulverized or fragmented) into micron-sized particles. In some embodiments these particulates are between 150 and 425 μm. In some embodiments, the bone is sterilized (e.g., in an autoclave or by gas diffusion sterilization). In some embodiments, the bone or bone graft is intended to be used clinically as a replacement device to fill bone or joint defects and allow production (e.g., by providing a scaffold) of new autologous bone by the host receiving the implant.

As the term is used herein, by "polymer" is meant a macromolecule composed of many repeated subunits. In some embodiments, the polymer is degradable. For example, a degradable polymer in an implantable device will eventually degrade to subunits of the macromolecule precursor. In some embodiments, the degradation process is accelerated upon implantation of the device into a patient due to, for example, the maintained heated environment (e.g., 37° C.), the ever-presence of water, presence of host enzymes and the presence of host cells and/or pathogens (e.g., bacteria) abutting the device comprising the polymer and, with time, invading the device comprising the polymer.

In some embodiments, a non-limiting type degradable polymer used in the devices described herein is polycaprolactone (PCL). PCL degrades by hydrolysis of its ester linkages in the presence of water. The rate at which PCL degrades depends upon its molecular weight and degree of crystallinity. Polycaprolactone (PCL) supports osteoblast growth (see Chang, H. I. et al., J Control Release 110(2): p. 414-21, 2006) and also releases tobramycin within the therapeutic window while degrading slowly to allow bone growth and eventual remodeling.

In some embodiments, a non-limiting type polymer used in the devices described herein is poly(lactic-co-glycolic) acid (PLGA). PLGA degrades by hydrolysis of its ester linkages in the presence of water. The rate at which PLGA degrades depends upon the ratio of lactic acid to glycolic acid in the PLGA (e.g., a PLGA 75:25 is 75% lactic acid and 25% glycolic acid). PLGA 50:50 degrades in about two months in the presence of water.

In some embodiments, a non-limiting type of polymer used in the devices described herein is polyethylene glycol (PEG). Polyethylene glycol (PEG), another pervasive, clinically familiar (i.e., GRAS-designated) polymer is highly soluble in water and biological fluids and used in the devices described herein as to both control drug release and also as a macroporagen to alter drug release kinetics.

In some embodiments, where a polymer such as polyethylene glycol (PEG) is used as a poragen, the implantable device contains another polymer. In other words, the same polymer (e.g., polyethylene glycol (PEG)) cannot be the only polymer in an implantable device as described herein. As it pertains this this embodiment, this limitation does not mean that the degradable polymer of the implantable device cannot also be a macroporagen; rather, if the implantable device comprises a macroporagen that is a polymer, the implantable device must comprise at least one additional polymer, even if that additional polymer also acts as a macroporagen.

As used herein, by "drug" is meant any type of molecule, or a mixture or complex of molecules that may be administered to a host with the intention of that molecule or mixture having a known bioactive, therapeutic effect on that host. A therapeutic effect may be a stimulatory effect on autologous or allograft cells (e.g., stimulating growth of cells that repair wounds) or an inhibitory effect on pathogenic cells or agents (e.g., inhibiting growth of bacteria or viruses). Thus, a drug shall include, without limitation, an antibiotic, antiseptic, bactericide, antifungal, antimicrobial, a growth factor, a vasodilator, a vasoconstrictor, an angiogenesis factor, a chemotactic factor, a cytokine, a pharmaceutical small molecule, a pharmaceutical biological, an enzyme, an antibody, or a mixture or two or more of the preceding. In some embodiments, the drug is water-soluble.

In some embodiments, the drug is thermostable. By "thermostable" is meant that the drug's activity after heating the drug for at least one minute to a temperature higher than 37° C. is at least 80% or 85% or 90% or 95% or 99% of the activity of that drug at 37° C. For example, a thermostable drug is one that has an activity of at least 80% or 85% or 90% or 95% or 99% of the activity of the drug at 37° C. when the drug is heated for at least one minute, or at least two minutes, or at least five minutes to a temperature that is at least 55° C., or at least 60° C., or at least 65° C., or at least 70° C., or at least 75° C., or at least 80° C., or at least 85° C., or at least 90° C., or at least 95° C., or at least 98° C., or at boiling point, or at the thermal processing point used for drug processing in the device. Some drugs are thermostable (e.g., the thermostable antibiotics described below). For example, thermostable antibiotic drugs include, without limitation, tobramycin, gentamicin, vancomycin, and the cephalosporins. In addition, methods are known for making almost any protein thermostable (see, e.g., Chautard et al., Nature Methods 4(11): 919-921, 2007; Hoseki et al., J. Biochem. 126(5): 951-956, 1999; Liao et al., Proc. Natl. Acad. Sci. USA 83(3): 576-580, 1986; Iwamoto et al., Appl. Environ. Microbiol. 73(17): 5676-5678, 2007).

In some embodiments, the drug is selected based on the need of the pathogen. For example, for periprosthetic infections following an implant, many involve pathogens such as gram-positive organisms such as *Staphylococcus aureus* and *Staphylococcus epidermidis*, both of which are inhibited by tobramycin. Likewise, gentamicin (another antibiotic) will also further inhibit *E. coli*, Enteroacteriaeceae and *Pseudomonas aeruginosa*. Additional antibiotics can be used to address antibiotic resistant strains of these bacteria. For example, vancomycin can inhibit methicillin-resistant *Staphylococcus aureus* (see Cui et al., J. of Bone and Joint Surgery 89(4): 871-882, 2007).

In some embodiments, the drug is either nano- or microencapsulated within a polymer or lipid-encapsulating phase. In this embodiment, the drug is nano- or microencapsulated prior to being added to the uniformly dispersed solid-liquid matrix mixture. For example, lipid microencapsulated drug is commercially available (e.g., microencapsulated tobramycin can be purchased from Maxx Performance, Inc., Chester, N.Y.). Microencapsulation of drugs can also be accomplished using the standard double emulsion methods with degradable polymer encapsulants (e.g., PCL, PLGA, poly (anhydrides), proteins, cellulosics). Of course, the drug may also not be microencapsulated when included within the devices described herein, or the drug may be used as a mixture of dispersed encapsulated and non-encapsulated drug simultaneously in the device. For example, a device may include a first drug (e.g., tobramycin) that is encapsulated and a second drug (e.g., vancomycin) that is not encapsulated.

The polymer used to encapsulate the drug may be chosen based on the desired elution profile of the encapsulated drug. As described below in Example 4, the PCL polymer may be selected to encapsulate a drug with a desired long duration release. In some embodiments, the PLGA may be desired to encapsulate a drug with a shorter duration release. Using these microencapsulation properties, and the properties of the drug itself, the presence of two or more types of drugs within a single implantable device is also contemplated herein (as is the contemplation of two more non-encapsulated drugs within the same implantable device). For example, FIG. 23 is a theoretical schematic contemplating the elution profile of a single implantable device comprising the shorter duration eluting drug 1 and the longer duration eluting drug 2, both as encapsulated or non-encapsulated forms dispersed in the device.

Other polymers that can be used to microencapsulate drugs include, without limitation, specifically, polyvinylpyrrolidone, NaCMC, hydroxypropylcellulose, hyaluronic acid alginate, cellulosics and their alkyl ether derivatives (e.g., HPMC, methylcellulose, ethylcellulose), hyaluronans and their derivatives, alginates and their derivatives, poly(alpha-hydroxy esters), poly(anhydrides), and poly(amino acids).

In some embodiments, the implantable device (or the core thereof) comprises a uniform mixture that includes a poragen. As used herein, the term "poragen" is used to refer to a component that, when added to a mixture is able to dissolve or physically or chemically transform (e.g., degrade) to create water-filled pores (or voids or spaces) in the mixture upon implantation. In some embodiments, the poragen is added to the non-solid dispersed mixture, which is subsequently solidified to form an implantable device, where the presence of the poragen results in water-filled pores in the solidified implantable device.

The size of the pore in the device created by the poragen may vary. For example, the diameter of a water molecule is approximately 0.2 nm (0.2 nanometers). The diameter of a cell (e.g., osteoblast, osteoclast) is approximately 9 µm (9 micrometers). If the pore created by dissolution of poragen molecules (e.g., $CaCl_2$ salt crystal poragens) is smaller than 5 µm, the poragen may be referred to as a micro poragen. In some meobidments, the microporagen is $CaCl_2$. Additional non-limiting microporagens include Calcium sulfate, Calcium carbonate, magnesium carbonate, magnesium chloride, sodium chloride, and potassium chloride. If pores are created by dissolution of a collection or aggregate of poragen molecules (e.g., polyethylene glycol clusters) is larger than 5 µm, the poragen may be referred to as a macroporagen.

Without wishing to be bound by any particularly theory, in some embodiments, an implant may comprise two types of water-soluble poragens, namely a macro poragen and a micro poragen. In the mixture, the two types of poragens (the macro poragen and the micro poragen) are uniformly mixed as both dispersed solids or dissolved molecules in the implant. Accordingly to this non-limiting embodiment, water molecules may enter the implant via a micro pore (i.e., a pore created by a microporagen) by dissolving or degrading the poragen away to leave a void in the implant in place of the poragen. Further such poragen removal creates pores into the implant body. Accessing the implant body, the water molecule would then degrade the other components of the implant outlining the micro pore (e.g., the degradable polymer), creating space sufficient for a cell (e.g., a osteoclast or macrophage) to squeeze through the created pores and enter the implant as a desired osteoconductive mechanism. Depending on mass fraction and chemistry selected for use, this poragen formula accelerates creation of porosity in the device, entry of water, release of drug and entry of host cells.

In some embodiments, the implantable device described herein comprise a thin coating or membrane covering the surface of part or all of the device. This coating provides the ability to release multiple classes of drugs from the described implantable devices with appropriate drug release kinetics.

In some embodiments, the coating is a polymer coating. Note, this thin polymer matrix coating or controlling membrane is unfeasible when using the biodegradable drug carriers as bulk structural material. No commercially available allograft bone graft products available in the United States incorporate an integrated, polymer-controlled, antibiotic release scheme for arthroplasty or revision surgeries (Brooks et al., Antimicrobial Medical Devices in Preclinical Development and Clinical Use, in "Biomaterials Associated Infection," T. Moriarty (ed), Springer Science, New York 2013). The degradable polymers used in the devices described herein can sustain antibiotic release for a longer period of time at higher drug concentrations above the MIC, depending upon the polymer molecular weight and composition (see methodology and results in Sevy, J. O., et al., Assay method for polymer-controlled antibiotic release from allograft bone to target orthopaedic infections—biomed 2010. Biomed Sci Instrum. 46: p. 136-41, 2010). By combining polymers with varying degradation properties in a single drug-releasing device, the composite devices described herein allow the incorporation of multiple drugs to be segregated into particles and released according to the epidemiology and etiology of infection. Importantly, as they comprise less than 50% of the mass of the device, and in preferred embodiments, less than 30% by mass, these degradable polymers are able to not only control drug release, but are also able to resorb quickly enough to avoid interference with host bone in-growth.

In some embodiments, the device coating is a bone coating. For example, morselized bone (e.g., either synthetic or allograft bone) may be heated and then applied to a newly hardened composite device. By heating the bone, the bone becomes hot, slightly melting the polymer surface and allowing the bone granules to embed firmly into the surface of the polymeric membrane on the device surface. The composite device can be embedded with different sized fragments of heated bone, so that the larger fragments will coat the device, and the smaller fragments will also coat the device, filling in gaps between the larger fragments on the device surface. In this manner, the entire surface of the device is coated with bone to yield a solid "crust" that is also wettable in water and microporous. In some embodiments, the bone used to coat the device is synthetic bone. In some embodiments, the bone used to coat the device is ProOsteon processed coralline bone (e.g., ProOsteon 500R bone, Biomet, Warsaw, USA). In no embodiments is this bone coating water-impervious.

In some embodiments, the device described herein is osteoconductive. By "osteoconductive" (or osteoconduction) is meant that the device serves as a substrate to promote new bone growth by the patient's own native bone forming processes. In osteoconduction, the patient's osteoblasts at the margin of the device utilize the device as a framework to spread and generate new proteinaceous matrix for new bone formation. By utilizing macroporagens, microporagens, or both macroporagens and microporagens, the devices described herein provide sufficient porosity to allow and even promote ingrowth of the patient's own cells, while still retaining the structural integrity of the device long enough to serve as a scaffold while the patient's new bone is being generated. In some embodiments, the implanted device is eventually completely replaced by the patient's own cells and tissue.

In some embodiments, the predominant component of the uniform mixture of the implantable device is bone. In other words, if the uniform mixture includes polymer, bone, a drug, the bone is present, by weight, in an amount greater than the amount in which the polymer is present and the bone is present, by weight, in an amount greater than the amount in which the drug is present. In some embodiments, the bone is present in an amount that is greater than the combined amounts of the other components in the uniform mixture. In some embodiments, the bone is present in an amount that is 1.25 times, or 1.5 times, or 1.75 times, or 2 times greater than the amount of the other components in the uniform mixture, either individually or in combination. In all embodiments, the mass fraction of bone exceeds the mass fraction of total polymers present.

The implantable devices described herein are implanted into a patient needing joint or bone surgery. The patient may have a defective bone (e.g., broken bone), a defective joint (e.g., injured or arthritic joint), or may have an infection at the site of a bone or a joint (e.g., if the patient had previously had a joint or bone surgery). In some embodiments, when the implantable device is implanted into the patient, no infection of the implanted device and/or no infection at the site of implantation is observed for at least six weeks following the implantation of the device. In some embodiments, when the implantable device is implanted into the patient, no infection of the implanted device and/or no infection at the site of implantation, is observed for at least eight weeks, or at least ten weeks, or at least twelve weeks, or at least fourteen weeks, or at least sixteen weeks following the implantation of the device.

The patient into whom the devices described herein is typically a human patient; however, any vertebrate animal may be a patient. Accordingly, a patient may be a domesticated animal (e.g., cow, horse, goat, sheep, pig, or chicken), an exotic animal (e.g., non-human primate (e.g., chimpanzee), elephant, turtle, tortoise, ostrich), or a pet (e.g., cat or dog). The patient may also be referred to as a host.

In various aspects, the invention provides methods of treating and/or preventing infection in patients in need of a bone or joint surgery by implanting the implantable devices described herein into the patient.

In various aspects, the invention provides methods for manufacturing the implantable devices described herein. The following examples are provided which are meant to illustrate but not limit the invention described herein.

Example 1

In various embodiments, some of the implantable devices described herein are generated by following the manufacturing protocol set forth in this Example 1. This example sets forth the manufacturing protocol for four different devices (referred to below as Formulation 1, Formulation 2, Formulation 3, and Formulation 4). Each formula listed in this Example 1 will make between ten to twelve 2 mm×2 mm×6 mm croutons.

For this manufacturing protocol, the following materials and equipment will be used:

Materials:
ProOsteon® 500R synthetic bone (Biomet, Warsaw, Ind.) sieved to >150 µm and <425 µm
PCL (polycaprolactone) (Mn=10 kDa; Sigma #: 440752)
PEG (polyethylene glycol) (20 kDa; Sigma #: P2263)
PLGA (poly(lactic-co-glycolic) acid) 50:50 (IV=0.55-0.75 dL/g; Lactel #: B6010-2P Lot A10-122)
Acetone
Tobramycin (Research Products Int'lt #: T45000-1.0) or Microencapsulated Tobramycin (Maxx Performance) or any other thermostable drug of interest
Weigh boats
Spatulas (2×)
Slide Molds
Silicone Isolators
Mortar and Pestle Equipment:
Digital control hot plate with external temperature probe
Thermomixer
Scale The components of each formulation of implantable device is set forth below in Table 1.

TABLE 1

|  | Formulation 1 | Formulation 2 | Formulation 3 | Formulation 4 |
|---|---|---|---|---|
| PCL (10 kDa) | 135 mg | 135 mg | 42.8 mg | 42.8 mg |
| PEG (20 kDa) | 15 mg | 15 mg | 21.4 mg | 21.4 mg |
| PLGA 50:50 (0.55-0.75 dL/g) | 0 | 0 mg | 85.5 mg | 85.5 mg |
| $CaCl_2$ (<250 µm) | 0 | 22.2 mg | 22.2 mg | 22.2 mg |
| Tobramycin | 55 mg | 55 mg | 55 mg | 55 mg |
| ProOsteon® 500R >150 µm and <425 µm) | 350 mg | 350 mg | 350 mg | 350 mg |
| ProOsteon® Surface Coating | No | No | No | Yes |

Figure 1C:
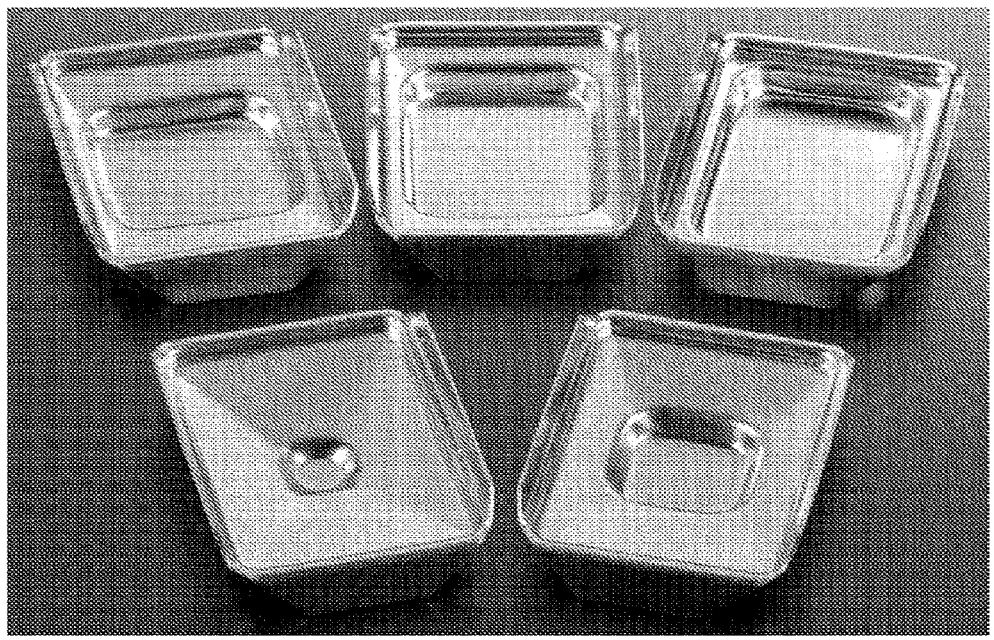
FIGS. 1C and 1D are photographs showing non-limiting examples of slide molds (FIG. 1C) and silicone isolators (FIG. 1D) that can be used to generate the implantable devices of the size and shape described herein. Notet that the examples of specific molded sizes and morphologies shown in these
Figure 1D:
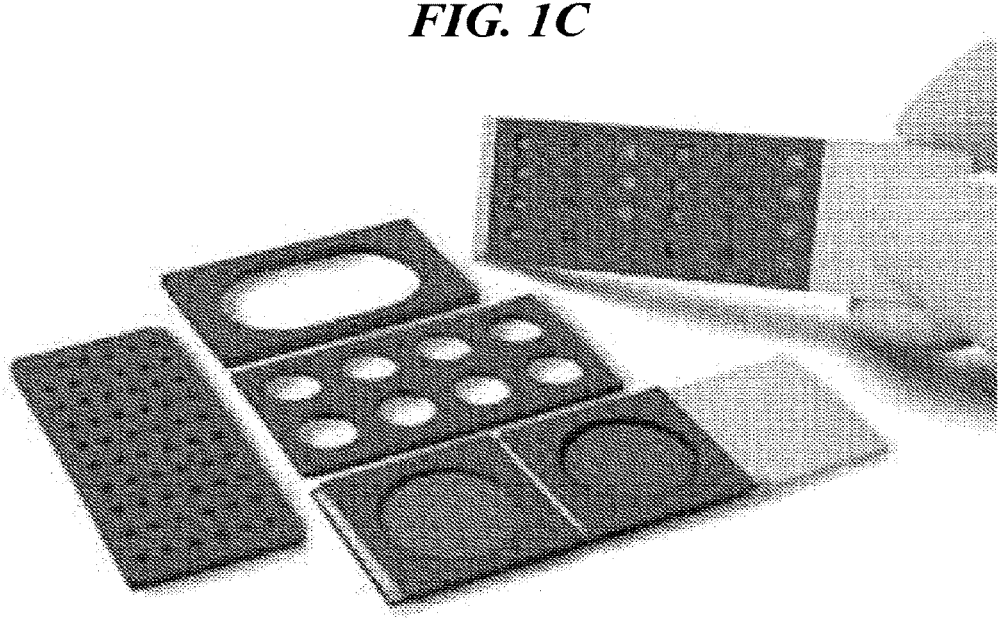

Protocol:
1. Set heat plate to 75° C.
2. Adhere silicone isolator to the bottom of a non tissue culture treated petri dish and place on the hot plate. Note: Packing the silicone mold while warm is necessary to prevent the implant from hardening too quickly.
3. Morselize Bone Void Filler ProOsteon® with mortar and pestle.
4. Sieve the morselized bone to isolate particles larger than 150 µm but less than 425 µm.
5. Evaluate under dissecting scope using a micrometer to ensure consistency.
6. Weigh out ProOsteon®, polymers, and Tobramycin according to above table.
7. Suspend PLGA 50:50 into 400 µl of acetone in a microcentrifuge tube and allow to mix at 37° C. and 1400 rpm for ~15-30 minutes or until completely dissolved. Note that PLGA, in some embodiments, must be solubilized before being mixed with other polymers over heat. The heat will then evaporate the PLGA solvent (in this case acetone) away.
8. Place metallic slide mold on the 75° C. heat plate. FIG. 1C shows an image of a non-limiting slide mold that can be used in this method.
9. Put PCL and PEG in slide mold on 75° C. heat plate for approximately 15 to 30 minutes, until polymer is consistently melted.
10. Stir polymer mix with spatula until thoroughly mixed.
11. Add morselized ProOsteon® 500R, $CaCl_2$, and Tobramycin antibiotic powder to melted polymer mixture and mix well using the spatula.
12. Pipette the PLGA solution over the bolus composite mixture and continue to mix with a spatula.
13. Using the spatulas, fill each space in the silicone isolator with the polymer/ProOsteon®/drug molten mixture and compress. Scrape excess polymer before it solidifies. FIG. 1D is an image of some non-limiting silicone isolators that can be used in this method.
14. After silicone isolator is filled, remove from heat for at least 5 minutes prior to releasing the implants from the mold.
15. Using a spatula carefully pry the implants from the silicone mold.

The fabrication method is schematically depicted in FIG. 1A.

For Formulation 4 (e.g., to increase host bone contacts with the crouton and promote bone healing and growth):
1. Place morselized ProOsteon® in one of two slide molds, segregating the ProOsteon® by size: A) Coat first with ProOsteon® sieved to >150 µm and <425 µm B) The second coating, used to fill in the gaps and coat the polymer surface, should possess a size of <10 μm.

2. Place each slide mold containing ProOsteon® on the 75° C. heat plate.

3. Use a clean spatula to roll the croutons made in the first part of this SOP in the warm ProOsteon® in each slide mold (first the larger particulate and then the smaller) allowing the crouton to cool in between the slide molds The fabrication method for Formulation 4 is schematically depicted in FIGS. 1A-1B.

For Individual Implantable Device Quality Assurance Tests, the following protocol is followed.

First, a device from each batch is measured to ensure it is within +/−5% of a width and height of 2 mm, +/−0.15 mm of a length of 6 mm, and +/−a weight of 37.5.

The device is also examined under a dissecting scope to look for smoothness. Implantable devices, as described herein, should not have major voids.

The device is also examined under a dissecting scope to look for squareness. Implantable devices, as described herein, should have right angles. For example, an implantable device should have crisp 90° angles.

Scanning electron microscopy (SEM) images are taken of one device from each batch to ensure consistency of blended material of the device. FIG. 2A shows the surface of a formulation 1, formulation 2, or formulation 3 device. FIG. 2B shows the surface of a formulation 4 device.

Scanning electron microscopy (SEM) images are taken of one device from each batch after 1 day following release of the device from the silicone mold to ensure porosity of the device.

Finally, the device will be subjected to a compression mechanical test. This test is schematically depicted in FIG. 3.

Example 2

ProOsteon® 500R, a clinical grade commercial hybrid coralline inorganic bone void filler (Biomet, USA) was morselized using a mortar and pestle. Morselized granules were sieved and particles between 150 and 425 μm were included in all subsequent fabrication steps. Polycaprolactone 10 kDa (PCL, Sigma 440752) was mixed with various concentrations of polyethylene glycol 20 kDa (Sigma P2263) (see formulations in Table 2) and heated at 75° C. in a metallic tray until the polymers completely melted to blend (see FIG. 1A).

TABLE 2

| Group | PCL | PEG | Synthetic bone | Tobramycin |
|---|---|---|---|---|
| 1 | 142.5 mg | 7.5 mg | 350 mg | 55 mg |
| 2 | 147 mg | 3 mg | 350 mg | 55 mg |
| 3 | 150 mg | 0 mg | 350 mg | 55 mg |

Table 2 shows the different material compositions of antibiotic-eluting molded polymer-controlled bone graft devices used in this Example. Ratios of polymers PCL and PEG were changed as the matrix and poragen, affecting the drug-releasing effects.

Morselized ProOsteon granules (approximately 60% w/w, Table 2) and solid tobramycin sulfate (Research Products International T45000-1.0; 10% w/w, Table 2) were then well mixed in a metal tray with a metallic spatula into the molten polymer mixture. Subsequently, the polymer-coralline substrate-drug composite molten mixture was compressed into a silicone mold (Grace Biolabs, dimensions 2 mm×2 mm×6 mm). Each mold had an adhesive backing and was adhered to the surface of a petri dish. A different mold adhered to a different petri dish was used for each formulation prepared.

All molds were cleaned with acetone and 70% ethanol and allowed to dry between batches. Each Petri dish containing a mold was placed on the hot plate (pre-heated to 75° C.) prior to packing. After all of the 2 mm×2 mm×6 mm rectangles of the silicone mold were filled with molten composite, the fragments were removed from the heat and allowed to cool in the mold for a minimum of 5 minutes up to 30 minutes at room temperature. Subsequently, a metal spatula was used to pry the molded fragments from the mold. Each device was placed in a microcentrifuge tube and protected from light until use. Devices were either used the same day (control for shelf life studies) or stored according to the designated conditions for the shelf life study (Table 3).

Note that the implantable devices described in this Example 2 did not contain any microporagen and were not coated with a thin layer of warmed, morselized ProOsteon (compare to formulation 4 in Example 1). However, note that in the Cohort 7 animals in the first in vivo study (see FIGS. 15A-18), the device made according to Group 2 formulation set forth in Table 2 above were dip coated in a PCL acetone solution (acetone containing 60 mg/ml PCL) and allowed to air dry prior to sterilization with ethylene oxide and implantation.

Table 3 shows the summary of mechanical properties for molded device fragments containing antibiotic and polymer to those with only polymer (no drug).

TABLE 3

| | | Direction 1 | | Direction 2 | | Direction 3 | |
|---|---|---|---|---|---|---|---|
| | | Rate 1 (0.5 mm/min) | Rate 2 (2.0 mm/min) | Rate 1 (0.5 mm/min) | Rate 2 (2.0 mm/min) | Rate 1 ((0.5 mm/min) | Rate 2 (2.0 mm/min) |
| E (MPa) | Drug | 187.72 (79.49)* | 226.19 (30.33) | 180.35 (10.85) | 206.65 (52.64) | 558.13 (194.71) | 505.97 (151.96) |
| | No Drug | 22538 (67-57) | 217.46 (32.63) | 210.15 (42.19) | 203.58 (39.76) | 450.01 (139.29) | 514.88 (171.182) |
| σ (MPa) | Drug | 12.26 (1.97) | 13.06 (1.48) | 13.33 (1.12) | 14.71 (1.06) | 10.48 (1.76) | 10.48 (1.76) |
| | No Drug | 12.92 (3.03) | 13.42 (1.51) | 15.11 (2.13) | 14.78 (3.29) | 12.03 (2.15) | 13.99 (1.10) |

*Values reported as "Mean (Standard Deviation)"

Figure 4A:
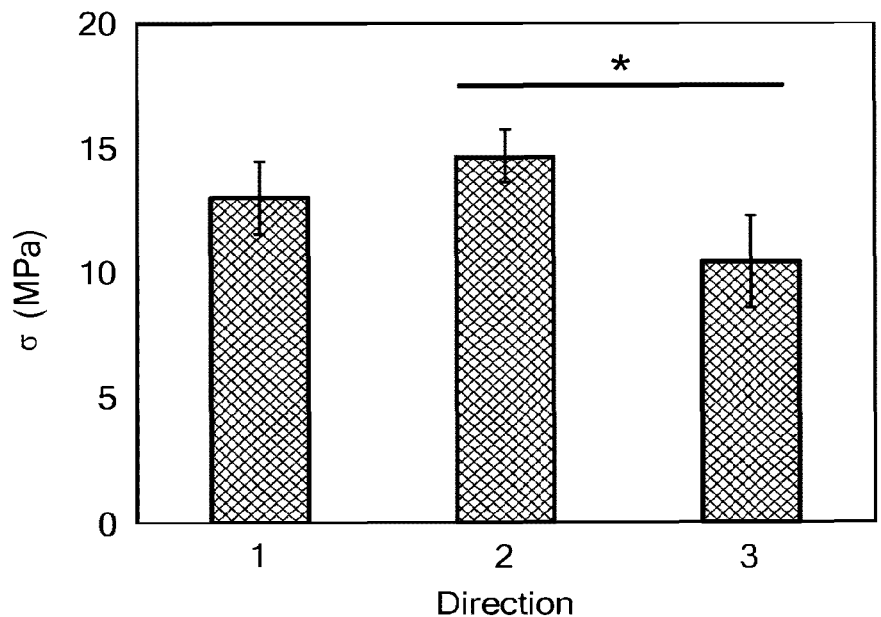
FIGS. 4A and 4B are bar graphs showing a summary of molded composite mechanical characterization plotted as (A) ultimate stress (r) or (B) Young's modulus (E) versus the three compression directions (see FIG. 3B). Load rate and the presence/absence of drug had no significant effect on material properties, so all data points were combined in the graphs shown in FIGS. 4A and 4B. Direction 3 had significantly lower ultimate stress ($*p<0.05$) than Direction 2, and a significantly higher Young's modulus ($**p<0.001$) than Direction 1 and 2, representative of a transversely isotropic material.
Figure 4B:
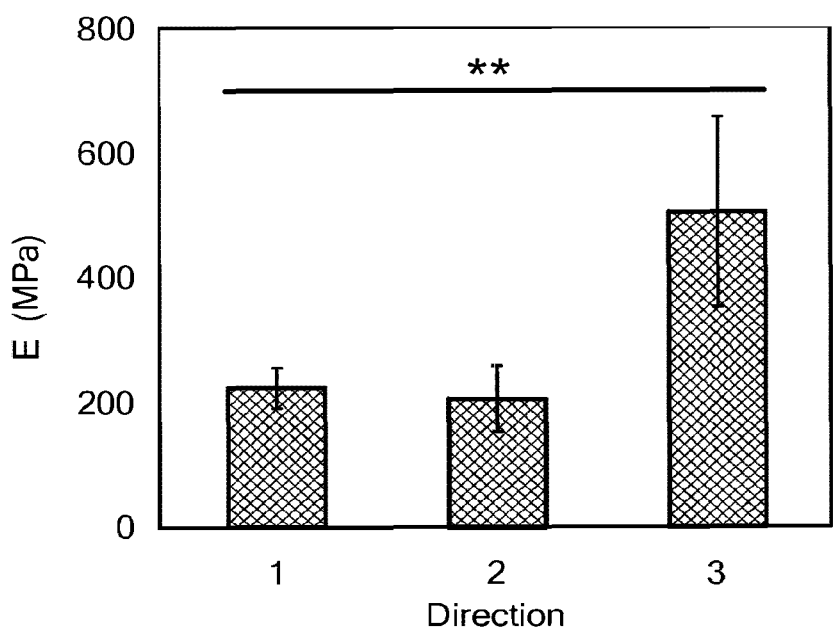

Compression tests were performed at two load rates and three test configurations (See FIG. 3). Only one direction had a significant effect on the mechanical properties with Direction 3 resulting in a higher modulus and lower ultimate stress (See FIGS. 4A and 4B).

Device Quality Control Tests

The following quality control analyses were performed on all individual bone void filler (BVF) molded fragments: (1) size measurements including length, width, and height (spec: <10% deviation from standard), (2) weight measurement (spec: <5% deviation from standard), [1] qualitative shape assessment (spec: no visually apparent large defects), and (4) qualitative smoothness assessment (i.e., three areas on different surfaces). Visual inspection was performed on a dissecting microscope at 10× magnification. In addition, the following quality control tests were performed on batches intended for in vitro preclinical testing: (1) SEM images at 5×, 50×, and 500× were taken to evaluate for consistent texture and (2) mechanical tests were performed as outlined below.

Culture of S. aureus ATCC Strain 49230

ATCC Staphylococcus aureus strain 49230 was struck from a tryptic soy broth (TSB) glycerol −80° C. freezer stock onto a blood agar plate (5% sheep blood, BD Biosciences, USA) and allowed to grow up to 3 days at 37° C. For all Kirby-Bauer/ZOI tests, individual colonies were picked into sterile saline solution with an individual sterile cotton swab from a blood agar plate that was no more than 3 days old. A solution of approximately $5\times10^8$ CFU/ml in saline was made immediately prior to use in the experiment using a nephelometer (BD Biosciences) for use in all Kirby-Bauer experiments. All liquid cultures of S. aureus were grown in Tryptic Soy Broth (TSB, BD Bioscience)+10% fetal bovine serum (FBS). Cultures were assessed for absorbance using spectrophotometry (OD=600 nm) to determine growth curves.

Drug Release Studies

Devices (n=5) were tested for drug release. To do this, tobramycin was released from each device into 3 ml of phosphate buffered saline pH 7.4 (PBS: Fisher Scientific). At each time point (24 hours and each week through the remainder of the experiment), the complete release volume was drawn off and replaced with fresh PBS. Kinetics of release from each formulation were assessed with a previously reported 96-well fluorescent assay (see Davidoff et al., Biomed. Sci. Instrum. 46: 184, 2010; Sevy et al., Biomed Sci. Instrum. 46: 136, 2010) based on o-phthaldehyde (OPA, Sigma Aldrich, St. Louis Mo.) labeling of tobramycin primary amines after drug release.

Briefly, 75 μl of each release sample was added to 75 μl of isopropanol in wells within black-masked 96-well plate (Fisher Scientific, Pittsburgh, USA). 150 μl of OPA working solution (50 μl of OPA stock solution in 1 ml of 0.5 M potassium borate buffer pH 10.5) was added to each well and incubated for 30 min prior to assessing the fluorescence of the tobramycin/OPA derivative (Biotek spectrophotometer, ex=360 nm, em=460 nm) using Gen5 1.09 software (BioTek, Winooski, Vt., USA). Each cohort contained a certain number of reference samples (n=3, 6, or 9) from which tobramycin was not released over time but instead the entire coating was dissolved in 1 ml of chloroform (Thermo Fisher Scientific, Waltham, Mass., USA) for approximately 5 minutes and 1 ml of water was used to phase extract tobramycin from the polymer solution by vortexing for 30 seconds and then centrifuging at 15,000 rpm for 2 minutes and 30 seconds. These samples were considered 100% release samples and all amounts of tobramycin released over time from coated grafts were normalized to their cohort-matched 100% release value as well as to the unloaded polymer bone control, and reported as a percentage to facilitate direct comparison of release from different polymer formulations.

Additionally, drug in 500 μl release volume was then dried down on a filter paper disc (6 mm diameter) as previously described (Davidoff et al., Biomed. Sci. Instrum. 46: 184, 2010; Sevy et al., Biomed Sci. Instrum. 46 136, 2010). These discs were then placed on a Brain Heart Infusion (BHI) agar plate streaked with $\sim 5\times10^8$ CFU/ml (determined using a nephelometer) S. aureus (ATCC strain 49230) and allowed to grow for 16-20 hours at 37° C. A schematic showing this assay is presented in FIG. 5A. The zone of inhibition (ZOI) around each disc was measured with calipers and reported as an average of replicate samples (n=3-5).

Liquid chromatography-tandem mass spectrometry was used to quantify the release of tobramycin from the bone void filler device. Briefly, internal standards were prepared by adding trichloroacetic acid (TCA) to water to give a concentration of 100 g/l. An internal standard was prepared by dissolving sisomycin in water (25 mg/l). Tobramycin-containing samples or calibrators (20 μl) were added to the internal standard (20 μl) in deep well microtitre plates and then a precipitating solution (100 μl) was added. The plate was sealed with thermosealing film and vortexed for 30 s to disperse the precipitated material. After centrifugation at 800 g for 5 min, the sealed plate was transferred to the autosampler for analysis. High performance liquid chromatography was performed using a Waters 2795 Alliance HT LC system (Waters, Watford, UK). Supernatant (20 μl) was directly injected from the 96-wellmicrotitre plate onto two SecurityGuard C 18 cartridge columns in series, 4.0×2.0 mm, (Phenomenex, Macclesfield, UK). The following solvent conditions were used [where A=water containing 2 mM ammonium acetate, 0.1% (v/v) formic acid, B=methanol containing 2 mM ammonium acetate, 0.1% (v/v) formic acid) and C=A containing heptafluorobutyric acid (10 mM)]: 20% B and 10% C for 0.6 min, step to 100% B for 0.4 min, step back to 20% B and 10% C to re-equilibrate the column. The run time was set to 1.4 min to give a cycle time of approximately 2.5 min injection to injection, allowing a total re-equilibration time of approximately 1.7 min. The column was maintained at 23° C. and the eluent was connected directly to the electrospray probe of the mass spectrometer with no splitting or solvent diversion. A Quattro micro tandem mass spectrometer fitted with a Z Spray ion source was used for all analyses. The instrument was operated in electrospray positive ionization mode and was directly coupled to the HPLC system. System control and data acquisition was performed. Calibration curves were constructed using linear least squares regression and 1/x weighting was used to ensure maximum accuracy at the lower tobramycin concentrations. To tune the mass spectrometer, a solution of tobramycin or sisomycin (1 mg/l) in 50% aqueous methanol containing 2 mM ammonium acetate and 0.1% formic acid, was infused into the ion source, and the cone voltage optimized to maximize the intensity of the $(M+H)^+$ precursor ions for tobramycin or sisomycin (m/z 467.8 and 447.8, respectively). The collision energy was then adjusted to optimize the signal for the most abundant product ions (m/z 163 and 160, respectively). (Keevil B G, Lockhart S J, Cooper D P. Determination of tobramycin in serum using liquid chromatography-tandem mass spectrometry and comparison with a fluorescence polarisation assay. 2003. Journal of Chromatography B, 794: 329-335.)

Mechanical Testing

Antibiotic-loaded implantable device samples were subjected to unconfined uniaxial compression across 3-5 identically prepared 2 mm×2 mm×6 mm rectangular samples, fabricated as described above. Tests were performed on an Instron 5943 mechanical testing system controlled by an interfaced computer.

Compression tests were performed by subjecting samples to a linearly applied load until failure, defined by a 40% decrease in maximum stress. Samples were tested at two load rates (0.5, 2.0 mm/min) selected to represent rates corresponding to walking and running (see Boewemer and Taylor, J. Exp. Bio. 123(1): 383-400, 1986). Samples were also tested along three principal axes to determine anisotropic behavior (see FIG. 3.)

Shelf Life Study

Fabricated devices made were stored in individual microcentrifuge tubes under ambient air. Multiple tubes containing implants for each condition were sealed in plastic bags and stored in the dark at −20° C., 4° C., 25° C., and 55° C. for 24 hours, 1 week, 1 month, and 2 months in all combinations (n=3). Morphology (SEM), mechanical tests, and Kirby-Bauer testing as outlined above were performed on each sample (n=3-5) to determine if storage affected activity of the released antibiotic, mechanics of the device, or accelerated polymer degradation.

Statistical significance was determined ($p<0.05$) using a one-way analysis of variance for all Kirby-Bauer experiments and kinetics experiments. A three-way analysis of variance was performed to assess the effect of direction, rate, and presence/absence of drug on the ultimate strength and Young's modulus of the bone graft samples from compression. Storage and temperature effects on mechanical integrity were evaluated by comparing all specimens to control samples (1 week post-manufacturing stored at room temperature) using a Dunnett's test.

Results

Bone graft (clinically used commercial BVF hybrid coralline product) was morselized and exhibited a median size of approximately 410 µm (n=2) with a substantial size range of 34-1020 µm (data not shown). Less than 5% of the morselized particulate fell outside this size range. It was subsequently, sieved to isolate particle sizes between 150 and 425 µm for inclusion in the antibiotic-eluting BVF composite. Fabricated antibiotic-eluting coralline BVF was produced as outlined in the materials and methods in batches of 10-12 with dimensions of 2 mm×2 mm×6 mm+/−5% for width and height and 1.5% for length as determined by caliper measurements (see FIG. 1). Each fragment was also weighed to find an average weight (data not shown). If the weight of any individual fragment fell greater than 10% outside the average weight, that fragment was excluded from all additional analysis. Regardless of the ratio of the polymer components in each specific batch (See Table 2), the inorganic materials fraction comprised at least 60% of the bulk weight and the drug portion was maintained at approximately 10% w/w. Importantly, fragments extracted from the silicon mold were not friable and were easily handled, having more malleability with increasing PEG content. This protocol was easily scalable and customizable, exhibiting distinct advantages over previous coating/fabrication techniques. Quality control steps including assessments of weight, shape, smoothness, and size for each device as well as SEM and mechanical testing were performed for each batch.

Device homogeneity was assessed via mechanical testing along multiple axes (FIGS. 3A and 3B). While this bone graft was not intended for structural support, but merely as void filler to support host bone regeneration, the structural properties are important to ensure the mechanical quality of grafting and to ensure that drug loading does not compromise graft properties. Devices were mechanically characterized in 3 different directions, at 2 different rates, and with or without the antibiotic (see Table 3).

As Table 3 shows, a three-way ANOVA ($p<0.05$) across all variables showed no significant differences with load rate or between specimens with and without antibiotic. Compressive ultimate stress in Direction 3 was significantly reduced compared to the other directions ($p<0.05$, FIG. 4A), and the elastic modulus of the device tested in Direction 3 was significantly increased ($p<0.001$, FIG. 4B) suggesting that the specimens are transversely isotropic.

Example 3

Figure 5A:
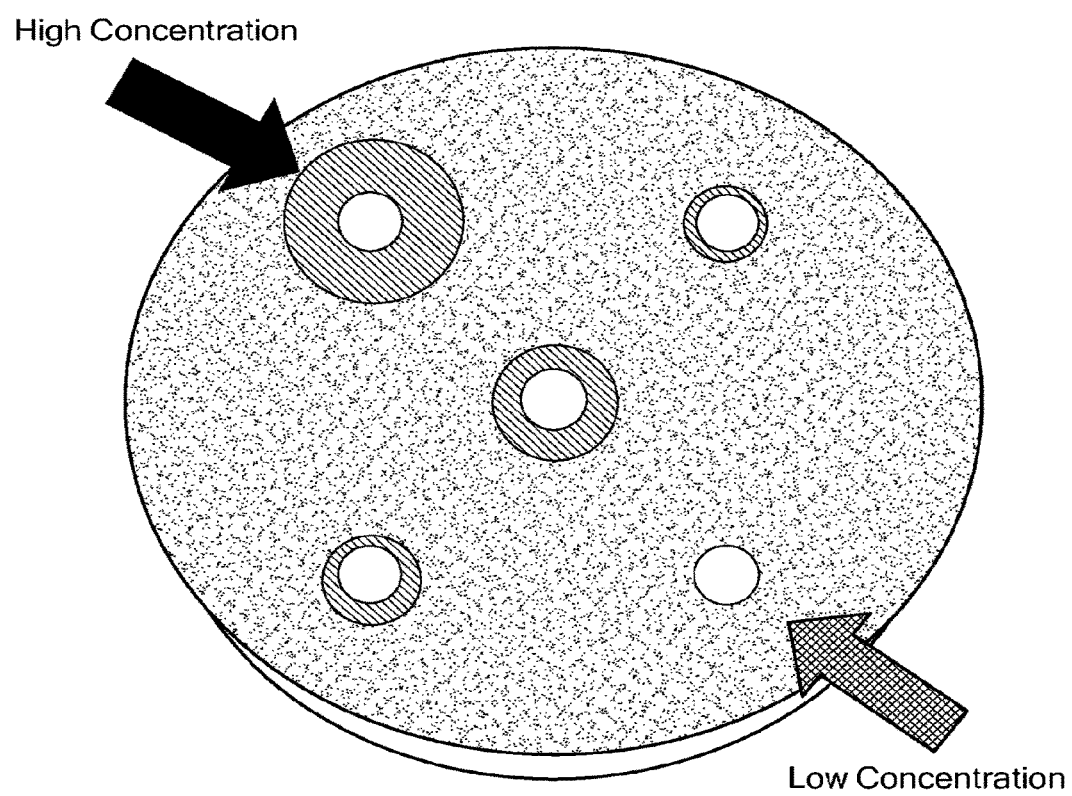
FIG. 5A is a schematic diagram showing the mechanism of the Kirby-Bauer antibiotic sensitivity test or zone of inhibition assay used to assess antimicrobial release from the molded composite bone void filler devices. The diameter of the cleared area in the bacterial lawn is proportional to the amount of drug eluted from molded composite bone void filler devices and dried-down on a recovery disk (e.g., the diameter shown in the black line at the high concentration arrow is approximately three times the diameter of the disk itself).

Next, zone of inhibition studies were performed on the devices. FIG. 5A is a schematic showing the results of a ZOI assay showing a high concentration of antibiotic eluting from a device (upper left) and a low concentration of antibiotic eluting from the device (lower right).

Figure 5B:
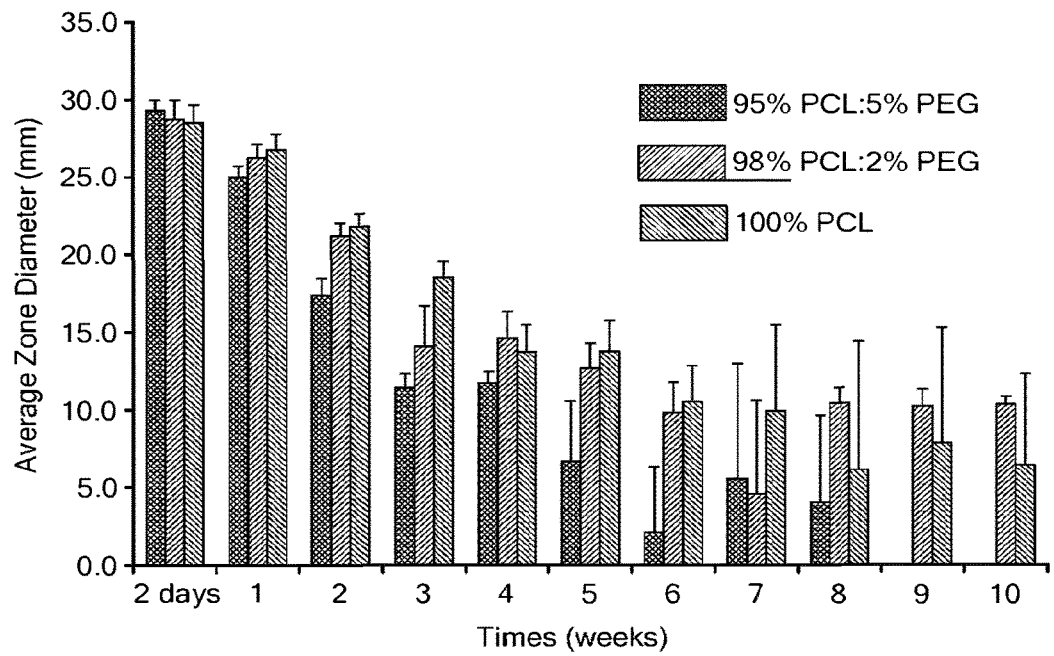
FIG. 5B is a bar graph showing the zones of inhibition of molded composite bone void filler devices comprising tobramycin (10% w/w) and where the minority polymer matrix comprises either 95% PCL:5% PEG (Group 1 Table 2), 98% PCL:2% PEG (Group 2, Table 2) or 100% PCL (Group 3, Table 2) at the indicated weeks of antibiotic release to an in vitro milieu (in PBS). The fabrication containing 100% PCL or 98% PCL: 2% PEG still showed strong killing of bacteria at 10 weeks. Thus, the amount of time it takes to release all the tobramycin can be changed based on the ratio of polymer components with an increase in the PEG component being related to an increase in the rate of tobramycin release, based on the bioactivity.

FIG. 5B shows the results of a zone of inhibition assay on the indicated fabrications. The fabrications tested in these studies were 95% PCL: 5% PEG ratio by weight in the polymer portion of the fabrication which is 27% of the total formulation (the other components being 10% drug and 63% bone) (black bars in FIG. 5B), 98% PCL: 2% PEG ratio by weight in the polymer portion of the fabrication which is 27% of the total formulation (the other components being 10% drug and 63% bone) (crossed bars in FIG. 5B), and 100% PCL ratio by weight in the polymer portion of the fabrication which is 27% of the total formulation (the other components being 10% drug and 63% bone) (diagonally striped bars in FIG. 5B). Generally, FIG. 5B shows that an increase in the PEG component is related to an increase in the rate of tobramycin release. In other words, based on the bioactivity observed, as the amount of PEG in the device increases, the rate of elution of the drug out of the device increases. This observation is consistent with the PEG presence functioning as a macroporagen. As the PEG fraction of the device was increased, the duration of antimicrobial activity decreased (i.e., drug release kinetics were faster, depleting the antibiotic device load more rapidly). Conversely, increasing amounts of PCL in the device prolonged killing durations and indicated that antimicrobial activity may extend beyond 10 weeks (see FIG. 5B and also FIG. 5C).

Another zone of inhibition assay was performed using devices formulated as Groups 1, 2, and 3. Note that Groups 1, 2, and 3 correspond with Formulations 1, 2, and 3 in Table 1 of Example 1 above. Thus, Group 1 implants were made with PCL, PEG, ProOsteon 500R and 10% w/w tobramycin. Group 2 implants were made with PCL, PEG, calcium chloride, ProOsteon 500R, and 10% w/w tobramycin. Group 3 implants were made with PCL, PEG, PLGA, calcium chloride, ProOsteon 500R and 10% w/w tobramycin.

After characterizing the physical properties of fragments from each batch (n=3-5), drug release kinetics were assessed based on the different ratios of PCL to PEG, which were predicted to change the porosity of the matrix and consequently, the rate of drug elution from the antibiotic-loaded implantable devices. The drug release fluorescence assay described above (LOD=0.0625 mg/ml) based on derivatization of tobramycin with OPA was performed to determine drug release.

Figure 5C:
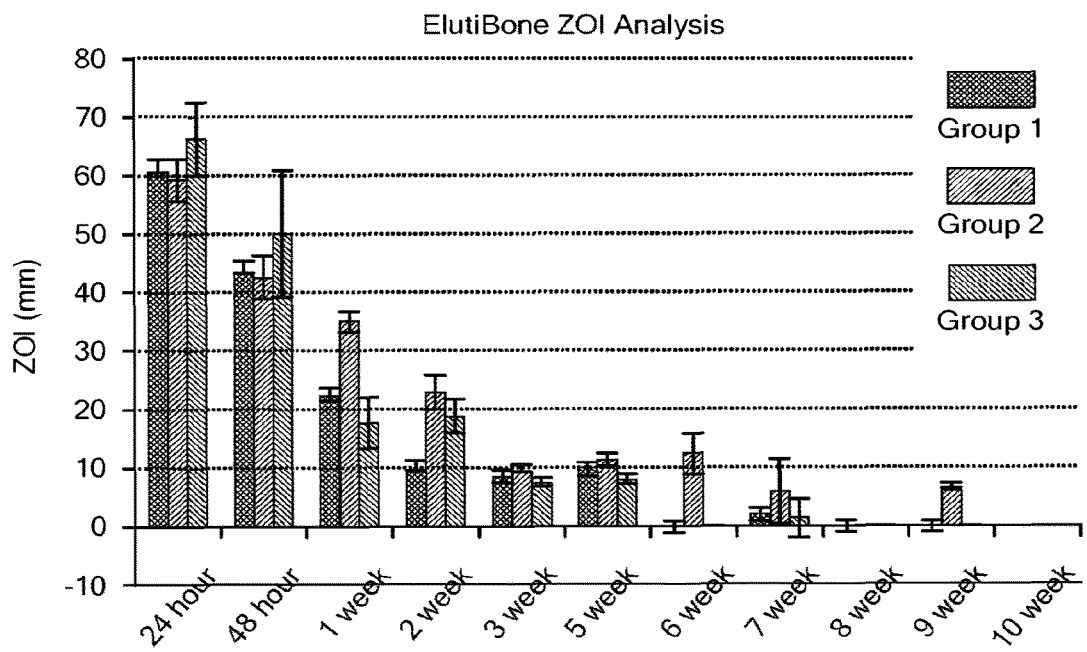
FIG. 5C is a bar graph showing the zones of inhibition of molded composite bone void filler devices at the indicated weeks. Group 1 implants (blue bars) were made with PCL, PEG, ProOsteon 500R and 10% w/w tobramycin (Formulation 1 in Table 1). Group 2 implants (red bars) were made with PCL, PEG, calcium chloride, ProOsteon 500R, and 10% w/w tobramycin (Formulation 2 in Table 1). Group 3 implants (green bars) were made with PCL, PEG, PLGA, calcium chloride, ProOsteon 500R and 10% w/w tobramycin (Formulation 3 in Table 1).
Figure 5D:
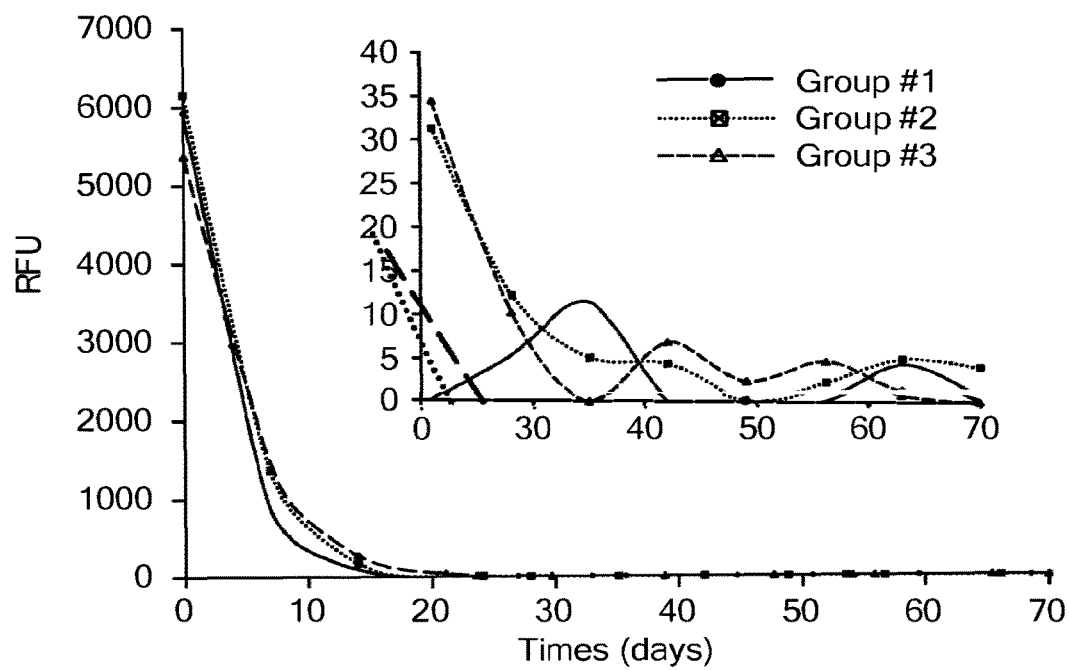
FIG. 5D is a line graph showing the drug release kinetics of the molded composite bone void filler devices tested in FIG. 5B. In Group 1 (black diamond, black line), the polymer fraction of the ElutiBone device is 95% PCL and 5% PEG. In Group 2 (square, dotted line), the polymer fraction of the ElutiBone device is 98% PCL and 2% PEG. In Group 3 (triangle, light gray line), the polymer fraction of the ElutiBone device is 100% PCL and 0% PEG. The inset in FIG. 5D shows the drug release kinetics of the three groups between 20 and 70 hours. Note that Group 1, Group 2, and Group 3 referred to in this FIG. 5D are from Example 2, Table 2.

FIG. 5D shows the drug release kinetics that correspond to the zone of inhibition data shown in FIG. 5B. The inset in FIG. 5D is on an expanded scale (see RFU on vertical axis) and shows that measurable tobramycin release was observed from all three formulations (i.e., Group 1, Group 2, and Group 3 as listed on Table 2 in Example 2 above) throughout the 8-week assay period. Since the drug kinetics assay used cannot specifically determine the exact amount of tobramycin released, antimicrobial activity above the MIC (previously determined to be 4 µg/ml) was assessed using Kirby-Bauer assays (see FIG. 5B). Regardless of the polymer ratio, antibiotic in vitro killing activity against *S. aureus* was observed to at least 8 weeks.

Figure 6:
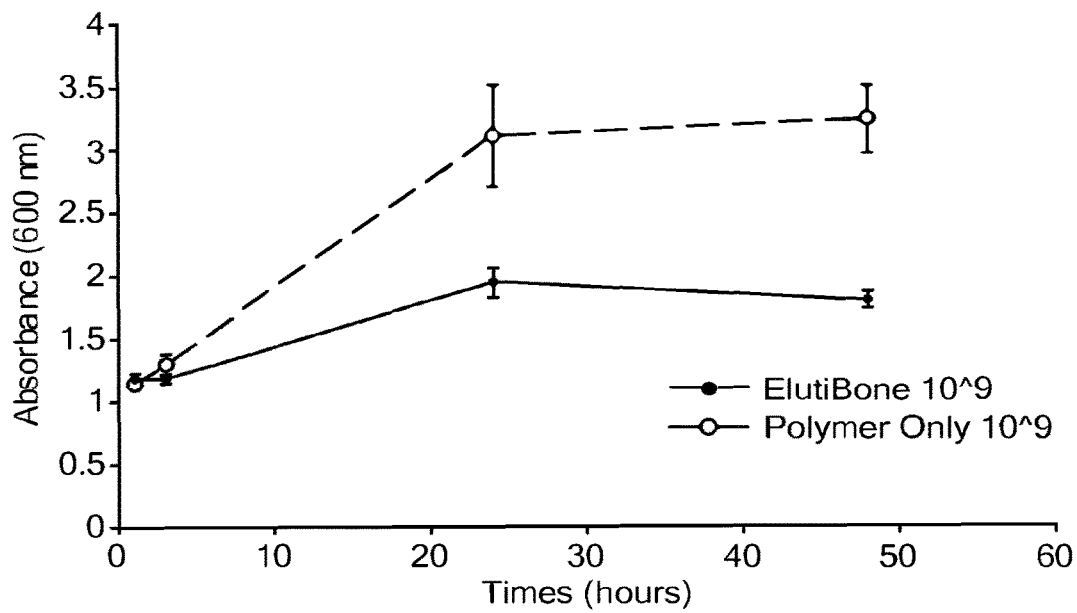
FIG. 6 is a line graph showing the difference in the ability of an antibiotic-containing bone implant (solid line, solid circles) and a no-drug (blank) polymer-coated bone void filler implant (dotted line, open circles) to kill $10^9$ colony forming units (CFU) *S. aureus* American Type Culture Collection (ATCC) strain 49230 in vitro. The data shown in this
Figure 9A:
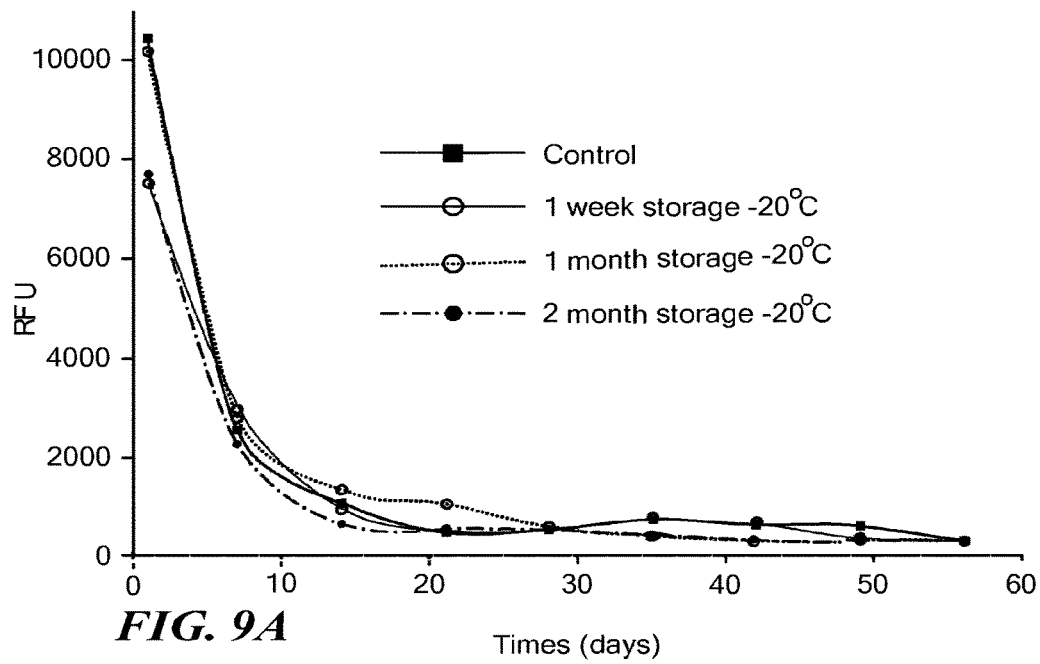
FIG. 9A-9D are line graphs showing the antibiotic tobramycin release kinetics for 8 weeks from molded composite bone void filler devices first stored at −20° C.
Figure 9B:
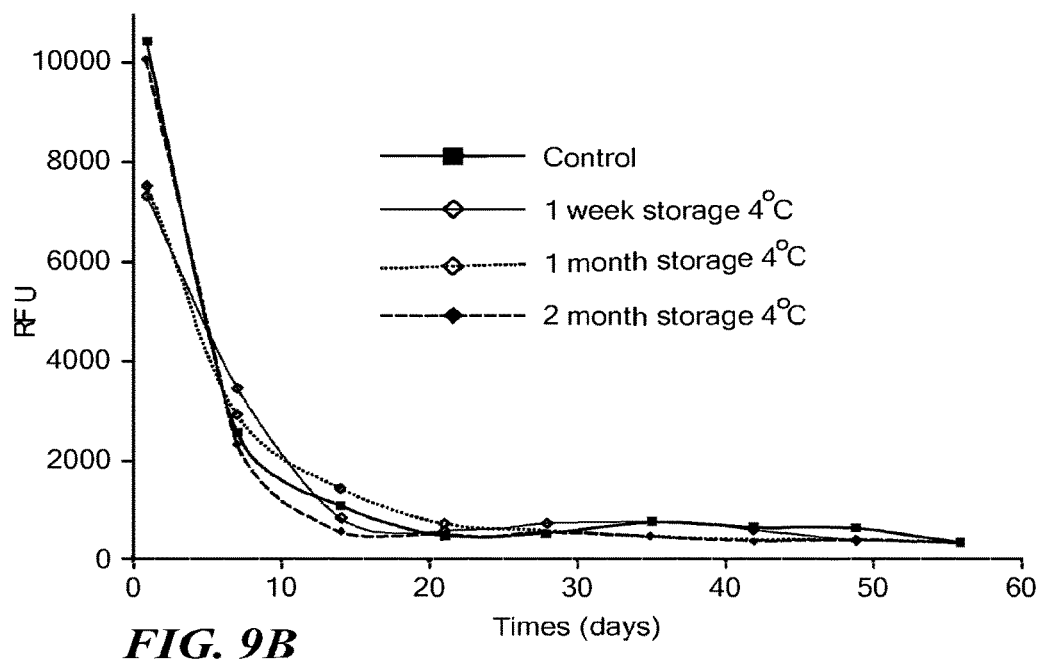
Figure 9C:
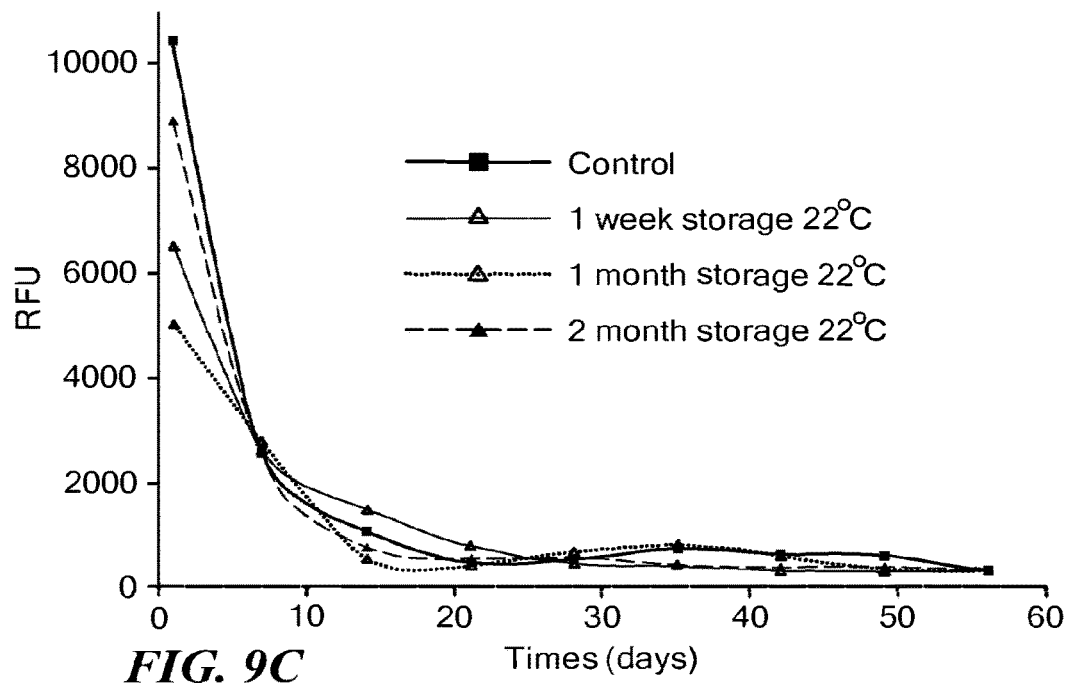
Figure 9D:
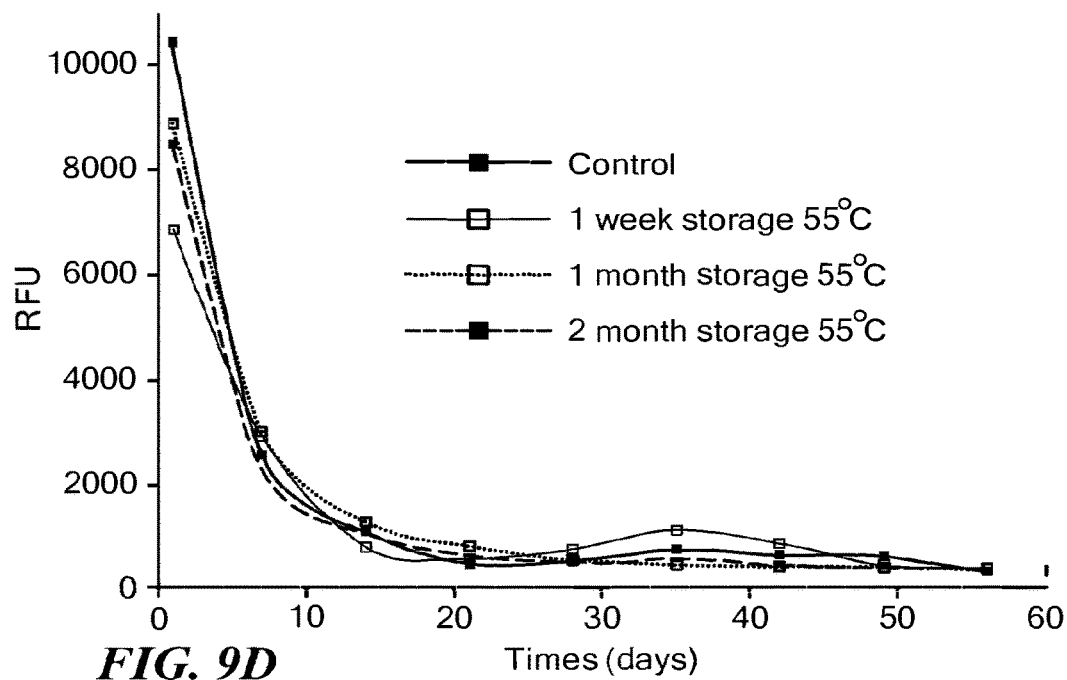

The limit of antimicrobial activity was investigated in vitro based on a modified MIC time kill study (see FIG. 6). The growth rate of *S. aureus* ATCC strain 49230 bacteria, indicated in FIG. 6 by optical absorbance (600 nm) in the presence of antibiotic-eluting BVF composite made according to the Group 2 formulation in Table 2 of Example 2 (closed circle solid line), was compared to non-antibiotic containing controls made according to the Group 2 formulation, but without tobramycin, in Table 2 of Example 2 (open circle dotted line) in vitro (n=3). Even at a high bacterial inoculum ($10^9$ CFU *S. aureus*), the antibiotic-containing BVF composite was able to control bacterial growth over 48 hours. In an analogous experiment where antibiotic-eluting bone graft or its antibiotic-free control were embedded in nutrient agar and $10^9$ CFU *S. aureus* were spread on the nutrient agar surface, bacteria were unable to grow and no colonies were noted on the antibiotic-eluting bone void filler after 48 hours (n=5) (data not shown) while controls showed no such inhibition.

For shelf life studies, briefly, ProOsteon 500R, a hybrid coralline inorganic bone graft biomaterial (Biomet, USA) is morselized with a mortar and pestle and sieved. Particles between 150 and 425 microns are included in all subsequent fabrication steps. PCL 10 kDa (Sigma), a thermoplastic resorbable polymer, is mixed with PEG 20 kDa (Sigma), utilized as a macroporagen, in a weight to weight ratio of 98% PCL and 2% PEG and heated at 75° C. in a metallic tray until the polymers are completely melted to blend. Morselized ProOsteon granules (approximately 60% w/w) and encapsulated or unencapsulated drug (controls) (10% w/w drug content) is mixed as a dispersion into the molten polymer mixture in a metal tray with a metallic spatula. Subsequently, molten antibiotic composite is dispensed into cubic silicone molds (Grace Biolabs, dimensions 2 mm×2 mm×6 mm). After each device is cooled and allowed to set for up to 30 minutes at room temperature, it is placed in a microcentrifuge tube, refrigerated, and protected from light until use. Devices will either be used the same day or stored at −20° C. until sterilized and used. Control devices are fabricated without antibiotic (or using a placebo surrogate solid load, sucrose as control), important for a thorough component safety and integration analysis. Sterilization is done by clinically familiar plasma peroxide treatment prior to implantation.

To assess the stability of antibiotic incorporated in the device, drug elution kinetics and antimicrobial properties were determined after storage at one of four temperatures, protected from light for a designated period of time. Device fragments (n=3-5) were removed from storage conditions at designated time points and assessed for drug release into PBS. SEM imaging was also done at each time point to assess polymer degradation as indicated by amount of coralline bone visible in the images. Dark areas within each SEM were polymer whereas the lighter areas were the inorganic materials as evident from pure polymer or pure bone controls. Based on these images in FIG. 7A-7D, it is clear that more bone is visible after 1 month storage at 55° C.

The aqueous in vitro degradation of the devices was next examined. For these studies, Groups 1, 2, and 3 devices made according to Formulations 1, 2, and 3 (respectively) from Table 1 of Example 1 were tested. SEM images comparing the aqueous in vitro degradation of the antibiotic-releasing composite bone void filler device based on the fabrication Group and the length of incubation in aqueous milieu. (A, E, I) (Time 0), 30 days after the device was placed in liquid milieu (1×PBS) (B, F, J), 60 days after the device was placed in liquid milieu (1×PBS) (C, G, K), and 90 days after the device was placed in liquid milieu (1×PBS) (D, H, L). Group 1 implants were made with PCL, PEG, ProOsteon 500R and 10% w/w tobramycin. Group 2 implants were made with PCL, PEG, calcium chloride, ProOsteon 500R, and 10% w/w tobramycin. Group 3 implants were made with PCL, PEG, PLGA, calcium chloride, ProOsteon 500R and 10% w/w tobramycin. Note the vastly enhanced degradation of the Group 3 formulation compared to Group 1.

Release kinetics of tobramycin in the device devices made according to the Group 2 fabrication in Table 2 of Example 2 were detected by a fluorescence assay based on the derivatization of tobramycin with OPA. As shown in FIGS. 9A-9D, device storage did not result in significant changes to the drug release kinetics from devices made according to the Group 2 fabrication in Table 2 of Example 2. Compare FIG. 9A (devices stored at −20° C.), FIG. 9B (devices stored at 4° C.), FIG. 9C (devices stored at 22° C.), and FIG. 9D (devices stored at 55° C.). After 1 day, the release is indistinguishable from the control devices that were not stored prior to release kinetics testing.

Figure 10A:
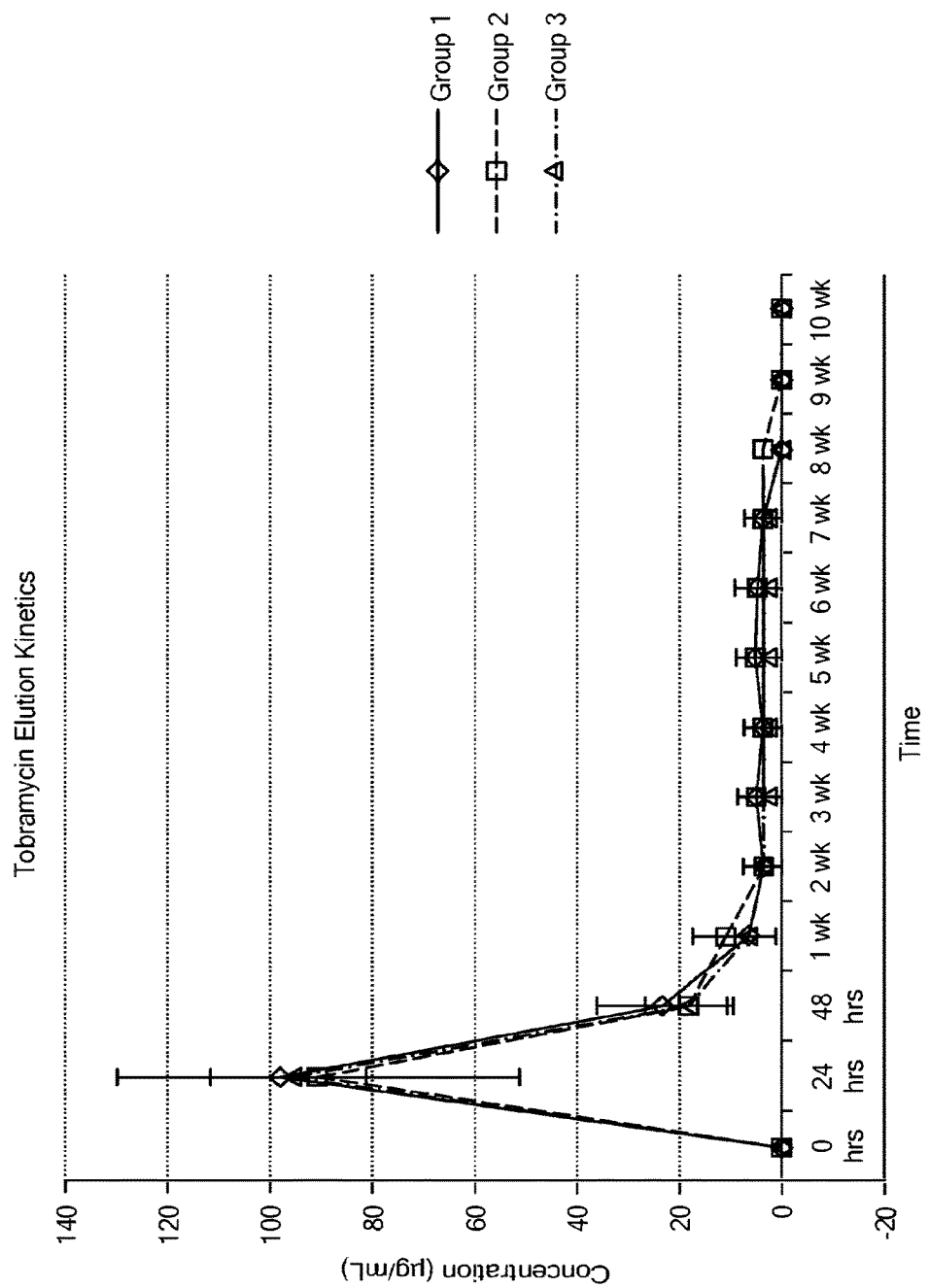
FIGS. 10A and 10B are line graphs showing the amount of tobramycin elution as determined by LC-MS/MS. All three device formulations (1-3) are shown in FIG. 10A with very little distinction noted between the Groups.
Figure 10B:
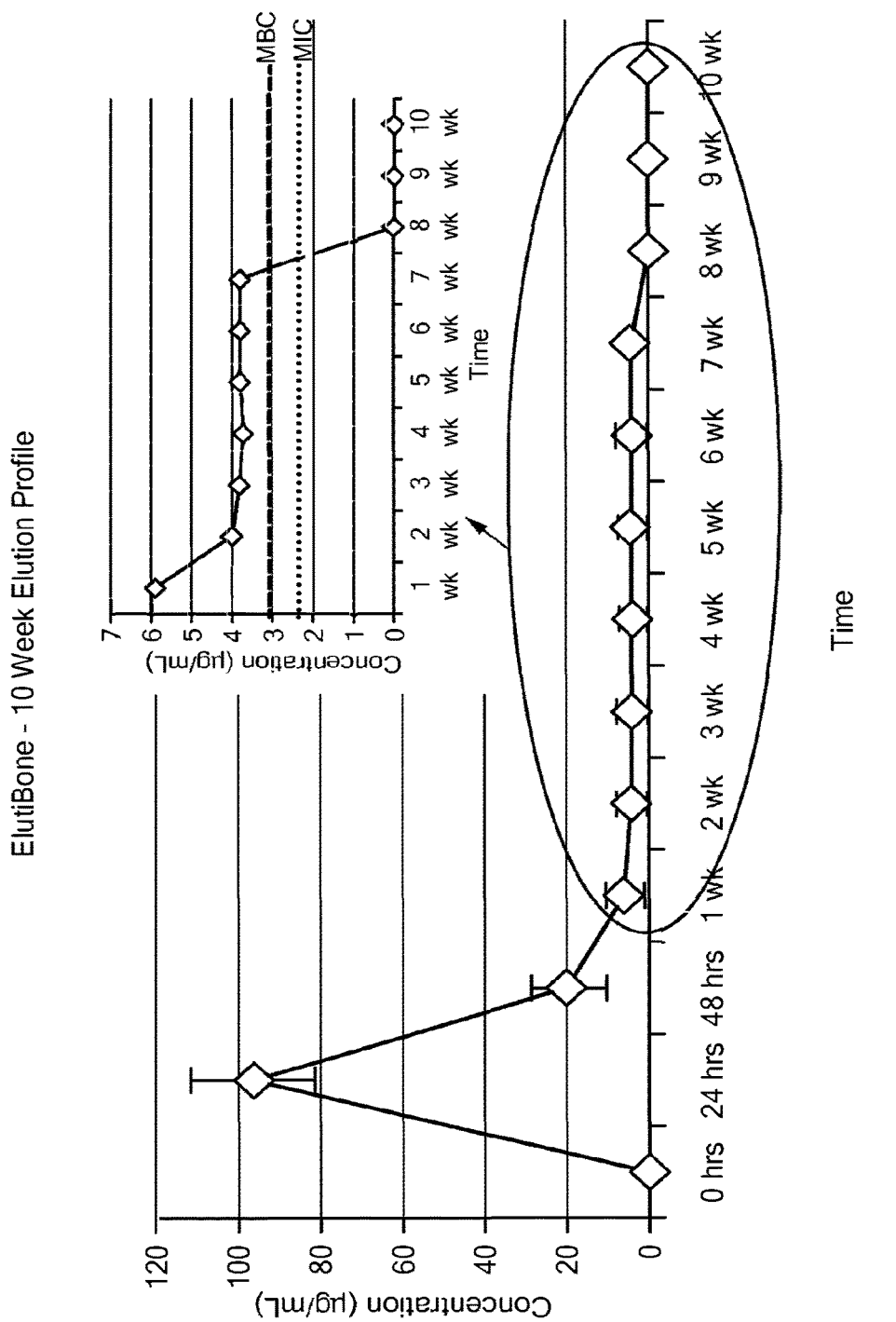
Figure 11A:
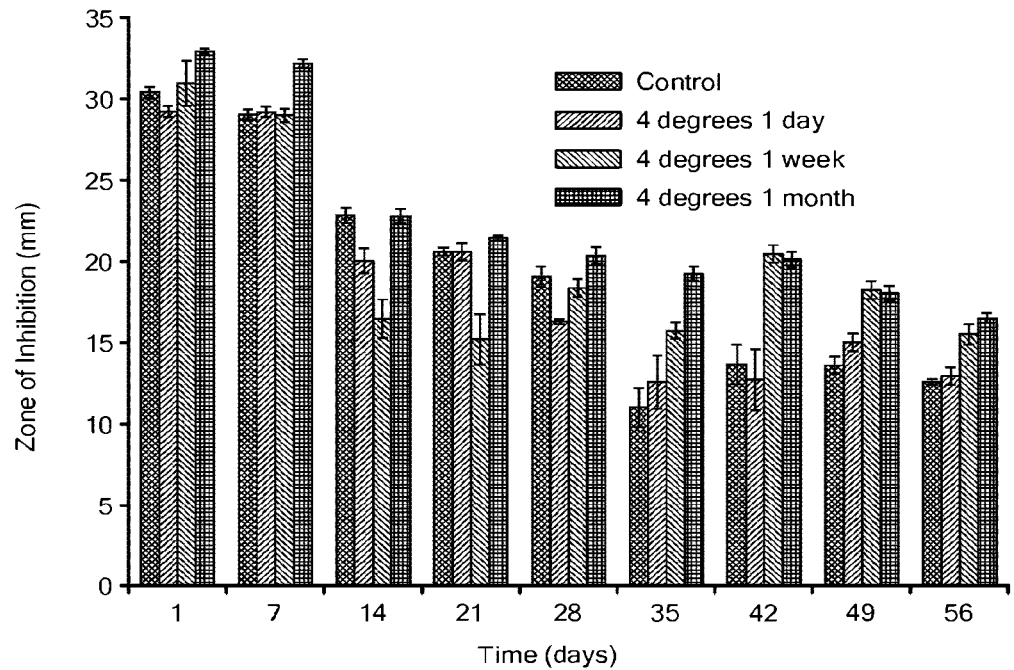
FIGS. 11A-11D are bar graphs showing the antimicrobial activity of released tobramycin as determined by Kirby-Bauer antibiotic sensitivity tests or zone of inhibition assays with S. aureus American Type Culture Collection (ATCC) strain 49230 to 8 weeks. Molded composite bone void filler materials were stored at various temperatures shown for 1 week, 1 month, or 2 months and then antibiotic was released into PBS to 8 weeks. Extended drug release data shown for molded composite bone void filler devices stored at −20° C.
Figure 11B:
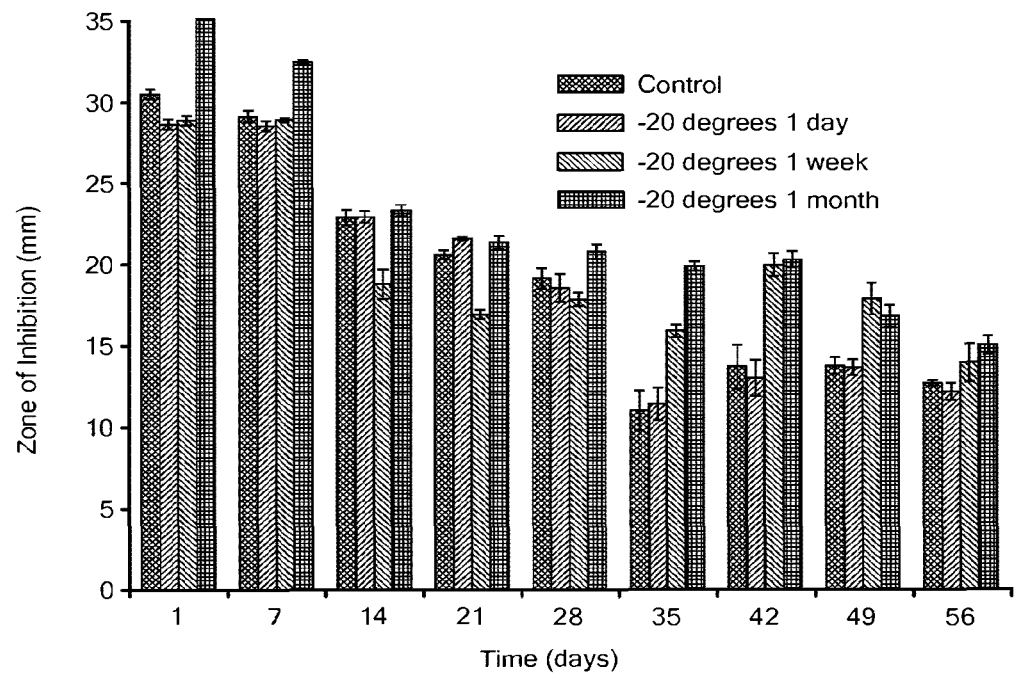
Figure 11C:
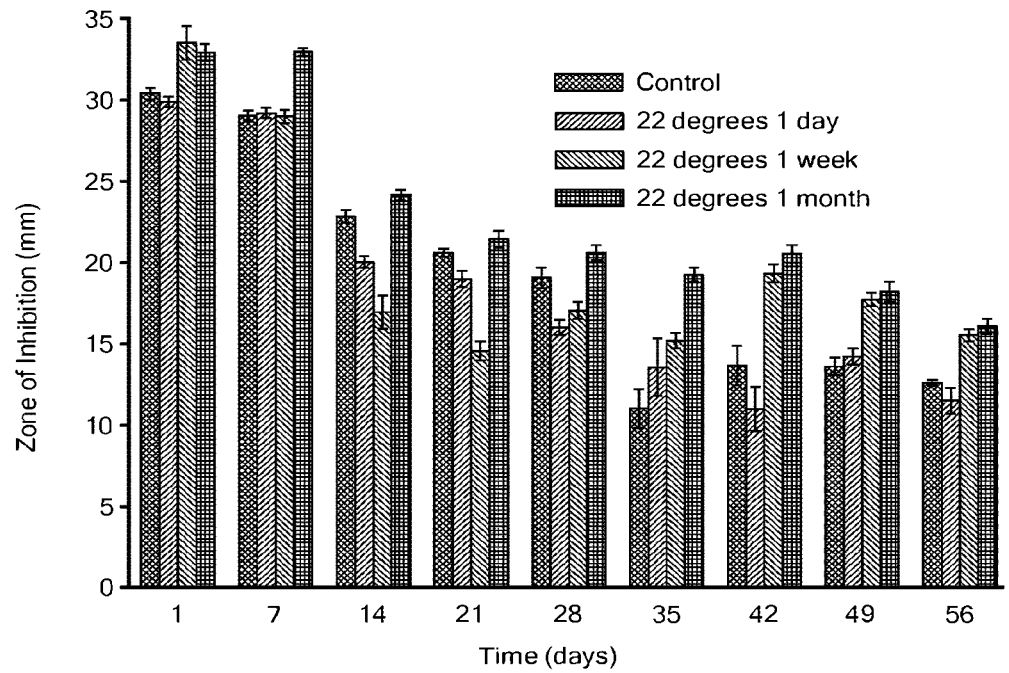
Figure 11D:
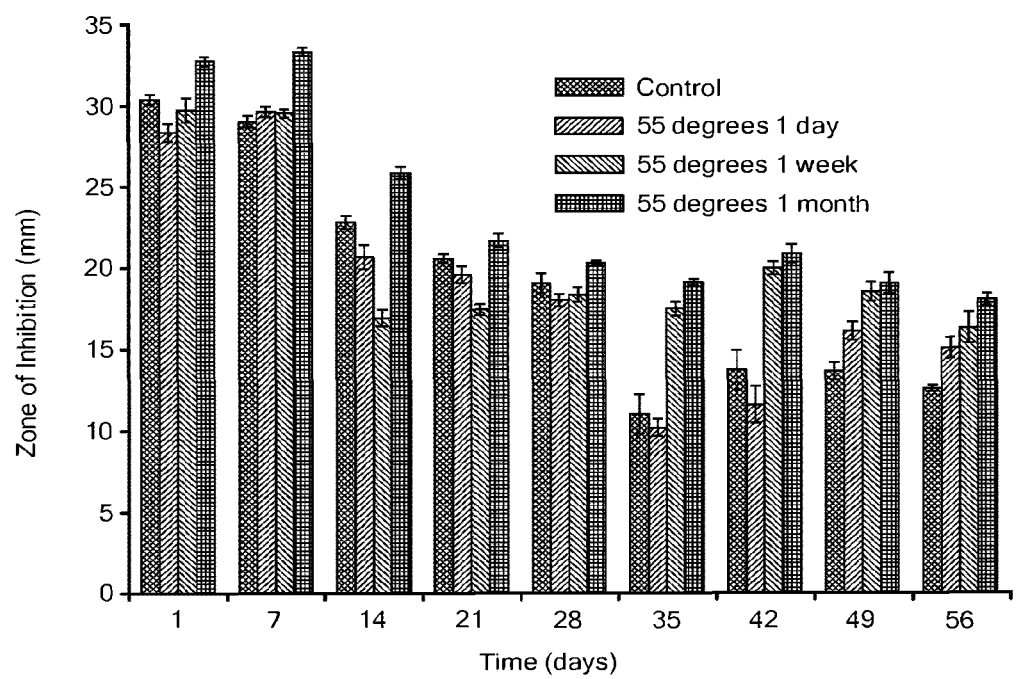

Tobramycin elution was also determined by liquid chromatography-mass spectrometry (LC-MS/MS). FIGS. 10A and 10B show the results from the testing of three device formulations: Group 1 made according to Formulation 1 of Table 1 of Example 1; Group 2 made according to Formulation 2 of Table 1 of Example 1; and Group 3 made according to Formulation 3 of Table 1 of Example 1. As shown in FIG. 10A, very little distinction noted between Group 1, Group 2, and Group 3 devices. FIG. 10C focuses on the Group 3 fabrication, with the inset showing the elution kinetics compared to the minimal bactericidal concentration (MBC) and minimum inhibitory concentration (MIC).

Additionally, antimicrobial activity of tobramycin released from the stored devices made according to the Group 2 fabrication in Table 2 of Example 2, as determined by Kirby-Bauer testing, regardless of the storage time at −20° C., 4° C., 22° C., and 55° C., retained strong activity against *S. aureus* for the entire study duration (FIGS. 11A-11D).

Figure 12A:
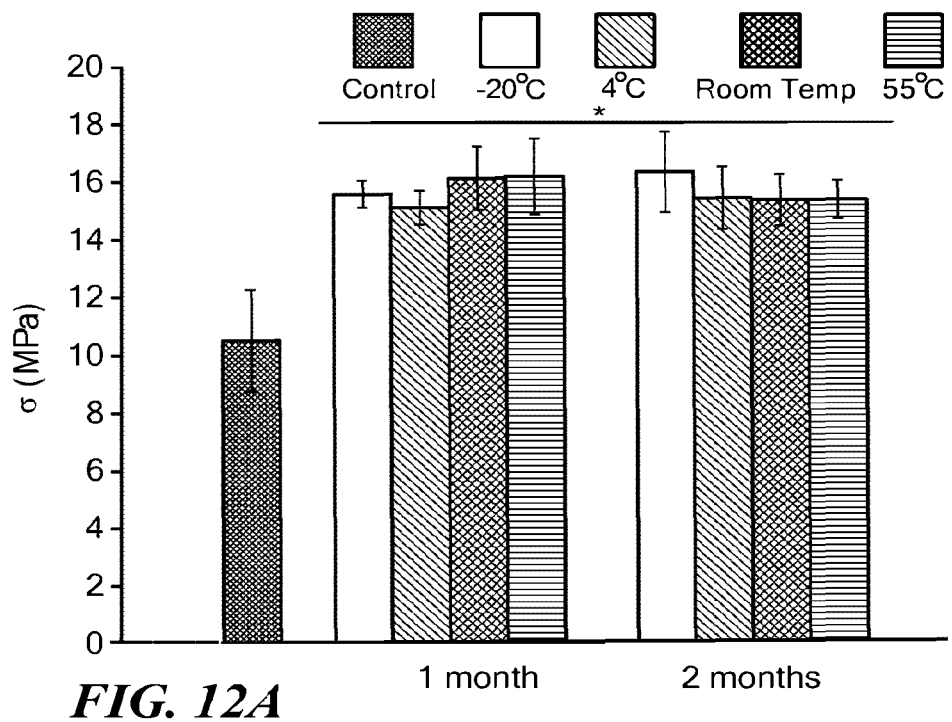
FIG. 12A-12B are bar graphs showing that the shelf life and storage effects on the ultimate stress (FIG. 12A) and modulus (FIG. 12B) of molded composite bone void filler devices tested after 1 and 2 months of storage resulted in higher ultimate stress and moduli than controls stored for only 1 week, but only ultimate stress was significant (*$p<0.001$). The data shown in these
Figure 12B:
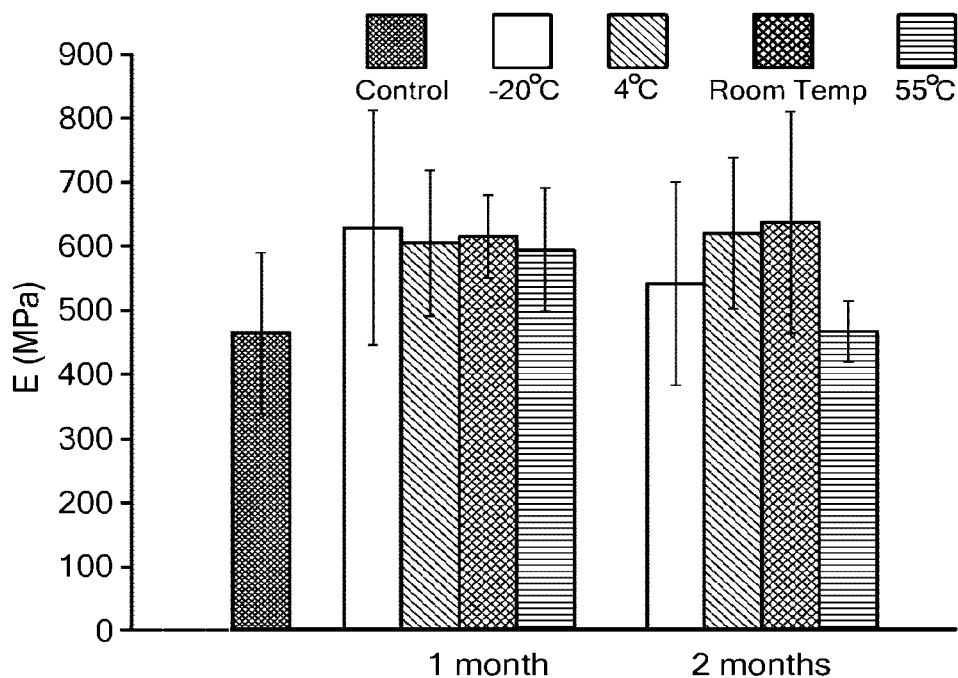

Mechanical compressive strength of stored devices was also determined. Devices containing antibiotic made according to the Group 2 formulation of Table 2 in Example 2 were evaluated by compressing in Direction 3 at a load rate of 2 mm/s. FIGS. 12A-12B shows compressive stress (FIG. 12A) and modulus (FIG. 12B) after 1 and 2 months of storage in each condition as indicated.

As shown in FIGS. 12A and 12B, shelf life and storage effects on the ultimate stress (FIG. 12A) and modulus (FIG. 12B) of devices made according to the Group 2 formulation of Table 2 in Example 2 tested after 1 and 2 months of storage resulted in higher ultimate stress and moduli than controls stored for only 1 week, but only ultimate stress was significantly increased (p<0.0001). The moduli also slightly increased after 1 and 2-month storage, but were not statistically significant (p>0.27) for all comparisons due to larger variability (FIG. 12B). Storage temperature had no effect on either of the mechanical parameters and no significant differences were found between the 1 and 2 month stored device specimens. These data in FIGS. 12A and 12B suggest that the devices generally increase their mechanical integrity after 1 month of storage and maintain it for at least an additional month of storage, regardless of the storage condition. One exception to this may be the device specimens stored at 55° C. which exhibited a slight degradation after 2 months, although this was also not statistically significant (see FIG. 12B).

Figures 13A, 13B, 13C:
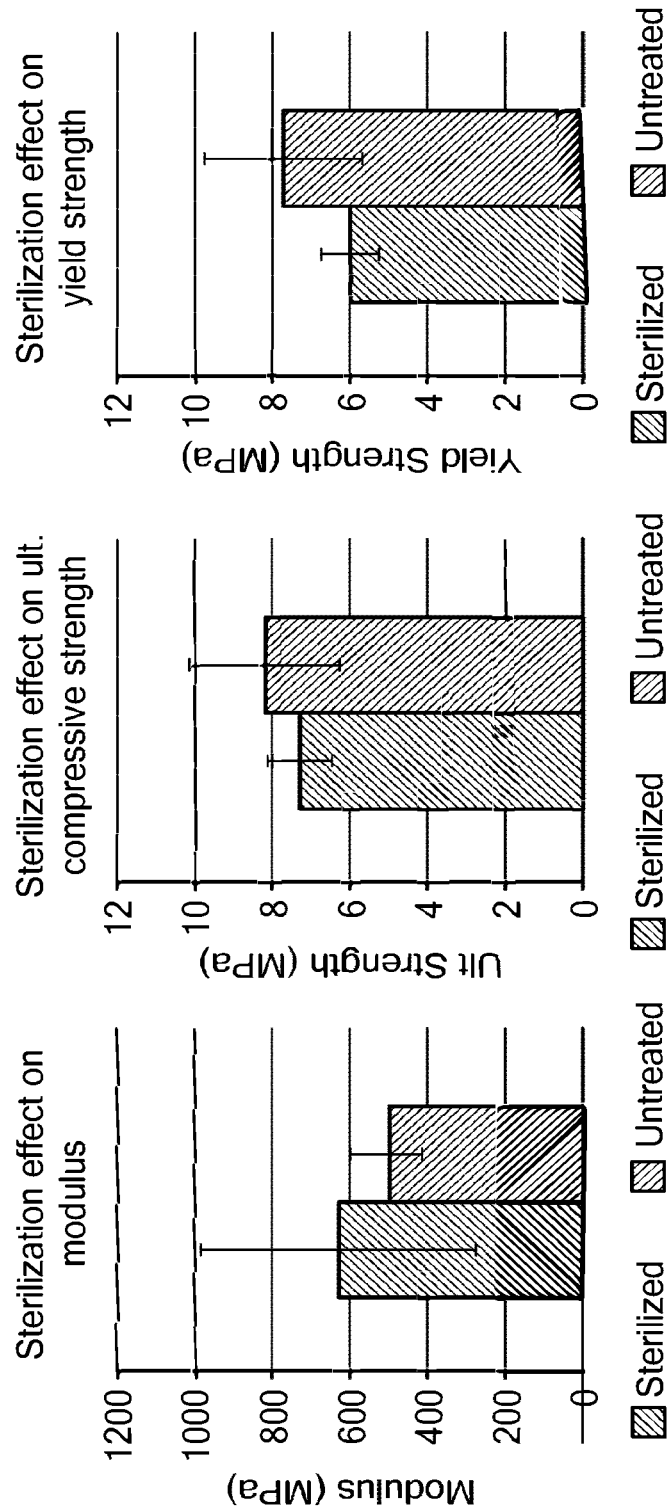
FIGS. 13A-13C are bar graphs showing the results of mechanical compression testing comparing the bulk modulus (FIG. 13A), compressive strength (FIG. 13B) and yield strength (FIG. 13C) for ElutiBone™ Group 3 devices (PCL, PEG, PLGA, calcium chloride, ProOsteon 500R and 10% w/w tobramycin) after ethylene oxide (Sterad) sterilization. The Group 3 devices are fabricated according to the Formulation 3 recipe in Table 1 of Example 1.

Similar testing was performed on sterilized and unsterilized devices made according to the Formulation 3 formulation in Table 1 of Example 1. As shown in FIGS. 13A-13C, sterilization had no significant effect on modulus (FIG. 13A), ultimate compressive strength (FIG. 13B) or yield strength (FIG. 13C) of the devices.

Example 4

As the value and relevance of a small animal model depends on the targeted application for the delivery system, a rabbit radial bone window model was selected to mimic the surgical removal of degraded or necrotic bone prevalent in revision total joint replacement surgery. Additionally, the radial defect model was chosen ethically to minimize pain and spontaneous fracture, as the radius and ulna are naturally fused in the rabbit, providing critical skeletal support during healing.

For these in vivo studies, the surgeries are performed aseptically in modern surgical facilities essentially as previously described (Smeltzer M. S. et al., J Orthop Res, 15(3): p. 414-21, 1997; Perry, A. C., et al., Clin Orthop Relat Res, (414): p. 95-100, 2003; Poelstra, K. A., et al., J Biomed Mater Res, 51(2): p. 224-32, 2000) and as described below herein using a 2 mm×2 mm×6 mm bone defect cut into the flat medial surface of the right radius of each New Zealand White rabbit, penetrating the medullary canal. However, the surgical procedure can also be modified by addition of a second survival surgery meant to mimic a revision surgery after implant infection for chronic reoccurring bone infection.

Example 5

Using the devices described in Examples 1 and 2 above, in vitro and in vivo studies were done.

Figure 14A:
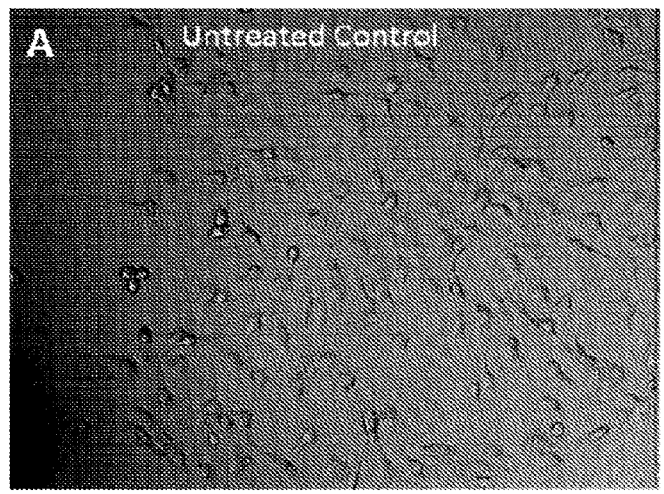
FIGS. 14A, 14B, and 14C are photographs showing cultured stromal cell cytotoxicity: untreated control cultured fibroblasts (FIG. 14A), exposed to a tobramycin-soaked ProOsteon fragments the same size as the molded devices (FIG. 14B), and exposed to an antibiotic-eluting molded composite bone void filler device (FIG. 14C). The live/dead stain (where dead cells stain red) was applied after culture with the bone void fillers for 24 hours. The data shown in these
Figure 14B:
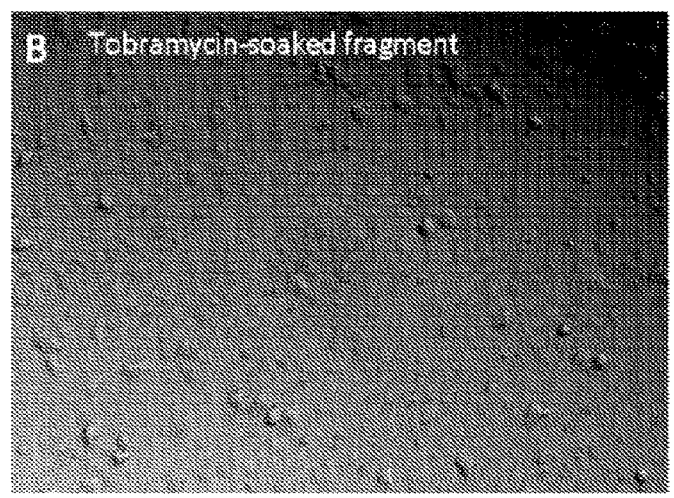
Figure 14C:
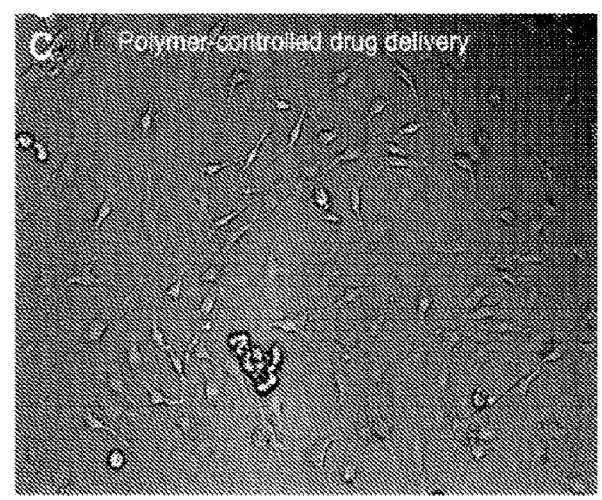

For in vitro studies, osteoblasts were grown in cell culture wells to approximately 80% confluency. Tobramycin-soaked bone graft or composite antibiotic-eluting bone void filler was then placed in a transwell that was inserted into the cell culture wells containing the 80% confluent osteoblasts. After culture for 24 hours, the cells were stained with propidium iodide for viability assessment. FIG. 14A shows untreated cells, FIG. 14B shows cells treated for 24 hours with tobramycin-soaked bone graft and FIG. 14C shows cells treated with antibiotic-eluting bone void filler (FIG. 14C).

An initial in vivo study focusing on the bactericidal activity of the devices, thereby assessing the time period during which drug can elute out of the devices. In this in vivo study, the devices were implanted into the radial bones of rabbits. FIGS. 15A-15D show radiographs (FIGS. 15A and 15B) and histology (FIGS. 15C-15D) of radial window defects in representative rabbits following medullary space inoculation using $10^5$ or $10^7$ CFU of S. aureus ATCC 49230. Note that FIGS. 15A-15D show representative animals of a cohort of control (i.e., FIGS. 15A and 15C) or test animals (i.e., FIGS. 15B and 15D). It should also be noted that in these studies, that control animals implanted with ProOsteon only and inoculated with $10^5$ CFU of S. aureus (i.e., representatives shown in FIGS. 15A and 15C) had to be euthanized at 2-4 weeks due to massive localized infection (a 2 week time point is shown in FIGS. 15A and 15C). In contrast, the animals implanted with the antibiotic PCL-PEG composite vone void filler device (fabricated according to Group 2 in Table 2 of Example 2 above) were subsequently inoculated with 100 fold more bacteria ($10^5$ CFU of S. aureus) and were able to survive without any notable detrimental effects (see FIG. 17) to study termination of 8 weeks.

In this in vivo study, different cohorts of animals were tested. Cohort 1 animals were implanted with a ProOsteon crouton (a clinical grade commercial coralline-derived bone graft inorganic biomaterial lacking any antibiotic) but had no infectious inoculum given during the surgical procedures. Cohort 1 thus served as a control for background infection. Cohort 2 animals were also implanted with a ProOsteon crouton but were also inoculated with $10^5$ CFU of S. aureus. Cohort 4 animals were implanted with molded composite bone void filler devices containing clinical grade coralline-derived inorganic bone void filler granules (i.e., a mixture of PCL, PEG, and ProOsteon) that was made according to the Group 2 formulation in Table 2 of Example 2 but that was lacking any loaded antibiotic, and inoculated with $10^5$ CFU S. aureus. Cohort 5 animals were implanted with a ProOsteon crouton that had been pre-soaked in a 10% solution of tobramycin prior to implantation and inoculated with $10^5$ CFU S. aureus. Cohort 7 animals were implanted with molded antibiotic-releasing composite bone void filler devices containing clinical grade coralline-derived inorganic bone void filler granules and solid granulated tobramycin (made according to the Group 2 formulation in Table 2 of Example 2) and inoculated with a lethal dose of $10^7$ CFU (100 times more than other cohorts) of S. aureus.

Figure 16:
FIG. 16 is a bar graph showing the amounts of bacteria (in colony forming units, or CFU) cultured from samples taken at the time of euthanasia from tissue (black bars), bone (gray bars) and blood (dark gray bars) of animals from Cohort 1, Cohort 2, and Cohort 7. In cohort 1 an unaltered ProOsteon crouton was implanted and no infectious inoculum was given. In Cohort 2 an unaltered ProOsteon crouton was implanted and an infectious inoculum of $10^5$ CFU of S.

For the results shown in FIG. 16, swabs of the bone and soft tissue surrounding the surgical implant site containing the molded composite bone void filler devices were taken upon euthanasia of the animals. The swabs were used to inoculate 5% sheep blood agar plates. Bacteria were allowed to grow at 37° C. for 24-48 hours and bacterial colonies were counted. Blood samples from the same cohorts were also cultured this way. The results from Cohort 1, Cohort 2, and Cohort 7 are shown in FIG. 16. In cohort 1 an unaltered ProOsteon crouton was implanted and no infectious inoculum was perioperatively applied. In Cohort 2 an unaltered ProOsteon crouton was implanted and $10^5$ infectious inoculum was perioperatively applied. In cohort 7, a Group 2 crouton from Example 2, Table 2 (PCL, PEG, ProOsteon granules, tobramycin) was dip-coated in a PCL/acetone solution, dried, sterilized, and then was implanted into the animal and $10^7$ CFU of inoculum was perioperatively applied. The data shown in FIG. 16 shows the CFU observed at the time of euthanasia in the soft tissue (black), bone (light grey), and blood (dark grey). Note that infection in the blood was never observed in any of the cohorts tested. This lack of infection in the blood indicated that the infection was localized and not systemic. Moreover, because the infection was localized at the site of implantation, it suggests that the infection stems from the inoculated bacteria given to Cohorts 2 and 7, and not from an infection that the animal may have picked up elsewhere.

Note that no significant differences in the incidence of infection were observed between Cohort 1 controls (non-infected) and Cohort 7 animals implanted with antibiotic-releasing molded composite bone void filler devices and infected with $10^7$ CFU of S. aureus.

For the results shown in FIG. 17, after implantation, the animal's health was monitored and scored based on a modified Checkett's system where each score (1-4) was based on the soft tissue inflammation, radiographic signs of inflammation or infection, redness and inflammation of the surgical site, and the animal's temperature. Higher scores indicate that the animal's health was declining. In cohort 1 an unaltered ProOsteon crouton was implanted and no infectious inoculum was given. In Cohort 2 an unaltered ProOsteon crouton was implanted and inoculated with $10^5$ CFU of S. aureus. Note that these Cohort 2 animals had to be euthanized at an average of 3 weeks so the scoring abruptly ends at this point (see black squares on black dotted line in FIG. 17). Cohort 4 animals were implanted with an implant made from PCL, PEG, and ProOsteon granules (formulated according to Group 2 in Table 2 of Example 2 without tobramycin) and inoculated with $10^5$ CFU of S. aureus. Cohort 5 animals were implanted with a ProOsteon crouton that was soaked in a 10% solution of tobramycin prior to implantation and inoculated with $10^5$ CFU of S. aureus. Cohort 7 animals were implanted with the antibiotic releasing molded composite bone void filler devices (PCL, PEG, ProOsteon, and tobramycin—made according to the Group 2 formulation from Table 2 of Example 2) and inoculated with $10^7$ CFU of S. aureus. Note that animals in Cohort 7 experienced morbidity similar to the non-infected surgical control of Cohort 1.

FIG. 18 shows the percentage of survival of animals in Cohorts 1, 2, 4, 5, and 7. In cohort 1 an unaltered ProOsteon crouton was implanted and no infectious inoculum was given. In Cohort 2, an unaltered ProOsteon crouton was implanted, and animals were inoculated with $10^5$ CFU of S. aureus. In cohort 4, a group 2 crouton (i.e., Group 2 from Table 2 of Example 2) formulated without tobramycin (PCL, PEG, ProOsteon granules) was implanted, and animals were inoculated with $10^5$ CFU of S. aureus. In cohort 5, a ProOsteon crouton was soaked in tobramycin prior to implantation, and animals were inoculated with $10^5$ CFU of S. aureus. In cohort 7, a Group 2 crouton formulated according to Table 2 of Example 2 (PCL, PEG, ProOsteon granules, tobramycin) was implanted, and animals were inoculated with $10^7$ CFU of S. aureus. As FIG. 18 shows, the animals implanted with the Group 2 formulation from Table 2 of Example 2 in Cohort 7 experienced morbidity similar to the non infected surgical control animals in Cohort 1.

As the results of FIGS. 15A-18 show, rabbits treated with tobramycin-loaded implants effectively resisted infection for at least up to eight weeks. Based on the results, we predict that the rabbits treated with tobramycin-loaded implants will effectively resist infection for up to 12 weeks. In contrast, the rabbits treated with drug-free blank bone void filler controls acquired a severe infection, resulting in the bone void filler being pushed out of the bone.

A second in vivo study was performed, focusing on the osteoconductive activity of the devices. In these studies, the devices were implanted into the radius bones of rabbits, and no infectious inoculum was given. FIGS. 19A-19B are micro-CT images of the devices made according to Formulation 4 of Table 1 of Example 1 and implanted into the flat medial surface of the rabbit's radius. The figures show the implanted device at time "zero" (i.e., at the time of implant) (see FIG. 19A) and the implanted device taken twelve weeks after implantation (FIG. 19B). In FIGS. 19A and 19B, the label "G" indicates the device (or what is left of the device after it has been resorbed by the body) and the label "NB" indicates new bone. Note that the medullary canal was destroyed during the surgical implantation (see FIG. 19A) but the destroyed medullary canal has been re-established by new bone in FIG. 19B.

Additional micro-CT images of the implanted devices are shown in FIGS. 20A-20D. The device implanted in FIGS. 20A-20D were made using Formulation 4 of Table 1 in Example 1, above. FIGS. 21A and 21B show the results of backscatter Electron (BSE) image analysis at 12 weeks following implantation of the Formulation 4 device (made in accordance with Formulation 4 from Table 1 of Example 1 above) with no infectious inoculum. In FIG. 21A, the area labeled "G" is the device and the area labeled "NB" is new bone. Arrows in FIG. 21A point to new formed bone bridge. ProOsteon granules can be seen scattered throughout the new bone in FIG. 21A. Note that the thickness of the device is significantly reduced from the original 2 mm. FIG. 21B shows a backscatter electron microscopy image of the one section taken from a rabbit (namely rabbit #102) that does not show complete bone bridging. Arrows in FIG. 21B point to the tubular structure, likely a blood vessel, running from the endosteal space to the periosteal surface.

FIG. 22 shows the actively mineralizing bone surfaces in an animal implanted with a device made according to Formulation 4 of Table 1 of Example 1 above, with no infectious inoculum given to the animal. For these studies, prior to animal necropsy at the predefined 12-week endpoint, rabbits implanted with a Formulation 4 device were injected with fluorescent calcein green dye via the ear vein to fluorescently label actively mineralizing bone and calculate the mineral apposition rate (MAR). Analysis of bone mineral apposition revealed actively remodeling bone surfaces indicated by incorporation of calcein green. The area labeled "G" in FIG. 22 indicates the implanted device (or what is left of the device after resorption by the body), and the area labeled "NB" indicates new bone.

Table 4 below provides a summary of dynamic histomorphometry measurements for two rabbits (namely rabbit #102 and #103) implanted with devices made according to Formulation 4 from Example 1, Table 1 (PCL, PEG, PLGA, Calcium chloride, tobramycin, ProOsteon granules with a surface coating of ProOsteon granules) in the radial window model, with no infectious inoculum.

TABLE 4

|  | % dLs | % sLs | % MS | MAR (µm/day) | NBA (µm²) |
|---|---|---|---|---|---|
| Periosteal Measures | | | | | |
| Rabbit 102 | 5.35 ± 1.48 | 19.86 ± 6.14 | 15.28 ± 2.64 | 1.90 ± 0.45 | 21845.29 ± 7720.62 |
| Rabbit 103 | 40.61 ± 10.87 | 19.50 ± 5.20 | 50.36 ± 11.07 | 2.79 ± 0.12 | 177459.43 ± 57854.08 |
| Endosteal Measures | | | | | |
| Rabbit 102 | 12.46 ± 2.94 | 9.05 ± 4.53 | 16.98 ± 3.59 | 2.54 ± 0.15 | 23745.75 ± 1907.86 |
| Rabbit 103 | 26.89 ± 5.06 | 10.67 ± 4.21 | 32.23 ± 6.78 | 3.36 ± 0.23 | 41736.85 ± 11034.22 |

The antibiotic-eluting implantable devices described in Examples 1 and 2 were able to provide effective antimicrobial protection against an ATCC strain of S. aureus in a rabbit perioperative infection model (see FIGS. 15A-18)—1$^{st}$ in vivo experiment) and allow bone healing (see FIGS. 19A-22—2$^{nd}$ in vivo experiment).

The surgeries described in this Example 3 were successful with no systemic infection seen in any of the nine animals. The implanted grafts provided mechanical stability. FIG. 18 shows that the coated implantable device (Cohort 7: grey circles with black line in FIG. 18) more than doubled the survivability of infected host animal implanted as compared to infected animals implanted with a prior art implant.

Example 6

To improve bone ingrowth into the implanted device in the rabbit model, each fabricated device is surface-enriched with an embedded microporous coating of synthetic bone graft solids (FIG. 2B). This process described in above in Example 1 for Formulation 4.

Micro-CT image analysis of the implant site from 2 rabbits implanted with the composite device demonstrated increased mineralization with this coating technique (see FIGS. 19A-19B and 20A-20D). FIGS. 19A and 19B show the implant (labeled "G") at time "zero" and after twelve weeks following implantation in the radius of a rabbit. As shown in FIGS. 19A and 19B, the destroyed medullary cannal has been re-established with new bone (NB in FIG. 19B). The arrow in FIG. 20D shows the suspected woven bone indicated by the more sparse mineralization present. FIGS. 20C and 20D show the re-established marrow space. FIGS. 20A and 20B show the shallower groove with sparse mineralization, presumably representing the bone void filler fragments of the implanted device.

This device manufacturing process has several key advantages over more traditional polymer coating methods on implants or drug release formulations, including: 1) precise antibiotic delivery over an extended duration; 2) device mechanical properties can be optimized to suit specific void filler demands; 3) the implant can be cast in varied morphologies according to the geometry of the desired application, resulting in a better mechanical and anatomical fit to the bone defect; 4) well-accepted local pharmaceutical delivery is beneficial, perhaps essential in cases of compromised vasculature at the implant site for effective antimicrobial and therapeutic treatments. These advantages can be contrasted to most current local release devices that suffer from inadequate drug tissue pharmacodynamics, limited chemical stability, and local inflammatory responses, as evidenced by FIGS. 14A-14C). Furthermore, as shown in FIGS. 12A-12D, antibiotic protection in a radial window bone defect rabbit infection model using the same fabrication techniques was validated in vitro with S. aureus killing.

Example 7

In this example, composite devices comprising dispersed drug-containing microparticles with variable, tailored drug elution kinetics and proven biological efficacy against common pathogens involved in implant infections are used in combination with dispersed solid unencapsulated drugs co-residing in the same composite formulation Current orthopedic drug delivery materials (e.g., antibiotic-loaded bone cement, OsteoSetT, etc.) are limited in their longevity by a prominent early-stage drug burst (see, e.g., Witso E., et al., Acta Orthop. 76(4): 481-6, 2005; Winkler, H, et al., J Antimicrob Chemother, 2000. 46(3): p. 423-8, 2000). In addition to inadequate pharmacokinetics, these current orthopedic drug delivery materials are incapable of releasing more than a single drug; thus, limiting their clinical versatility, efficacy and allowing the development of antibiotic-resistant bacteria.

To improve the versatility of the composite device to treat polymicrobial PJIs, a variety of drugs (vancomycin, ciprofloxacin, tobramycin, etc.) and their combinations are encapsulated to slow drug release compared to various dispersed non-encapsulated drugs residing as formulated as described above in the composite implant device. Encapsulating materials include common lipids (lecithins, triglycerides) and biomedical polymers (preclinical and clinical examples not intended to be limiting are PCL and poly(lactide-co-glycolide) (50:50 ratio PLGA) microparticles). Due to the different degradation properties (example: PCL for longer release or lecithins or starches or PLGA for shorter duration release) of the encapuslating polymers, drugs are predicted to be released in a temporally staged manner over an extended duration (see FIG. 23) using combinations of dispersed encapsulated and unencapsulated drugs in various mass ratios within the composite device. As the theoretical graph in FIG. 23 shows, the composite device (Groups 1-3) described herein is expected to result in controlled drug release that maintains drug concentrations above the minimal inhibitory concentration at the implant site throughout the extended release time course of 6-8 weeks. These data are based on studies published by Mahender Avula et al. Biomaterials 34(38): 9737-9746, 2013 describing the release of the PLGA-encapsulated drug masitinib in vitro into PBS under sink conditions as a function of PLGA molecular weight.

Figure 24A:
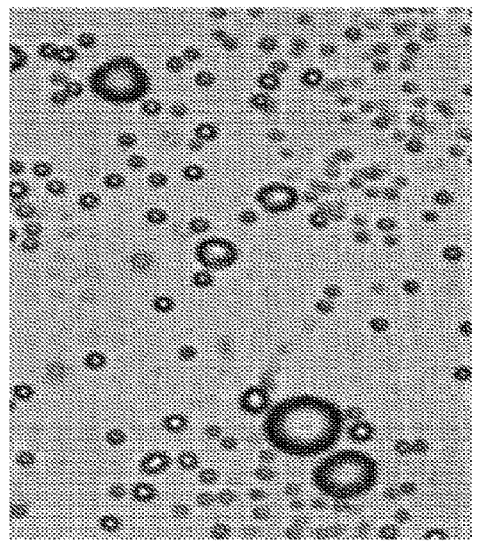
Figure 24C:
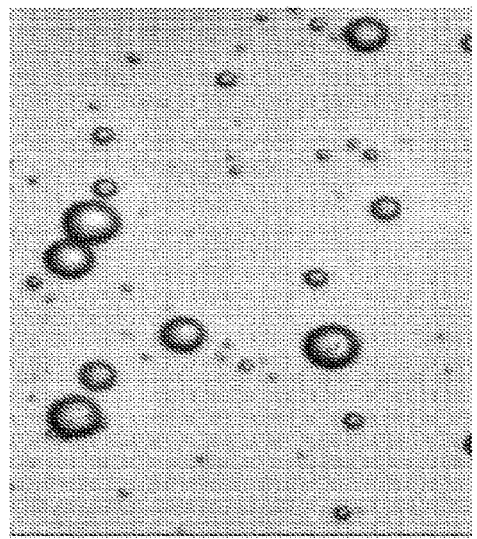
Figure 24B:
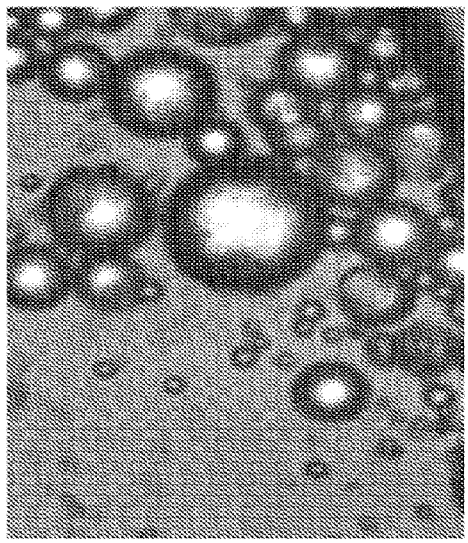
Figure 24D:
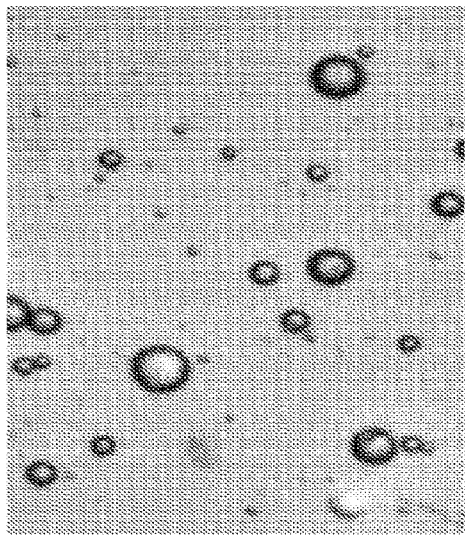

To achieve the prolonged release of drug theoretically depicted in FIG. 23, initially one of the three classes of antibiotics: aminoglycosides, fluoroquinolones, and glycopeptide (e.g., tobramycin ciprofloxacin, and vancomycin, respectively) is encapsulated into either PCL (long duration release) or PLGA (shorter duration release) microparticles. FIGS. 24A-24D are images of PCL particles (FIGS. 24A-24B) and PLGA particles (FIGS. 24C-24D) either without (FIGS. 24A and 24C) or with encapsulated drug (FIGS. 24B and 24D). Note that the particles containing drug (FIGS. 24B and 24D) differ slightly in appearance from their drug-free counter parts (FIGS. 24A and 24C, respectively).

These antibiotics are chosen based on their known efficacy against the reported most prevalent PJI bacteria; however, these antibiotics can be selected depending upon the identity of the pathogen(s) at the site of infection of a particular implant and patient. Thus, the antibiotic selected is one that actively targets the pathogen present at the site of infection. As shown in FIGS. 5B-5D, the antibiotic drug, tobramycin, elutes from the various composite bone void filler device formulations described herein for over ten weeks when dispersed as an unencapsulated solid in the device. Use of encapsulation strategies for all or part of each drug dispersed within the composite device will modify this drug release profile from the device.

In vitro elution kinetics and standard microbiology are utilized as already described herein to assess the ability of microencapsulated drugs incorporated into the composite bond void filler devices to temporally stage the release of one or multiple antibiotics over an extended duration against the prevailing causative microbes identified in periprosthetic joint infections.

Thus, as anticipated in the drug release profile set forth in FIG. 23, polymer-mediated control over drug release kinetics is an attractive alternative technique for the improved local delivery of antibiotics to bone where surgical access for repair also permits filler deployment at that site.

Given the different elution times of these drugs from the composite bone void filler, each type of encapsulated drug particle can, either individually or in combination with another type of particle, or with combinations of one or more unencapsulated drugs, be incorporated into the composite implantable device according to the methods described in Example 1 above.

Microparticle and or nanoparticle encapsulated drug will be synthesized according to a known double-emulsion solvent evaporation technique with sonication and as previously described (see, e.g., Abbas, A. O. et al., J Pharm Sci, 2008. 97(7): p. 2448-61, 2008; Avula, M. N., et al., *Biomaterials* 34: 9737-9746 (2013), and Wang and Grainger, Pharm Res. 27(7): p. 1273-84, 2010).

Characterization of the implantable devices with encapsulated drug loading includes determination of encapsulating particle size distribution, zeta potential and surface morphology, according to established methodologies (see Wang and Grainger, (2010) vida supra). Extracting and quantifying the antibiotic using known methods determines antibiotic loading and encapsulation efficiency (Avula, M. N., et al., *Biomaterials* 34: 9737-9746, 2013). Briefly, each fabricated device is incubated in sterile saline at 37° C. to release the drug encapsulated in PLGA and PCL microparticles (incorporated into the bulk of the antibiotic-containing composite bone void filler). Antibiotic elution kinetics are determined using methods described above in Example 2. Additionally, drug elution is characterized from PLGA and PCL microparticles not formulated into the composite device as a control. Furthermore, device formulation with unencapsulated drug serves as a control for comparing the encapsulation release system using the methods described here (see, e.g., FIGS. 5B-5D and 14A-14C). Subsequently, the bioactivity of each released antibiotic is assessed in vitro using both Kirby-Bauer testing and time-kill assays against one of the three most commonly occurring pathogens isolated from infections at implantation sites (e.g., *S. aureus*). Additionally, the antibiotic-releasing bone graft is incubated with single PH-associated clinical isolates. Encapsulated and unencapsulated drugs in one or more combinations within the composite device are contemplated to produce extended release of one or more antimicrobial agents from the device with independently variable kinetics and time durations, depending on respective mass loading and formulation variables.

Table 5 provides an example set of studies typically performed to assess the ability of the composite drug-formulated devices described herein to (a) reduce or prevent infection at the implantation site and (b) allow replacement of the device, eventually, with host bone.

TABLE 5

| Cohort | Type of bacteria | Microencapsulating polymer | | Drug | | | Number of animals |
|---|---|---|---|---|---|---|---|
| | | PCL | PLGA | Vancomycin | Ciprofloxacin | Tobramycin | |
| 1 | A | x | X | | | | |
| 1a | A | x | X | X | X | | 3 |
| 2 | B | x | X | X | X | | 3 |
| 2a | B | x | X | X | X | | 3 |
| 3 | C | x | X | X | X | | 3 |
| 3a | C | x | X | X | X | | 3 |
| 4 | A | x | X | x | | x | 3 |
| 4a | A | x | X | x | | x | 3 |
| 5 | B | x | X | x | | x | 3 |
| 5a | B | x | X | x | | x | 3 |
| 6 | C | x | X | X | | X | 3 |
| 6a | C | x | X | x | | x | 3 |
| 7 | A, B, C | x | X | x | x | | 3 |
| 7a | A, B, C | x | X | x | x | | 3 |
| 8 | A, B, C | x | X | X | | X | 3 |
| 8a | A, B, C | x | X | x | | x | 3 |
| 9 | A, B, C | x | X | | x | x | 3 |
| 9a | A, B, C | x | X | | x | x | 3 |
| 10 | A, B, C | | | | | | 3 |

Note that the types of bacteria can be any bacteria and types of fungus any type of fungus. For example, Bacteria A may be S. aureus. Bacteria B may be P. acnes. Bacteria C may be coagulase negative S. epidermidis. Bacteria D may be S. epidermidis. Fungus A may be C. albicans. Fungus B may be A. fumigates.

Incubated bacteria will be harvested across a 6-week time course and either multiplex or singleplex PCR are performed for mecA, vanA/B, KPC antibiotic resistance markers to monitor the development of drug resistance.

A common concern with microparticle formulations is the drug encapsulation efficiency. To mitigate this limitation, surfactants can be added to the double-emulsion solvent evaporation system to facilitate the appropriate hydrophobic interactions and increase the drug encapsulation efficacy. Alternatively, a variety of raw drug formulations (salt forms versus a free base forms) can be utilized to optimize the hydrophobic interactions in the encapsulation system. The overall weight percent of particles in the bulk can also be increased to compensate for suboptimal encapsulation efficacy. Alternatively, if the amount of drug encapsulated is insufficient to provide antimicrobial activity, unencapsulated drug may also be included in the polymer formulation. Sequential release of distinct drugs may be improved by the addition of low intensity pulsed ultrasound (LIPUS) at 2 weeks and 6 weeks, time points chosen to match the standard of care clinic visits following TJR revision surgery. Finally, if some of the most prevalent PJI causative bacteria are unable to be cultured, analogous strains purchased from the ATCC may be used.

Example 8

In this example, the implantable device described herein is used in conjunction with a prosthesis.

Annual incidence of infections to orthopedic implants in the United States is substantial: 12,000 total joint infections and over 100,000 infected bone fixation implants annually. This produces a substantial cost both in terms of patient morbidity and financial coverage of these infections. All medical device-related infections are estimated to cost $1.7-4.6 billion in excess medical costs to U.S. hospitals annually. If 20% of these device-related infections could be prevented, $300-900 million in medical costs and much patient morbidity, pain and suffering could be saved.

Cement-Less Biological Bone Fixation and Implant Porosity.

Cement-less fixation represents an alternative method to popular acrylic bone cements to place and stabilize metal implants in bone. The method intends to stabilize metal implants using the patient's own direct bone-implant on-growth, on-bonding between bone and implant surface, and mechanical fixation from this interaction. The method, used in various forms since the 1980's, is intended to surpass cemented implant fixation as the method of the future— PMMA and standard thermoset cement technology will be eventually passed over in favor of cementless implant-bone bonding relying on direct bone-implant bonding. Typically, cementless fixation has been produced by host bone in-growth into carefully designed and fabricated implant pores of sufficiently large size. Porosity is critical to promote and produce this bone on-bonding fixation process with an implant. When new bone from the patient calcifies within these pores, this allows mechanical interlocking and stabilization of the bone-implant interface, eliminating the need for acrylic cements. Importantly, the ideal pore size should mimic that of native cancellous bone that ranges from 400-500 microns (dense cortical bone by comparison is only 8% porous). By contrast, most porous metallic implants (e.g., commercially pure (CP) titanium, cobalt-chrome alloys, Ti-6Al-4V alloy) have pores ranging from 100-400 microns, with 30-50% total porosity. Proper implant pores sizes and pore densities prompt enhanced bone-based fixation, achieved earlier than using fixation with allograft cortical bone, in some cases a matter of weeks.

Zimmer (Warsaw, Ind., USA) introduced their Trabecular Metal™ implants fabricated of elemental tantalum metal (a rare and highly corrosion resistant metal applied to dental implants since the 1950s) using a vapor deposition technique to create a metallic strut configuration that is similar to trabecular bone architecture. The crystalline micro- and nano-texture of a Trabecular Metal strut is conducive to direct bone apposition. Furthermore, implants fabricated from tantalum offer high porosity, allowing not only hone around implant sites to grow onto the material but also into it—a process known as osseo-incorporation or biological fixation. Zimmer's trabecular metal implants are 70-80% porous, similar to cancellous bone. Studies on dental implants con airing Trabecular Metal in canine mandibular models began in 2010 and showed evidence of in-growth by maturing bone as early as two weeks after implantation. Moreover, transcortical animal implant studies have demonstrated excellent new bone in-growth of Zimmer's Trabecular Metal implants within eight weeks of surgery, promoting rapid fixation strength. According to the Zimmer company reports, human trials data are currently being collected with the first long-term results expected to be available in 2012. Zimmer has gained CE approval for another dental Trabecular Metal implant in Europe in 2011 and anticipates market approval for the USA through the Food and Drug Administration soon. Trabecular Metal has been already used for more than a decade in many of Zimmer's orthopaedic devices.

Infection and Cementless Fixation and Porosity.

Although cementless fixation via porous metallic implants continues to provide mechanical integrity, there is an increased long-term risk of revision due to infection in hybrid and cemented implants compared to uncemented implants as evidenced by several clinical studies on total hip arthroplasties. There are considerable indications that cementing produces substantial infection risk, even acting as a nidus of infection. Hence, acute infection rates in this host post-implantation are as significant in cementless and cemented fixation in studies reported to date. Significantly, infection serves to inhibit bone generation and on-growth, limiting implant stabilization by bone growth. Limited (and clinically preliminary) evidence for more chronic infections indicates that cementless fixation infection incidence longer-term is less than for cemented. Cemented fixation notably addresses infection risk with antibiotic-containing cements, but these suffer from low fractional release and low antimicrobial capabilities long term. The presence of the cement may act as a foreign body, enhancing rates of infection after antibiotic release is exhausted after a few days post-implantation. A significant unmet clinical need and opportunity exists currently in addressing infection risk in cementless fixation with a resorbable polymer/granular bone/drug composite coating or press-fit wafer that accommodates cement-less fixation while mitigating infection risk short-term. This allows bone regeneration without infection.

Porous metal fixation designs on implants represent a known clinical infection risk. The methods and compositions described herein as applied to cementless fixation implants may mitigate this risk for the following reasons.

First, the antibiotic eluting implants described herein are composite polymer-bone graft-drug matrices. Also, the implants described herein can be patterned onto (e.g., coated onto) metallic implants to produce local high-resolution zones of antibiotic-release on or adjacent to cementless porous metal areas (see FIG. 25C). Additionally, the implant formulations described herein can be applied in microdot patterns on or around porous metal zones on implants (see FIGS. 25A and 25B). Since the implant formulations described herein can be tailored to degrade in months, this will provide antibiotic protection as bone in-growth is over the same time frame, and then fully resorb fully as bone ingrowth of host bone onto the device matures at several months post-implantation. Given the ease of manipulation of the implants described herein, the implants can be printed robotically or painted by hand or press-fit into pre-machined grooves or designated drug-release zones on metal implants and release drug for weeks while resorbing as bone in-growth occurs. Likewise, the implants can be molded or carved to meet specific dimensions or sizes (e.g., to shape the implant to fit within a specific defect site or to be placed adjacent to the prosthesis cementless fixation area). Moreover, the implants described herein, which are designed to resorb at rates commensurate with bone in-growth into porous metal, can be loaded with diverse drugs (e.g., antibiotics, growth factors, anti-inflammatory, anti-osteoporotic drugs), even in different areas of the implant using precision spray coating, printing, or press-fitting of pre-fabricated pieces.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. An implantable device comprising a uniform mixture of components including:
    a degradable polymer,
    bone,
    a drug,
    a macroporagen including polyethylene glycol, and
    a microporagen selected from the group consisting of a salt of an alkali metal, a salt of an alkaline earth metal, and combinations thereof;
    wherein:
    (a) the amount of bone by weight exceeds the combined weight of all the other components,
    (b) the amount of degradable polymer is less than 30% by weight of the device;
    (c) the components are selected and provided in relative amounts such that following implantation:
        (i) water molecules dissolve the microporagen to create micropores in the device,
        (ii) the water molecules enter the resulting micropores,
        (iii) the entering water molecules dissolve or degrade the macroporagen and the degradable polymer,
        (iv) the drug is released while creating sufficient space for cell migration into the device and while retaining structural integrity of the device long enough to serve as a scaffold to establish osteoconduction, and
    (d) the degradable polymer has a degree of crystallinity and molecular weight selected to cause the degradable polymer to degrade in a manner to render the device resorbable and able to release the drug over a time period of at least six weeks following implantation.

2. The device of claim 1, wherein the microporagen is selected from the group consisting of a carbonate, a chloride, a sulfate, and combinations thereof.

3. The device of claim 1, wherein the microporagen is selected from the group consisting of $CaCl_2$, $MgCl_2$, and $MgCO_3$.

4. The device of claim 1, wherein the degradable polymer comprises a composition selected from the group consisting of polycaprolactone, poly(lactic-co-glycolic) acid, and mixtures thereof.

5. The device of claim 1, wherein the bone is synthetic bone.

6. The device of claim 1, wherein the macroporagen further includes a composition selected from the group consisting of alginate, polyvinylpyrrolidone, NaCMC, hydroxypropylcelluose, hyaluronic acid, and combinations of the foregoing.

7. The device of claim 1, further comprising a coating covering the uniform mixture.

8. The device of claim 7, wherein the coating comprises bone.

9. The device of claim 1, wherein the drug is microencapsulated.

10. The device of claim 1, wherein the amount of degradable polymer by weight exceeds the amount of macroporagen by weight, and the amount of macroporagen by weight exceeds the amount of microporagen by weight.

11. A method for treating and/or preventing infection at a site of implantation in a patient in need of a bone or joint replacement, comprising implanting the device of claim 1 into the site of implantation.

12. A method for manufacturing the device of claim 1 comprising:
    a) combining:
        the degradable polymer,
        the drug,
        the bone,
        the macroporagen including polyethylene glycol, and
        the microporagen selected from the group consisting of a salt of an alkali metal, a salt of an alkaline earth metal, and combinations thereof over heat to make a uniform mixture by increasing the mixture temperature;
    b) dispensing the heated uniform mixture into a mold of a pre-determined shape and size according to the anatomical need;
    c) cooling the uniform mixture to a temperature at which the uniform mixture will harden in the mold; and
    d) releasing the hardened uniform mixture from the mold to produce the device.

13. The method of claim 12, wherein the method further comprises
    e) contacting the surface of the implantable device produced by step (d) with morselized bone, and
    f) allowing the morselized bone to embed into the surface of the device to form a coating of bone on the device using mechanical force, ultrasonic energy or locally applied heat.

14. The method of claim 12, wherein the uniform mixture is a composite.

* * * * *